US008785724B2

(12) United States Patent
An et al.

(10) Patent No.: US 8,785,724 B2
(45) Date of Patent: Jul. 22, 2014

(54) REGULATOR FOR FLOWERING TIME, TRANSGENIC PLANT TRANSFORMED WITH THE SAME, AND METHOD FOR REGULATING FLOWERING TIME

(75) Inventors: Gynheung An, Pohang (KR); Shinyoung Lee, Kwangju (KR); Dong-Hoon Jeong, Pohang (KR); JiHye Yoo, Seoul (KR); Choong-Hwan Ryu, Pohang (KR); Jong-Seong Jeon, Pohang (KR); Sung-Ryul Kim, Pohang (KR); Young-Ock Kim, Pohang (KR); Joonyul Kim, Pohang (KR); Suyoung An, Pohang (KR); Jong-Jin Han, Pohang (KR); Min-Jung Han, Pohang (KR)

(73) Assignees: Posco, Pohang; Postech Foundation, Pohang (*) Notice: Subject to any disclaimer, the term of this patent is extended or adjusted under 35 U.S.C. 154(b) by 1392 days.

(21) Appl. No.: 11/767,193

(22) Filed: Jun. 22, 2007

(65) Prior Publication Data
US 2011/0191908 A9    Aug. 4, 2011

Related U.S. Application Data

(63) Continuation of application No. PCT/KR2005/004461, filed on Dec. 22, 2005.

(60) Provisional application No. 60/638,460, filed on Dec. 22, 2004.

(51) Int. Cl.
*A01H 1/00* (2006.01)

(52) U.S. Cl.
USPC .......................................... 800/278; 800/290

(58) Field of Classification Search
None
See application file for complete search history.

(56) References Cited

U.S. PATENT DOCUMENTS

2005/0160498 A1* 7/2005 Chung et al. .................. 800/287

FOREIGN PATENT DOCUMENTS

| JP | 2004-290190 A | 10/2004 |
|---|---|---|
| KR | 10-2002-0031139 A | 4/2002 |
| WO | WO 96/14414 A | 5/1996 |
| WO | WO 2004/031349 A | 4/2004 |
| WO | WO 2004/061122 A | 7/2004 |

OTHER PUBLICATIONS

Brucker et al (Planta (2005) 220:864-874).*
Hassidim et al (2009, Planta 230:481-491).*
Lim Jeongsim et al: "Two rice MADS domain proteins interact with OsMADS1" Plant Molecular Biology, Springer Dordrecht, NL. vol. 44. No. 4, pp. 513-527.
Jeong Jona-Seong et al: "Production of transgenic rice plants showing reduced heading date and plant height by ectopic expression of rice MADS-box genes" Molecular Breeding, vol. 6, No. 6, Dec. 2000. pp. 581-592.
Lee S. et al (2004). Functional analyses of the flowering time gene OsMADS50, the putative Suppressor-Like 20 (SOC1/AGL20) ortholog in rice. The Plant Journal, 38, 754-61.
Lee S. et al (2003). Systematic reverse genetic screening of TDNA tagged genes in rice for functional genomic analyses: MADS-box genes as a test case. Plant Cell Physiology, 44 (12). 1403-11.
Moon YH. et al (1999). Determination of the motif responsible for interaction between rice APETALA1/AGAMOUS-LIKE9 family proteins using a yeast two-hybrid system. Plant Physiology, 120(4), 1193-1204.
Kang HG. et al (1997). Characterization of two rice MADS box genes that control flowering time. Molecluar Cells, 7(4), 559-66.
Tadege Million et al: "Reciprocal control of flowering time by OsSOC1 in transgenic, Arabidopsis and by FLC in transgenic rice" Plant Biotechnology Journal Sep. 2003, vol. 1, No. 5. pp. 361-369.
Shinozuka Y et al: "Isolation and characterization of rice MADS box gene homologues and their RFLP mapping" DNA Research: An international Journal for rapid publication of reports on genes and genomes 30 Apr. 30, 1999. vol. 6, No. 2, pp. 123-129.
Heuer S et al: "The mads Box Gene Zmmads2is Specifically expressed in maize pollen and during maize pollen tube growth" Sexual Plant Reproduction, Berlin, De. vol. 13. No. 1. 2000. pp. 21-27.
Lim Jeongsim et al: "Two rice MADS domain proteins interact with OsMADS1" Plant Molecular Biology, Springer Dordrecht, NL. vol. 44. No. 4, pp. 513-527. 2000.
Jeong Jong-Seong et al: "Production of transgenic rice plants showing reduced heading date and plant height by ectopic expression of rice MADS-box genes" Molecular Breeding, vol. 6, No. 6, Dec. 2000. pp. 581-592.
Fornara F et al: "MADS-box genes controlling flower development in rice" Plant Biology. vol. 5, No. 1, Jan. 2003, pp. 16-22.
Yano M; et al: "Hd1, a major photoperiod sentivity quantitative trait locus in rice, is closely related to the arabidopsis flowering time gene CONSTANS," The Plant Cell 12:2473-2483, Dec. 2000.
Griffiths S; et al: "The evolution of CONSTANS-Like gene families in barley, rice and Arabidopsis " Plant Physiology, 131:1855-1867, Apr. 2003.
Shin Bong-Soo; Lee Jeong-Hyun; Lee Jeong-Hwan; Jeong Hyun-Joo; Yun Choong-Hyo; Kim Jeong-Kook: "Circadian regulation of rice (*Oryza sativa* L.) CONSTANS-like gene transcripts," Mol. Cells 17 (1):10-16, 2003.
Putterill J; et al. "The CONSTANS gene of arabidopsis promotes flowering and encodes a protein showing similarities to zinc finger transcription factors," Cell 80:847-855 Mar. 24, 1995.
Robson F; et al: "Functional importance of conserved domains in the flowering-time gene CONSTANS demonstrated by analysis of mutant alleles and transgenic plants," The Plant Journal 28(6):619-631, 2001.

(Continued)

*Primary Examiner* — Stuart F. Baum
(74) *Attorney, Agent, or Firm* — JHK Law; Joseph H. Kim

(57) ABSTRACT

The present invention relates to a flowering-time and/or stem elongation regulator isolated from rice, which is selected from OsMADS50, OsMADSS1, OsMADS56, OsMADS14, OsTRX1, OsVIN1, OsCOL4 and OsCOLS, a DNA construct containing the regulator, a transgenic plant, a part thereof, and plant cell transformed with the DNA construct, and method to control flowering-time and/or stem elongation using the regulator. In the present invention, the flowering-time and/or stem elongation can be controlled, and thereby, various agricultural benefits obtained.

2 Claims, 29 Drawing Sheets

(56) References Cited

OTHER PUBLICATIONS

Ledger S. et al: "Analysis of the function of two circadian-regulated CONSTANS-Like genes," The Plant Journal 26(1):15-22, 2001.

Hayama R: Yakoi S; Tamaki; S; Yano M; Shimamoto K: "Adaptation of photoperiodic control pathways produces short-day flowering in rice," Nature 422:719-722, 2003.

Nemoto Y; Kisaka M; Fuse T; Yano M, Ogihara Y: "Characterization and functional analysis of three wheat genes with homology to the CONSTANS flowering time gene in transgenic rice," The Plant Journal 36:82-93, 2003.

Database Genbank [online]. Accession No. AB003328, Aug. 26, 2010.

Sasaki T. et al., "Oryza sativa Japonica Group genomic DNA, Chromosome 2, BAC clone:OJ1476_F05", Database Genbank [online]. Accession No. AB004063, <http://www.ncbi.nim.nih.gov/nuccore/47497170?sat=OLD04&satkey=10616043>May 19, 2004 updated, [retrieved on Jan. 31, 2011].

Plant Protein expression & Purification Experiment, MARUZEN Co., Ltd. 1991, pp. 157-161.

* cited by examiner

FIG. 22 cDNA sequence of OsMADS50 cDNA
```
1   gttggttcat cggcgatcga agatggtgcg ggggaagacg cagatgaagc
51  ggatagagaa ccccacgagc cgccaggtca ccttctccaa gcgccgcaac
101 ggcctgctca agaaggcctt cgagctctcc gtcctctgcg acgccgaggt
151 cgcgctcatc gtcttctccc cgcgcggcaa gctctacgaa ttcgccagcg
201 ccagtacgca gaaaacaatt gaacgctata ggacgtatac aaaggaaaat
251 atcggcaaca agacagtaca gcaagatata gagcaagtaa agctgacgc
301 tgatggtttg gcaaagaaac ttgaagctct tgaaacttac aaaagaaaac
351 tgctgggtga aaagttggat gaatgttcta ttgaagaact gcatagcctg
401 gaggtcaagc tggagagaag cctcattagc atcaggggaa ggaagacaaa
451 gctgcttgag gagcaggttg ccaaactgag agagaaggag atgaagctgc
501 gcaaggacaa tgaagagtta cgcgaaaagt gtaagaatca gcctcccttg
551 tctgctcctt tgactgtccg ggccgaagat gagaacccgg accgtaacat
601 caacaccacc aacgacaaca tggatgtcga aactgagcta ttcatagggc
651 tgcctggcag aagtcgctcc agcggcggtg ctgcagaaga tagccaagcg
701 atgccccatt cttaagtaac aggccaggaa taagctggat ctct
```

FIG. 23 cDNA sequence of OsMADS51
```
atggcgcggaggggggagagtgcagctgaggcggatcgaggacaaggcgag
ccggcaggtgcggttctccaagaggagggcggggctgttcaagaaggcgt
tcgagctcgccctgctctgcgacgtggaggtggcgctcctcgtcttctcc
cccgtcggcaagctctacgagtactcctcctccagcattgaaggtaccta
tgatcgctatcagcaattcgctggagccaggagagacctgaacgaaggaa
gtacaagcatcaacagtgatgaaaatgcaagtatacactccaggcttagg
gacataacggcctggtctctccaaaacaatgctgacgagtcggatgctaa
tcagctagagaaactggagaaactgctgacaaatgctttgagggatacga
aatcaaagaagatgttggcaaaacaaaatggtgaagggagtaggagcaga
gcaaactccagtggctctaggggggcaggaggaaggaagtgcatga
```

FIG. 24 cDNA sequence of OsMADS56

```
atggtgcggggaggacggagctgaagcggattgagaacccgacgagccg
gcaggtgaccttctccaagcgccggaatggcctcctcaagaaggcgttcg
agctctccgtcctctgcgacgccgaggtcgccctcatcgtcttctccccc
cgcggccgcctctacgagttcgccagcgcccccagcctacagaaaaccat
cgaccgctataaagcatacacaaggatcatgtcaacaataagacaattc
aacaagatatccagcaagtcaaagatgatactttaggcttggccaagaaa
cttgaagctcttgatgagtccagacggaaaatattgggagaaaatttaga
aggatgctctattgaagaactgcgtggtctagaaatgaaacttgagaaga
gcctccacaacataagactaaagaagaccgagcttctggagcggcagata
gccaagctgaaagagaaggagcggactttgcttaaagacaacgaaaattt
acgcggaaagcatcgcaaccttgaggctgcggcgctggtggctaaccaca
tgacgacgacgacggcgccggcggcgtggccgcgggacgtgcctatgacg
agcagcacagccggcgccatggacgtggagactgatctgtacattggatt
gcccggcactgagcgctcctccaaccggtcggagacaggttga
```

FIG. 25 cDNA sequence of OsTRX1
ATGGTGATCGCGGTGGAGGGGGGCTTCGTGCACGAGGAGGAGGAGGTGGACCACC
CAATTCGCTACCTCCCACTTGGCCGCGTCTACTCCTCCTCTGCTCCGTGCCCTCTCCCCA
AGAAGCCCCGCTCCGCCGAGGACGGCAAGCCCCCGTGATCGTCTACTACCGCCGCCGCC
GTAAGAAGCCGCGGGTCGAGGGGCCACCTCCCTCGCCTGCCACAGCACCACCGATGCTGC
ACCCCCGGGAGGACGACGAGGATGAGGAGGTTACACGGCGGAAGGGTTCTCTCAAGTACG
AGCTGCTGAGCCTGGGGCAAGCCCCGCCCGCATTAGGCGGGATGGGGAGGAGCCCGCGC
GGCGGCGCTGCCTGAGGCGTAGCGGAGGGGCTGAGAGGAGGGGTTACTTCTCTGAACCCA
AGAGGCGGCAGCGGCAGGGCGTGCACAAGGAAGCTGCCTCCTCGGCTGGGAGGAGATGGT
TGGAGTTGGAAATTGAGGCTGCGGATCCACTGGCCTTTGTGGGATTAGGATGCAAGGTTT
TCTGGCCCCTCGATGAGGATTGGTACAAGGGTTCTATCACAGGGTACAATGAAGCGACTA
AGAAACATTCCGTAAAGTATGATGATGGCGAATCAGAGGACCTTAACCTAGCTGATGAAA
GGATAAAATTTTCTATTTCATCTGAAGAAATGAAGTGCAGGAACTTGAAATTTGGAATTT
CCAATCTGAACAAGAGGGGCTATGATGAGTTGCTTGCCCTTGCTGTTAGCCTTCATGATT
ACCAAGGTCTTGATCCAGGTGATCTTGTGTGGGCTAAACTTACAGGTCATGCCATGTGGC
CAGCTGTTGTGGTGGATGAATCAAATGTTCCTGCTAACAGGGCTTTGAAGCCAGGCCGAC
TAGATCAGTCGATACTTGTTCAATTCTTTGGTACTCATGATTTTGCCAGGATTAAGTTGA
AGCAAGCGGTGCCCTTTCTGAATGGCCTTCTTTCTTCTTTGCATCTTAAATGCAAGCAAG
CACGCTTCTATCGGAGTTTAGAAGAAGCCAAGGAGTTTCTCTGCACACAGCTTCTCCCAG
AAAATATGTTGCAACTACAGAAATCCATGGAAAAGGGCAGTTCTGATGCTAATTCCAATA
AAGATGTACATTCTTGTGACAATTTATCTGAAGATAAACAGCTGAAAGCGGAGGGGATT
ATGATGAGATGACTCCAATAGAACTAGGAAATCTTCGTGTGAGCAAATTAGGTAGGATAG
TAACTGACTCAGACTATTTCCATAACAAAAGCATATATGGCCTGAAGGGTATACTGCTT
TCAGGAAGTTCAGATCAGTGAAAGATCCACATGTAGTAATACTTTACAAAATGGAGGTAC
TGAGGAATTCAGATATAAAAGCTCGGCCATTGTTTAGGGTCACATCAGAAGATGGAACAC
AGATTGATGGCTCTACCCCAAATACATGTTGGAAGGAGATATATTGTAGATTAAAGGAAA
AACAGCGCAATGTGGCCTCTGGATTGGACAGAGATGTTTGTCAGGGATCTGGTTCCTATA
TGTTTGGCTTTTCAAATCCACAAATACGGCAACTTATTCAGGAGTTACCCAATGCAAGGT
CATGCTTAAAGTATTTTGAAAATGCTGGAGACACCTTTCGTGGGTATAGAGCTGTTCATG
TAAATTGGAAAGATCTAGACTATTGTAGTGTTTGTGATATGGATGAGGAATACGAAGACA
ATTTGTTCTTGCAATGTGATAAGTGCCGTATGATGGTACATGCTAGATGCTATGGTGAAC
TCGAACCATTGAATGGAGTCCTTTGGCTTTGCAACCTGTGTCGACCTGAGGCGCCTCGTG
TTTCTCCACGATGCTGTCTTTGTCCAGTAACAGGGGGCGCAATGAAACCAACAACAGATG
GTCGTTGGGCTCATCTTGCATGTGCTATATGGATTCCTGAAACTTGCTTAAAAGATGTGA
AGAGAATGGAACCGATTGATGGATTGAGCAGAATCAACAAGGACCGCTGGAAACTTCTAT
GCAGCATTTGCGGAGTTGCTTATGGAGCTTGCATACAGTGTTCTCATCCTACCTGTCGTG

FIG. 26

```
cDNA sequence of OsVIN2
atggatccacstartFcctacgcaggagtacctattgatcctgctaaatg
ccgattgatgagtgtggatgaaaagcgggaacttgtccgtgaattatcga
agcggccagaaagtgctcctgacaaactgcagtcttggagtcgccgtgaa
attgtagagattctttgtctgatttaggaagggaaaggaagtacactgg
attatcgaagcagagaatgttggaatatctcttcagagttgtgactggca
aatcatctggtggtggcgttgtggagcatgtgcaagagaaggagcctacc
cctgaacccaacacagccaaccatcagtccctgcgaaacggcagcgaaa
gagtgacaacccatcacgactaccaattgttgcaagcagtccaactacag
aaatacccaggccagcaagtaatgctcgcttctgccacaatttagcttgc
agagcgactcttaatccagaagataaattttgcagacgctgttcatgctg
tatttgtttcaagtacgatgacaataaggatcctagcctctggttattct
gtagttcagatcaacccttgcagaagattcttgtgtattttcgtgccat
cttgaatgtgctcttaaggatggaagaactggcatcatgcagagtgggca
gtgcaagaaacttgatggtggttattactgcactcgctgtcggaaacaga
atgatctgcttgggtcctggaagaaacaactggtgatagctaaagatgct
cgccggttggatgtattgtgtcatcggattttttttgagtcataagattct
tgtctccacggagaagtacttggttttgcatgaaattgttgacacagcga
tgaagaaactggaggctgaggttggtcctatatctggagttgcaaatatg
ggtcgtggaattgtgagccggcttgctgttggtgctgaagttcagaaact
ttgtgctcgagcaatagaaaccatggagtctctgttttgtggatctcctt
ctaacttgcaatttcaacgttcacggatgataccatcaaacttcgtaaag
tttgaagctataacccaaacatctgtcactgtagttttggatttgggtcc
tatacttgctcaagatgtaacatgctttaatgtatggcacagagtggcag
ccacaggctcgttctcatcaagtcaactggcatcatacttgcaccatta
aaaacgttagtggtcactcaacttgtgccagctacaagctatatattcaa
ggtagttgccttcagtaactacaaggagtttggatcgtgggaagccaaaa
tgaagacaagctgtcagaaggaagttgatctgaagggtttgatgccaggt
gggtctgggctagaccaaaacaatgggagcccaaaggcaaacagtggtgg
tcagtctgatccttcttcagaaggtgtggactcaaataataacactgcgg
tgtatgctgatctcaataaatcaccagaaagtgattttgaatattgtgaa
aatcctgagatacttgattcagacaaagcaagtcatcacccaatgaacc
tacaaacaactcacagagtatgccgatggtcgtagctagggttacggagg
tatctggattggaggaagctcctggactctcagcatcagctttggacgag
gagcccaattcagcagttcaaacacaattacttagagaatcctcaaattc
aatggagcagaaccagagaagcgaagttcctggatcacaggatgcatcaa
```

FIG. 27 cDNA sequence of OsCOL4 cDNA
ATGGAGGCGGTGGAGGACAAGGCGATGGTGGGAGTGGGAGGAGCGGTGGCGGCGGGGTACTCCTCGTCGT
CGTGGGGGTTGGGGACGCGGGCGTGCGACTCGTGCGGCGGGGAGGCGGCGCGGGCTCTACTGCCGCGCAGA
CGGGGCGTTCCTGTGCGCCCGGTGCGACGCGCGGGCGCACGGCGCCGGGTCGCGCCACGCGCGGGTGTGG
CTGTGCGAGGTGTGCGAGCACGCGCCCGCCGCCGTCACGTGCCGGGCGGACGCCGCGGCGCTGTGCGCCG
CCTGCGACGCCGACATCCACTCGGCGAACCCGCTCGCGCGCAGGCACGAGCGCCTCCCCGTCGCGCCCTT
CTTCGGCCCGCTCGCCGACGCGCGCAGCCCTTCACCTTCTCCCAGGCCGCCGCGGATGCCGCCGGGGCG
CGGGAGGAGGATGCGGACGATGACCGGAGCAACGAGGCCGAGGCGGCGTCGTGGCTTCTCCCCGAGCCCG
ACGACAATAGCCACGAGGATAGCGCCGCAGCCGCCGACGCGTTCTTCGCCGACACCGGCGCGTACCTGGG
CGTCGACCTGGACTTCGCCCGGTCCATGGACGGAATCAAGGCCATCGGGGTACCGGTCGCGCCGCCCGAG
CTGGACCTCACCGCCGGCAGCCTTTTCTACCCCGAACACTCCATGGCCCACAGCTTGTCGTCGTCGGAGG
TCGCGATCGTACCGGACGCGCTGTCGGCGGGCGCGGCGGCGCCGCCCATGGTGGTGGTGGTGGCGAGCAA
GGGGAAGGAGAGGGAGGCGCGGCTGATGCGGTACAGGGAGAAGCGCAAGAACCGGCGGTTCGACAAGACC
ATCCGGTACGCGTCCCGCAAGGCGTACGCCGAGACGCGGCCGCGCATCAAGGGCCGGTTCGCCAAGCGCA
CCGCCGACGCCGACGACGACGACGAGGCGCCATGCTCGCCGGCGTTCTCCGCCCTCGCCGCGTCGGACGG
CGTCGTGCCGTCGTTCTGA

FIG. 28 cDNA sequence of OsCOL8

ATGTCGGCGGCGTCGGGCGCCGCGTGCGGGGTGTGTGGGGGAGGGGTGGGGGAGTGCGGGTGCCTGCTGC
ATCAGCGGCGTGGGGGAGGCGGTGGTGGTGGAGGTGGAGGGGTGAGGTGCGGGATCGCGGCGGACCTGAA
CCGGGGGTTTCCGGCGATCTTTCAGGGGGTGGGGGTGGAGGAGACGGCGGTGGAAGGGGATGGAGGAGCC
CAGCCGGCGGCCGGGCTGCAGGAGTTCCAGTTCTTCGGCCACGACGACCACGACAGCGTCGCGTGGCTCT
TCAACGACCCGGCGCCGCCCGGCGGGACGGACCACCAGCTTCACCGCCAAACCGCGCCCATGGCGGTGGG
CAACGGCGCGGCGGCGGCGCAGCAGCGGCAGGCGTTCGACGCGTACGCGCAGTACCAGCCGGGGCACGGG
CTCACGTTCGACGTGCCGCTCACCCGAGGCGAGGCCGCCGCCGCGGTGCTCGAGGCCAGCCTCGGCCTCG
GCGGCGCCGGCGCCGGCGGCAGGAACCCGGCGACGTCGAGCAGCACAATCATGTCCTTCTGTGGGAGCAC
GTTCACTGACGCCGTGAGCTCCATCCCGAAAGATCACGCGGCGGCGGCGGCGGTCGTTGCCAACGGCGGC
CTGAGCGGCGGCGGCGGCGACCCGGCGATGGACCGGGAGGCGAAGGTGATGCGGTACAAGGAGAAGAGGA
AGCGGAGGCGATACGAGAAGCAGATCCGGTACGCCTCGCGCAAGGCCTACGCCGAGATGCGGCCGCGCGT
GAAGGGCCGCTTCGCCAAGGTGCCCGACGGCGAGCTGGACGGCGCGACACCGCCGCCGTCCTCCGCC
GCCGGCGGCGGCTACGAGCCCGGCCGGCTCGACCTCGGATGGTTCCGTTCGTAG

FIG. 29A genomic DNA sequence of OsMADS14 (red: exon)

GCTTCAGTTAATAAGATATATACTTGGTATTTTGCTTACATTTTCATTTTTTTCCCCTTGTCACAGCAA
ATTCCCCAAGCATAACATGTGAGTGTGACAACACAGTTCCTGTTCTCTTAGCTTATCTTGGATTCAATCC
CCTCATCCAAAATTAAATTCCATTTGTTCCCTATTCAGAGGGGAATTTCTCGGGGTATCTCTAGTATTT
AGCAACACTTTAATGTGTCCTATATATTCCCTTGGTTCATCCCCTATAGTCATTTCCCATGATTCTCTGT
TCCCTTGGGTCCACTATGTACAGGTATTGCACATATAAATCATGAAACTACCAAATGCATTGGCAATTGC
AAGTTGATGTACAACTATAGAAGTGTGTTTATTTGGGGATGAAGTGGGATATGTTAGGTCCATCCTTATT

FIG. 29B

```
TTCTGAGATGGGATAGCCCCATCTATGTCTTTGGCATAAGGGATATAATGCTCTTATTTTTTTATAAGG
AATGTGAGGGTGTGGCCCGCATCTCAATTCGAGTCCGTTAATTTTTTTCATATAAAGTTGACCTGGATCT
AGAAAAATATTCCATTTCAAGGATTATTCTGTCCCACCTGTTATCGAACCGAACACCCTGAAAATAGATT
TGTCCCCACATGACTATCTCATCCCTTTCAACCAAATACATTATAACTTATTGACGGTTCTGCAGCTCTG
GCTCGTTTCGGAAAAGAGCTATGATGGAGGCTCGGGCTCAGCTAATTTGGCTTACAAGCTGAGCTGAGCT
TTTTGTCCTCACCTAGTTCTGCCCATGGGGAATCTAACATTATCAATCATACACCATATCTTAAAGAGAT
GCTGCTATGATACGTCAAGAAGTCAAGTTTTAAGGTAGAATATATGGTAGTTGGGAAAATAGAATCATTA
CATAAATGTTAGAAAATAGGGATGCCAACGCGACATGCTTGCAGGCTTTGAGGCCCAGTAAACCTAATTG
TACTTTTTTTTCATCCATTTTTATTATATACTTGTTGATGAAAATTAACTTAGAATATGGGCTCTTATGT
AAGATAGCATCGCCTGCATCCTTACAAAGAGACAGATAGATCCAATCGTACAATTAAATCAGTAATTTTA
TAAGAGAATGAAATAACATTCTAGCTAGTGTATCCAAGAATGCACAGTGAAGTCCGTATTTAAGTCCCAT
CCAAAACGATGTGATGTTAGATCTGATCCAAAATATTTAATAATGTAGCTCAAGTTTTGCATAGCCCCTG
AGAACCAGACAAGCCAATGTTAAAATTCCTACTGTGCATAGGGAGGGCAATCAATCATCCTACTGCATGA
GTAGGTCCCTGCTTCCTGTTCAAAATACTTTCTCCGTTCTACGAAGACTACATTTTTAGAACAAAGCTAA
CAAACTAATGGTGAGAGAAGAAAAATCAAATGAACACTCATTAATACGAAAATAAATTATCGTCAAATGA
TAACCTAGGAATAATTTTGAGTTACAGATTAATTATAGGTAAGAAAGAACAAAGTTAAAGCGATCGAAAA
TGAAGTCTATTTAAGGACCAGTTTAGTATGGCTCTAGCTATAGCTCCACTCATTCTATAGCTGGAGTCCA
ACCAAATAGTTTCTACACCTAAAATAGAAATATAGTTGGCTAGAGCGTTATCACAAAATAAACTAGAGAG
GTGGAGTTGAGTTCAGACCGCTACACAACTTCACTTTAAACTTTAACTCCTAAAGTTAAATTTTAAGAGA
TGAAGATCTACTAAACAGGCTTTAATACGGAGGAAATGCATTCATCCACAAAGGTCAAAAGCAGCAGAAA
GAGAACGAATGCCTTTGCTGCATTCAACCCCAAGCAGAGCTGCAGGGGTGCCAACTGCCAATCAGGCAAT
CATCCACTCTGGGAGCGACAGGCGACGCCATTGATGGGCACACCCCCTCGCCGGGGCCGACGGGAGACGA
GACGACGCAGGCACTGTTTTGCGGCCGACCCAAGCCAAGCCAAGCCAGGAGCCATCCCGTCCCATCACGA
CGCATTGCTGCCGCGGCCTAATTGGGCAGGAAAAGCCATGGCCCACCCCACCGCCTGGCCAGACGAGAC
GGCCCAAAAAAGGATCGGCCCAGAAAAGCCCACGAGAGTACGACGCACGCACGCGTCGCCGGGAGGCGGG
GCCGGGCCGGCGCCGCCTCGCCCAATGGCCGTTCGACAGCGGAGGCGATCGAAACCACCCCGGTATCGC
CAAACCGCCTCCTCCTCCTCCGACGATCCGGCGCGCGCTCCCTTTAAAATCCCCCCATTTCCTCCTCCTC
CTCCTCCTCGTCGTCGTCGTCTCCCCCACTCGATCGATCCATCCATCGATCGATCGGTCCCCCCCATCGC
GCGCGACGCATTCCGCCGCCGTCTCGCCGTGTCCACGTGATGGGGCCGGGGCTAGGGGATAGGCGGATA
GCCAGCAGCCACCACCACCAGTAGTTGCCGTGTGGGGATAGGTGTGGCTATAGGGCTAGTGGTCGTCGCT
GATAGCGAGGTGGGTAGGGTTAATTTTGGTTGGAGGTAGAGAGAGAGAGAGAGGGAGGGAGGGAGGAGGA
GGAGGAGGAGGAGGAGGAGGAAGAACAGGAGGAAGATGGGCGGGGCAAGGTGCAGCTGAAGCGGATCGA
GAACAAGATCAACCGGCAGGTGACCTTCTCCAAGCGCAGGTCGGGGCTGCTCAAGAAGGCGAATGAGATC
TCCGTGCTCTGCGACGCCGAGGTGCGCTCATCATCTTCTCCACCAAGGGCAAGCTCTACGAGTACGCCA
CCGACTCATGGTACGTACGTACGTACGTGTGCTTGATTAAATTTCATCCTCATCGCTTGTCTCTAAGCTT
TCAGTTCTTTTCGCTTAATCGAGCAATCCTTGCGCTACATGATGTGTTCCCGTTTCCGTTCTGTTCGTAT
```

FIG. 29C

```
CGATCGATTGCCTTTGAATTCTGTGTGTGATTAATTCGATCTGTCCTGATTGCTCGAATTAATTTTGTTG
CGTGTGTTTCGGGGTTATCCCCAATAATCTGTTTGAATTTCTGCTGCGATTGTTGATTGCTTGCCGGCGA
TGGAGGAGGCAGCGTGTTTTGCTATTTCAGGCTTTGAGCTGACGGCGTGAGGTGAGATGCGTTGCATCTG
TGCACTGTAGCTACAGTGCCCGTACGAGGGTAATTTTATGCTCCGCTTTCGCTGGAGAGGGCGTTGCTGC
TGCGCTATTTGGGGAATTTTTTTTGGCCCTGCCGATGGGTGCTGCTTGCTTGGCGACAAGCTAGCTTTG
CACCCAAAGGGGAGAGGGGTGATTAGCTAGGAACTCTAGTACGTAGATTTGATGGACCTGGGATTATTTG
GGGATTAAAATGGTCTTGGCTTGTGTTCATCTAAAATTCTACTGAACTTGCTGCTTGTGTTGTGTGTGCC
TCTTCTTTCTTCACTATTCCCCATATTAATTCTGGGCTCGTTTAGATCTTCTTTCTCTCTCCCTGGCCAT
CTCTTTCTCTTGAGGCAACTAAGCATATTAAGGGAGAAGATGAAACGGGATGCATCGGGAGATGGAGGAG
TTCATATCTTAAGCTGCTGGTGACTTGTTGGAACCCTTTTCGCTGGTTCGTCTGCCTCTAGCTTTCTTGG
ACTCTTTGCTGATGCATGCCATGCTTTTCAGAACGAAAAGATTTTACTAGAACAAACTTATAAGCTAGGG
CTGGCCTTTAATCTTTACTTCTTAATTCCCGGCTGTCATTAGTTCAATCTAATGGTTCATTAGTTGCTGG
GTTCTACCTTTCCTATAAGGTTCTTTTTGAGATGTACATGGTTTCTGAAGAAACATCCATGCTTCTAGCT
AGCCTGATTACAGACTGGTTTCATGCTGCTTCTTTTTATCGAAAAGTCACCTTGGGGGAGAGTTTCCCA
CTTAACTCATTCGATTTCTTAGTTCAGAGGGGAGGTACAAAGGTTACAACATTACATCGGAGGTCTGTT
AAGATGTTAAGACTTAGTAAGAGGTAGAGAGGAGTTAACAGGAAAAAAAAGAACTTATAAGCTAAAGGTT
CATCCTAGTTAGCGCTTTAGTTGCTGGGTTCTACCTTTTCTGTCAGGTTCTTCTTGGGATGTGCATATGG
TTCCTGAAGAAACAGACATTAGAAATTTAGAACTAAGAAGCAAAACGTTGGATGCTTCCAGTATACCATA
TCATCTGAAGGATATTTATCCTTCTTGATGTTTTCGACAATGATTTACTATTAATGCATTGTTATGCAAG
CTTTGTTAAGTCAACATGCAAATCTTAGAGTTTGATGGTTAATTCCAGTTCTTATATATTTTTAAGTTA
AAAATTTTCTTATCTCTCCTTTTCCTCACTACATACGAATAGAGTTTGATCTGGCTGTTATAAATTTTC
TTCAGTTTTGTGGGCATCCTTATATCTACTAATCAGACTCCCCATATGATCAGTGATTATCAGCTTATAC
TCTATTCTAATTCTATGAATGAACGACTAATTAACTTAATTAACTCCTCGCTGATTTAATCCAATAAGGG
TAGTGTGTTGGGCATCCCCATAATGCTAGCAACCACATCTCTAGATAAGAGTCATTAGTATCACATATTT
TGAAATCCTTCTCACTCTAACCATTGATCAGTGAGTTAAGACATAGGAGTAGAGCTTCACGTGAGGTAAC
AGTGTTTGGATTTCAAGGTATCAAGTTTGGGGTGGGAGTACACGAGCCGATGGATTAATCTGATTTTTTT
TTCGTTTCTCGTACGTCATTAAACGTCTTATTTGGAAATCAACTCCATTAGGTTCCTGCAGGGTACTGTA
GTTATGCTAATTAATCCTTCTTAAGACTTTTCCAAGATTTAGCTTTAAACAGATGCTTTCATGAACCTAG
TTGGGAAACATGACAAATCCTCTTCGAACTTTAATTAAGATGTTACTTTAATTAGCATGCCTTAAGCTGG
CATACGTAGCGGCAAATGCAACCACTTACAATTCATCACAAGGCAATAGATCGACTGGCTTTCTTGTTAA
AGCTAAGCAAGTAGTTACCTACTGCGCCAATAAGAATATTGAGCCTACTCCATTGGTACGATGGGTAATA
TTTATAAATGCTTGTCGTTTAGGAGTAGCAAGACACTAGTTCTTTCATATTTGTTTGGGTGCCAATTTAG
AAAACTCTCCGTACTTCAAATGTAGTAAAATACTCTCCTACTGCTCTTTGGACGATGAACGTCTACACAG
ACAAACAGTAGTCATATTTGAAGTGACTCGGGAGATATTTTAATTCTTTTTAACTATAAGCAGTAGAATT
GTAAAGTTGGTTTCCTCCATCTTAATCCAATGCACGAAGTTCAGAACTCTGCTTTGATTAATAGAGCTCG
CAGCGACTTGCATGCTGTTTTCACAACAAGACTCTTGTAGTATTGCATCTAGCCGTATATAGATGAGTCG
```

FIG. 29D

```
GCAATGAGTTAACTCTGGCTCTCACTGTCTCACACGCTATTAGGGTTCCAGACTTCCAGTCTACTTGATT
CAGAAAAATACAAATATTCTCTTATAAGTTAGCCCAAAATAATAAAATGGATATATATTTGCGGGCATTA
ATTGGTCTAACTATGCTCGGAGGCCTACTGGTCCAACTCGCGTAGGACATACAAACTCATAACCGCATAA
TATACCTGTTCAGCTATTTGGTTATACAGTATTGAGTTGATTCCTGCTGTTGACTGAACTGTAGCAACGT
CTGTATATATCCGGGACTAATGATAAATTTTCAGTTTGGATTGCATTATTCACAATATCTTTTAAGCATT
AATACTGTATTAATTCTCTTGACACTTCATTTTGTAATAATTTTGTTAATTTTCCATAGGTTGATTAAT
TTCAAGTTATCCTATATACTTATATAGTTCATCTCCACTAAGTGTAGTTAATGATATTTCTCTCCTCTTA
TTAGACTACATTACCCCAATTATTTCTAGCCATTGGATAATAGATATATGGTTCAAATTTTCTCTTCTTT
CTTCTCTCATTACACCAAGTAATCTCAATCATTTTTAGGCCTTAAACTCATAAGTATCAATTTGTTTTAG
TTTTAATATTCATATTTCATCTTATTTGTACATATTATGCAACTTAATTTCCCGCAGCAACGCGGCAGAG
TATTCATTTAGTTAATGTAGACAACCCAATATCACATGTGATCTTACTTGATTATCATTGATTAGACCCT
GTCTAGGAATAAGAAGCAAATATGTTCTCTTTCAACAAAGTTATGTTTGCTTAAGAGTCTAGGGTGTTGT
ATTTCCCCTTAATTCTTTCTATAGATAGTTATACTTGCTATCCTGTTTCATTTCTTTTCTTAACGAAAA
TGAGATACAGTTCAGTTGCTTAAGCTTTTCTTGACATGTATGCTTGTATTACATGTTTACCTTGACTTTG
CCCCAGAAGTATACCTTCTATATATATGCATATTATCTTTCCCCAAAAGGTTATACAGACCCTTTTGAAA
GGTTGACATTTTAGTATGCCGTAGAAAGTATATATCCTTTGGTTATAAAGTGAACTTGTTCAAAGTGCCT
CAAGAACATGGAAATACTTTAGCAAACAATGAAGCTACTCCCTCCATTTATAATTCATTTCATATTATAA
GTTACTTTGAATTTATTTCCTAGTCAAACTATTTTAAGTTCGACTAAATTTATAGAAAAAAATAAAAATA
TTTCTAACACAAAATAAACATTTTATCAAATATGTTCAATATTAAATTTAACGAAACTAATTTGGTATTG
TTGATGTTGCTATTTTTTTCTATAAATTGGTCAAATGTAAAGATGCTTGACTTGGGAAAAAGTCAAAAC
GACTTGTAATATGAAACGGATGGAGTAAGACTTAATAATGTTTCAGAACTTGAACCATATCAGTGCTACC
ACCAAAAGCTGATCATTCTGATATATGAAAATGTTTATTGTTAGCTTTGCCCAAAAAACCGTTTTCATGA
ACTGCATAAATACAACAATTTATTGTTTTTTAGGGTTCTGTGTGTGGGGGGTGGTGTGTTAATCCAAC
TCTTGTGTTAGAAGTAGATTGGCAAATCTATTCTGTATTATATCTTACATAAGTTCTTATAAGAATAAAC
TGCAAAATGTAGGTGTTGTTATTTACACCACTACGAAGTACCCCCATTTAAATTTTGAATGTATAACACC
GTTGACTTTTATACATATGTTTGACCGTTCGTCTTATTAAAAAATACGTAATTGTCATTTATTTTGTTGT
GATGTGTTTTAAGCATCAAAGGTAGTTTAAGCATGACTTTTTTTACATAATTGCAAAAAGAATTTGAA
TAAAACAAATGGCATTTTATTATGGGTTACGCATTTACATGTCATAATATCCACTGTGACATTTGAGAAA
CCTATTCATGTTTTGAACTAGAGATTATTAGTAGTTGAGGGCCTTTGTTAGATGCTGCTAGTCCTATGAT
TTTGGTTAGTACATGTATGGCAAGTGAAATCGTATTGATATTATATTCCCACACAATATGTAAGTTACTT
CAACACATAAATATATAACAATATCTAGTTTTGTATTACTTATATATATATATTCTCATCATAGTGATAG
TCACTAACTTACCTATTAAGACATTCAAAGAAATGGGCATCCTTCAGTTAGGATGTTACAGTGATACACC
TTTTCGTTTTGACAATACTGCATACGCAGTTTCTAAAACAACTCCATGTTAAAACATAAGGGGTTGCACT
CAAGTAGATTTTGAAGTGTGTGTGCGCGCCTGTGCAACTTTCTTGTTCTTCCTTCGTTTTATTTTAAACC
TGGAAACTAAAGTAGGTTTCCTGTTAAATTCCTATCCTTTCTTAAAAAAATGGACTTCAAGAAAAACAG
ACCAGAATCATAAATACAGTGTATGTATCTGACCTGTATATGAAAAGGTACAGCCATATGTGCATTTGTT
GTTGAGATGGAAGAATATATATACTGCTTAGTTATTATTACAATTATTTCAAATGATGAAACGTATATTC
```

FIG. 29E

```
CTCATTTTTCACAGTATGGACAAAATCCTTGAACGTTATGAGCGCTACTCCTATGCAGAAAAGGTCCTTA
TTTCAGCTGAATCTGACACTCAGGTAAAAATAAAGAGCTCTAATTCTGTTGTTTCTCATATCTCAATATC
TTGTTTATTTTTGAACTTTTCACTACACCTGTTTCGGTTGACTCATTCAAGACGGGTACATCCAACATT
TTAGCTCTCCTCAAGTTGGATAAATCAATTAGGCATCATTTTTTATGGCAATTTTCCATTGTTATGTAGA
TCAACTTTTAATAAATATTGCTTTACATCTCTTTGAACAGTAATCTCTTACTTCAATGTACTTATCAAAT
ATGTAGATTTATTCTAAATTAGATTATATCCATTTTTTATTACATAGCGTCCTGACCTTTTGGCATCCCA
GCCCAATTGAACCTATTTGCTGTCTGAAATCTTGAAAACTCAAACTGAACTGTTCTTTATATTGGTGCAA
TTAATTAGGCTCTCTCTCTCAGGTCAGATCATTAAAAATTGTGGTATTGTTACATTTCATAAGTGAAATT
TTGTTCACAAATTAGATCAAATTTATCTTCCATGTTTGTTTACACGTATACAGCTTTGCCAGTTCCCTCT
TATTCAAACATTTTTTACACTATGATTCAATATACCTTTTGTGGATTTTACTGGAACAAAATCATAGTTA
TTGCCTAATGAAAAACTATAAAAAAAAATTTTGGATGCATGACTACATCAACACTCATTATGGAATTTTG
TGTGCCAGAGAATATCACAAAACATATTTTTCATCAAATAAAACAAAATAAACATTTTCCAGAACTTTTG
GCGTGGCTCATCAGAAGTTTGGAACCTTAAATAATCCTTGTTTTCATTTAGCTGGGACTTACTATAGTCA
ATTATGCTATTAAAAAGATCCATTCGTCTATTTGTTACGAATAATCTTTACTCTTTAGTTGGGGTTGATG
GACTAATGGTGTACTCCAAAATCAGAAGTTCTTTTATGGCTAGATACATGTAGACCGGATTTGAAAACTT
TCAAGTTTAGATTTGACAAAAACTTTCAACTCGCGATTGAAAATTTTCAAGTCCACATTTGAAAACTTTC
AAGTTTAGATTTGAAAACTTTCGACCCAGATTTGAAAACTTTCAACTCGAGATTTGAAAACTTTCAAGCC
TAGATTTAAAAACTTTCAAGTTCAGATTGAAAAACTTTCAAGTTAAGATTTGAAAATTTTCAGCTCAAAT
ATTTTTGAAAACACGTATCCTAACAATTAAAAAAATCAGAAAAAACACGAAAGAATAGCGAAAAAAAGAA
AAAAACGAAAAAGATGGAAAAAAAGGAAACACAAAAAAAAAGGAAAAAAATCGCGTGGGACCGCCAGCTG
GCGCGCGCGCCAGTTCCGTAACTGACTTGCGCTCGCCAATTAGCATCCCCATGTAGACATGCATATTCT
TCGTTTGCAATATTTTTTGTAAGAAGTTGCTGTGTATGAACATTGTTGACTGAACTAATGTAGTTATTAT
GCAGACAGTGGTAAGTCATATTTCCATACCATAAAGAGTGAGACTGAGAATTTTCTAATCAAGATATTAC
AAAAAGCTGAACTAGCTAGGCAGACTGTAACCCTGTTATCATTCCTAGAAATGTTTGCTACTTTGGAGAT
AGTAGATAATATAGTTATCACGCTGATGAATTGTCAAGGAAACATACATTATAGTTCCCTTTCCTAACAT
GCACTATCTGCTTAGAGCTTTTCTCTATATAGATTTGGATGGCACTATTGTATACTCTTCAGCACATTC
AATTTCTAAACTTGTAATATTAGTGATTCTGTGCTTAGAATTGTGGAGGTCACTGTACATCCACCAGTAA
ATTTAGTTTGATGAGTGTCGAGAAGAAAAGGTAAGTGTGGAGTGGGGACAAAGTTAATCATATTTTACT
GCAAGCACACTGAAGTAAATCCATTTATTCAATATACACTGTACCTAAGCAATTCTCCACGGAGGTATCT
TGCAGTTCTAGGTGTCCACAGTTTTAGCTATATGCAGTGCCAAAATCGATTAAAGTTACACTTGTTAATA
TAGAAATTCAAGGTACTCCAAAGGGCACAATCATTTGCACAATCAGTTCTTCCTGGCAATTTTTCAAATA
TCAGCTAATGTATGAATAGTATTGTGATACTTCCTATTTACTCAAATTTATTAATGTAAATCTTCTATGC
TTGCTTGTATAGGGCAACTGGTGCCACGAATATAGGAAACTGAAGGCTAAGGTTGAGACAATACAGAAAT
GTCAAAAGTAATTGGAAACTACTCACAACTGGTGCCATTATGACATTATGTACTATACACTGTTGACATA
```

FIG. 29F

```
AAATTGTTCGCCTTAAATCCTGCAGGCACCTCATGGGAGAGGATCTTGAATCTTTGAATCTCAAAGAGCT
GCAGCAGCTGGAGCAGCAGCTGGAAAATTCGTTGAAACATATCAGATCCAGAAAGGTGGTTTTTGTGATG
AGAATTATTCAAGGCTGATATCAACAATATGTGCAAAATTTATATGGTTTTTATACAGCTAAATATAGAT
GTCCTGTATGTTTTACGAGCTGACAATTACAAATCTCCTTTATGTGCAGAGCCAACTAATGCTCGAGTCC
ATTAACGAGCTTCAACGGAAGGTAATGATGTCAACCATGTTAGACCTTTAATTGAGTACTGGGACTTGCT
AGAAATAACCTTGTCAAAACTCGAGAAATCTTTGGCCGGCCACCAGTTGATACCATCGCGTGTTATGTTT
CATACTCTTATTTTAAGTTCCCGCCATGCTTGCAACTGCAAGTGCTGCCACACTTTCATTTTCTAACATG
CACGCCGGATTCTTGCTGCAGGAAAAGTCACTGCAGGAGGAGAATAAGGTCCTACAGAAAGAAGTAGGCT
GCTAGCCTTGATGCCCCCTAGTTTCCATGCTTCAGCTGATCTTGGTTTGTTTAACATCAATCAAGTTAAA
TTGACAGAACCCTTGCTCCTTCCTACAGCTGGTGGAGAAGCAGAAAGTCCAGAAGCAACAAGTGCAATGG
GACCAGACACAACCTCAAACAAGTTCCTCATCATCCTCCTTCATGATGAGGGAAGCCCTTCCAACAACTA
ATATCAGGTAAGTAACTAGCAGCCTGAAGTTAGTTTCGTCCTTATGTAGCACAGACGAATAACCTTTTGG
ACTAAAGATCATTAGATCCAGCTTTATTAGAAAACAAAATTAAATGGCTCGTTTAGTTCACTACCATATC
AAAATATTGACGATACTAAAACCTAGACAAATATTGGAAGTGCTACATTTTTTTGTCAACTTATATATGT
TATCACTATATTTTAATAGCAAATCAAACATTAGCTAAAATACTATTAAAAATACCAACAACTTAATAGG
GGCATATTTTGGCACCAACCACCAAACAACTGAAAGTTCTAACAAGGTTGTATAAACCAATAACTATCAA
ACCTTTTTTAGGCACCTCAGAATTTTACGCTTTTTTTTGTCTGAAAACACGCCAAATCTGCCCCTTTTCC
CCCAAAACGCCAGCGGGCTTTTTCTTGTCATTTTGGTTGGTGATGTAGCTAAGAGGTGTGCTTATTCGTT
CCACAGTAACTACCCTGCAGCAGCTGGCGAAAGGATAGAGGATGTAGCAGCAGGGCAGCCACAGCATGTT
CGCATTGGGCTGCCACCATGGATGCTGAGCCACATCAACGGCTAAGGAGGCTTCAGATCCATACCAGTAA
TCACAAGTTGCAACCTGACCCGGTCGGTCGCCTGCTGCTCTGGTTTACTACTAGTACTATTGTCATCTT
GCGGTTGCGAGACGAGGAAAGCATTTTAGCCCTAAATTCAGCATTAGTAGCAAGCTGCAATGTGTATATT
TTGGCTTCGTCCAGCACCGTCTTCCTCCCACCAGTAATTTACCCATGTAATATATGCGAGTAGCATGAAC
AAATTTTCCCGTTTCCAACCATCTCCATTGGTGTCATGTGTGACTTAAATAGCGAAATTTCAGCATTGTG
CATAGTGTGATTACTGTAAGATAAATAAACTTTGTAGACAATAAGTCTCCGTTATCTTGCTGATTGGAGC
TGAATCTGTCCGATCACCGGCAGAGCTGATTGAGCGCATACTGCATAACGAATAAATTGTATGCGAACAA
GTTGATAGGCATAAATCGTTCGACTGTTTACAAAGAAAATAAGGCGTGACATTCTCAGTTAAATAATGGG
AGATCATCTTGTATATAATGATCTTCTGCCGTCACTCCTATACAAACATTTTACCCATTACAAAAACCAA
GAAATATACCAAGGCGCCCAAGCTCACTGTCACTGCTGACTCCCCTACCACTAAAAATTCTCAAGGAGG
ATAACGAATGCTAAGCATTAGTCTTCTAAGAATGGCATTCAGAACTGTGGAACTATGTGCCGGCTGATGA
GAACTCAGCCTATGAATAAATTAATCTAGCCACAACTTTAACATAAAGATATTGGTCAGAGGTTGTATTT
AACTGAACAGGGATATGCTAGTATTAAACTCGAAGCATCTTCTCTTTCAGGCGTGAAATGAACTTGAATG
TCTCCTCTGCTTTGACCTGTTGATACATATCACTTCTTGATACTCTGTCCGGATGGAATTTCAAAAGAGC
TTGCTTGTAAGCAGCTTTAACCTGAAAAAAGTTTCATATTAAACAATTGTCAGCGGGAAGAGATCAATAA
TTCCTTATTTACATTTATGGGTATCATTTTATGAACTTATATCAGAACATGGCATAAGGTGGTAATTGAT
CTCGCCTAGATTGCCAGAGGCAATAATTGGCAAATCTTCCAAAATTTGTCATGAGAAGCTATCTCTTCTA
TAAATAAACAAACGAATTTGGGATTTCTCCATAGAAAATTGAAATACAAT
```

FIG. 30A cDNA sequence of OsMADS14

```
atgggggccggggctaggggataggcggatagccagcagccaccaccaccagtagttgc
cgtgtggggataggtgtggctatagggctagtggtcgtcgctgatagcgaggtgggtag
ggttaattttggttggaggtagagagagagagagagggaggggaggaggaggaggagga
ggaggaggaggaggaagaacaggaggaagatggggcggggcaaggtgcagctgaagcgg
atcgagaacaagatcaaccggcaggtgaccttctccaagcgcaggtcaaaactgctcaa
gaaggcgaatgagatctccgtgctctgcgacgccgaggtcgcgctcatcatcttctcca
ccaagggcaagctctacgagtacgccaccgactcatgtatggacaaaatccttgaacgt
tatgagcgctactcctatgcagaaaaggtccttatttcagctgaatctgacactcaggg
caactggtgccacgaatataggaaactgaaggctaaggttgagacaatacagaaatgtc
aaaagcacctcatgggagaggatcttgaatctttgaatctcaaagagctgcagcagctg
gagcagcagctggaaaattcgttgaaacatatcagatccagaaagagccaactaatgct
cgagtccattaacgagcttcaacggaaggaaaagtcactgcaggaggagaataaggtcc
tacagaaagaactggtggagaagcagaaagtccagaagcaacaagtgcaatgggaccag
acacaacctcaaacaagttcctcatcatcctccttcatgatgagggaagcccttccaac
aactaatatcagtaactaccctgcagcagctggcgaaaggatagaggatgtagcagcag
ggcagccacagcatgaacgcattgggctgccaccatggatgctgagccacatcaacggc
taa
```

FIG. 30B

```
cDNA sequence of truncated OsMADS14
atggggcggggcaaggtgcagctgaagcggatcgagaacaagatcaaccggcaggtgac
cttctccaagcgcaggtcaaaactgctcaagaaggcgaatgagatctccgtgctctgcg
acgccgaggtcgcgctcatcatcttctccaccaagggcaagctctacgagtacgccacc
gactcatgtatggacaaaatccttgaacgttatgagcgctactcctatgcagaaaaggt
ccttatttcagctgaatctgacactcagggcaactggtgccacgaatataggaaactga
aggctaaggttgagacaatacagaaatgtcaaaagcacctcatgggagaggatcttgaa
tctttgaatctcaaagagctgcagcagctggagcagcagctggaaaattcgttgaaaca
tatcagatccagaagagccaactaatgctcgagtccattaacgagcttcaacggaagg
aaaagtcactgcaggaggagaataaggtcctacagaagaactggtggagaagcagaaa
gtccagtaa
```

REGULATOR FOR FLOWERING TIME, TRANSGENIC PLANT TRANSFORMED WITH THE SAME, AND METHOD FOR REGULATING FLOWERING TIME

The present application is a continuation of PCT Application No. PCT/KR2005/004461 filed on Dec. 22, 2005, which claims the benefit of priority to U.S. Provisional Patent Application No. 60/638,460, filed on Dec. 22, 2004.

FIELD OF THE INVENTION

The present invention relates to a regulator for flowering-time and/or internodes elongation, a transgenic plant transformed with the regulator, and a method to regulate flowering-time and/or stein elongation in plant.

BACKGROUND OF THE INVENTION

The growth phase of plants generally includes a vegetative growth phase and a reproductive growth phase. The transition from vegetative to reproductive growth is affected by various flowering signals. The flowering signals are affected by various factors, such as genetic factors such as genotype, and environmental factors such as photoperiod and light intensity, etc. (Dung et al., 1998; Yamamoto et al., 1998). The transition in the growth phase leads to various morphological changes of plant, which is interesting from a scientific viewpoint. Furthermore, due to the economic benefits gained by flowering regulation, many studies on flowering mechanisms have been carried out.

In particular, molecular genetic studies of *Arabidopsis* (hereafter, *Arabidopsis*) have shown the functions of the flowering regulatory genes and their interrelationships, elucidating the signaling pathway of flowering. In *Arabidopsis*, the flowering is affected by external signals, such as light, temperature, photoperiod, etc., and internal signals such as nutritive conditions, hormones, etc. The flowering pathway generally includes the photoperiod-dependent pathway, the vernalization-dependent pathway, the GA (gibberellin)-dependent pathway, and the endogenous pathway.

In rice, it has been reported that flowering-time is mainly controlled by the photoperiod-dependent pathway and the endogenous pathway (Yamamoto et al., 1998). Recently, several genes which are thought to be involved in the photoperiod-dependent pathway in rice have been isolated and identified, characterizing the photoperiod-dependent pathway to some degree. (Yano et al., 2001 Mouradov et al., 2002). Firstly, several specific gene loci which are involved in controlling photoperiod sensitivity, such as Se (Photoperiodic sensitivity)1 (Se1), Se3-Se7, and EE1-E3, have been identified (Poonyarit et al., 1989; Sano, 1992; Tsai, 1995; Yokoo et al., 1980; Yokoo and Okuno, 1993). (Furthermore, by quantitative trait loci (QTL) analyses using molecular level markers, several tens of gene loci involved in controlling heading date, such as Heading date 1 (Hd1), Heading date 6 (Hd6), Heading date 3a (Hd3a), etc., have been detected (Li et al., 1995; Lin et al., 1996, 1998; Maheswaran et al., 2000; Yano et al., 1997; Xiao et al., 1995). Among the above genes, Se5, Hd1, Hd6 and Hd3a are counterparts of LONG HYPOCOTYL 1 (HY1), CONSTANS (CO), CASEIN KINASE 2 (CK2) and FLOWERING LOCUS T (FT) of *Arabidopsis*, respectively, and they are expected to have biochemical functions similar to the counterparts in *Arabidopsis*.

However, in some cases, the above genes of rice and *Arabidopsis* show different responses to photoperiod. CO of *Arabidopsis* is a gene which is involved in long-day (LD) promotion pathway to activate flowering. There are orthologs of CONSTANS in rice, and among them, Hd1 (Heading date1) gene regulates the flowering-time. Hd1 gene of rice, which encodes a protein containing a zinc finger domain and a nuclear localization signal, increases expression of Hd3a gene to activate flowering under short-day (SD) conditions, whereas it decreases expression of Hd3a gene to inhibit flowering under LD conditions (Izawa et al., 2002). In *Arabidopsis*, the CO gene, which is an ortholog of Hd1 of rice, increases expression of the FT gene (an ortholog of Hd3a of rice) to activate flowering under long-day conditions. However, the CO does not act as a flowering inhibitor under short-day conditions (Putterill et al., 1995). The molecular level understanding of such different photoperiod reactions depending on plant species is expected to provide a clue for understanding the differences between LD plants and SD plants.

Although flowering-relating genes such as the above have been discovered, they are few in number. Furthermore, rice-specific genes distinguished from *Arabidopsis* genes have been mostly unknown, and long-day specific flowering regulators and regulators for controlling the endogenous pathway which is different from the photoperiod pathway also have been mostly unknown. Considering that flowering-time is a key trait in determining cropping season and regional adaptability, and that significant agricultural profit can be obtained by controlling flowering-time, it is necessary to elucidate the flowering-time regulating pathway in rice and to find the genes involved in the pathway.

The present inventors identified useful flowering regulators in rice and investigated the characteristics thereof, to achieve the present invention. In the present invention, previously unknown flowering regulators have been, found, as well as the fact that their functions are specifically differentiated in rice.

DETAILED DESCRIPTION OF THE ILLUSTRATED EMBODIMENTS

The object of the present invention is to find the genes involved in regulating flowering-time in rice, and their working conditions, for agricultural benefit.

To achieve this object, the present inventors screened rice mutant lines exhibiting early- or late-flowering phenotype from T-DNA-inserted lines of rice, and analyzed genotypes of the screened mutant lines, to isolate flowering-time regulators of rice including the counterparts of flowering-time regulators of *Arabidopsis*, such AGL20, CONSTANS, etc., and elucidated the functions and working conditions of the isolated regulators by additional transformation analyses, to complete the present invention. Furthermore, some of the regulators are found to stimulate internodes elongation in rice. The flowering-time regulators of rice are expected to exhibit similar effects in other monocotyledons which are developmentally homologous, such as corn, barley, wheat, etc., as in rice.

More specifically, the present invention provides 1) flowering-time and/or internodes elongation regulators; 2) flowering-time regulating proteins encoded by the regulators; 3) constructs wherein the regulator is overexpressed or suppressed; 4) transgenic plants, parts thereof, or plant cells transformed with the construct; 5) methods to prepare the transgenic plants; and 6) methods to regulate flowering-time and/or internodes elongation using the regulators.

The present invention provides a regulator involved in a regulating mechanism of flowering-time and/or internodes elongation.

In the present invention, the mutant lines exhibiting alteration in flowering-time, such as those exhibiting early- or late-flowering phenotypes, are screened from T-DNA-tagged transgenic plants, and the nucleotide sequence of the regions adjacent to the inserted T-DNA is analyzed, to find several flowering-time regulators as described below.

One such flowering-time regulator is *Oryza stavis* MADS50 (hereinafter, referred to as "OsMADS50"), which is one of the MADS-box genes of rice. The nucleotide sequence thereof is shown in SEQ ID NO: 1.

Said regulator is isolated by PCR from the gene having Accession No. AB003328 registered at the NCBI (National Center for Biotechnology Information) database, using a pair of primers specific thereto. The nucleotide sequence of the isolated regulator is analyzed and the regulator is named OsMADS50. OsMADS50 is one of the MADS-box genes, and a conventional MIKC [(MAPS, intervening, Keratin-like, and C-terminal domain)]-type MADS-box gene. The sequence of the genomic DNA of the OsMADS50 gene has been registered to have the Accession No. AC098695. The OsMADS50 gene is present in chromosome 3, and has seven (7) exons and six (6) introns (see FIG. 2a, and alvarez-Buylla et al., 2000; Lee et al., 2003). Among the MIKC-type MADS-box proteins present in rice (Lee et al., 2003), the OsMADS50 protein is the most homologous (60.8%) to the OsMADS56 protein.

OsMADS50 is found to be a flowering activator (accelerating factor) in rice, acting as a rice ortholog of SUPPRESSOR OF OVEREXPRESSION OF CO1/AGAMOUS-LIKE 20 (SOC1/AGL20) in *Arabidopsis*. Such a flowering accelerating effect of OsMADS50 can be shown by the fact that in a OsMADS50 knockout (KO) line wherein the OsMADS50 function is suppressed by T-DNA insertion, etc., a OsMADS50 RNAi (interference) line wherein OsMADS50 region, or a part or all of M, I, K and C domains of MADS-box present in OsMADS50 are deleted, or a modified line wherein a part or all of the above domains are modified by nt substitution, etc., flowering is delayed, whereas in a OsMADS50 overexpressed line (e.g., ubi:OsMADS50) with a strong promoter which is operable in plant, such as actin, cytochrome C, or maize ubiquitin (ubi) promoters, flowering is extremely accelerated at the callus stage.

In the present invention, the overexpression of a gene may be induced by being operably linked to a strong promoter operable in plants, such as actin promoter, cytochrome C, ubiquitin (ubi) promoter (Pubi), etc., or inserting a DNA fragment containing an enhancer into a proper site. The suppression of a gene may be performed by a foreign gene which can be inserted in to a plant gene, such as T-DNA, an endogeneous transposon such as TOS17, a mutation induced by X-ray or gamma-ray irradiation, or by RNAi or anti-sense methods. The overexpression and suppression methods above are also applied to the genes of the present invention.

The analyses of OsMADS50 KO, OsMADS50 RNAi, and ubi:OsMADS50 plants shows that OsMADS50 is an upstream regulator of OsMADS1, OsMADS14, OsMADS15, OsMADS18 and Hd3a, which are involved in the flowering mechanism in rice. This result shows that the OsMADS50 gene regulates flowering of rice not through an independent and direct way, but by controlling various genes involved in flowering mechanisms in rice in a more fundamental way.

Further, it is observed that an OsMADS50 suppressed line displays considerable internode elongation compared with wild type, which shows that the OsMADS50 gene controls stein elongation as well as flowering-time. That is, in the present invention, it is observed that the mutant line having a suppressed OsMADS50 gene exhibits late-flowering but elongated-internode phenotype, whereby it is established that the OsMADS50 gene is involved in stem elongation as well as control of flowering-time.

Further, it is also observed that in the mutant line with suppressed OsMADS50 gene, flowering-time is delayed under long-day conditions only, which shows that the OsMADS50 gene is a flowering activator working under long-day conditions.

In addition to the OsMADs50 gene, OsMADS51, OsMADS56, OsTRX1 and OsVIN2 genes are segregated as a flowering-time regulator working by overexpression or suppression.

The OsMADS51 gene has been registered in the NCBI database under Accession No. AB003327 (SEQ ID NO: 3). The organ-dependent expression profiles of the gene have been known, but its function is not yet known (Shinozuka et al., 1999). The sequence of the genomic DNA of the OsMADS51 gene has been registered under Accession No. AP008207. In the present invention, the OsMADS51 gene was sought out as a gene which alters flowering-time by overexpression or suppression, and isolated by PCR. In the present invention, it is shown that in a line overexpressing OsMADS51, flowering-time is accelerated by 1 to 2 weeks under field conditions, and in a OsMADS51 knockout line, flowering-time is delayed under short-day conditions (see FIG. 11), suggesting that the OsMADS51 gene is also a flowering-time regulator.

As another gene which alters flowering-time by overexpression or suppression, the OsMADS56 gene was isolated, characterized, and registered at NCBI with the Accession No. AY345224 (SEQ ID NO: 5). The genomic DNA sequence of the OsMADS56 gene has been registered under Accession No. AC092697. In the present invention, the flowering-time is delayed by 1 to 2 weeks in an OsMADS56 overexpressed mutant. When the photoperiod condition is controlled, flowering-time is not altered under short-day conditions, whereas it is delayed by approximately one month under long-day conditions (see FIG. 12).

As another gene which alters flowering-time by suppression due to T-DNA insertion, OsTRX1 and OsVIN2 genes were studied, and their nucleotide sequences are shown in SEQ ID NO: 7 (OsTRX1) and SEQ ID NO: 9 (OsVIN2), respectively. The genomic DNA sequences of these genes have been registered under Accession Nos. AP008215 (OsTRX1) and AP008208 (OsVIN2), respectively. In the present invention, the flowering is delayed by at least one month in an OsTRX1 knockout line under field conditions. In an OsVIN2 knockout line, flowering-time is delayed by approximately 32 days under long-day conditions, and delayed by approximately 10 days under short-day conditions. These results show that OsTRX1 and OsVIN2 genes also act as flowering regulators (see FIG. 13).

As another gene which alters flowering-time by suppression due to T-DNA insertion, the OsCOL4 (*Oryza satvia* CONSTANS Like 4) gene was investigated. The nucleotide sequence of the OsCOL4 gene has been known through the Rice Genome Project (SEQ ID NO: 11). The gene has been known as a rice homolog of the CONSTANS gene of *Arabidopsis*, but its function has been unknown. Its genomic DNA sequence has been registered under Accession No. AP004063.

In the present invention, the OsCOL4 activated mutant line (by induction of overexpression, etc.) exhibits delayed flowering-time phenotype with a delay of 15 or more days compared with wild-type (see FIG. 14), whereas the OsCOL4 suppressed mutant line exhibits early flowering-time phenotype which is early by approximately 10 days compared with wild-type. These results show that the OsCOL4 gene acts as a flowering inhibitor. The OsCOL4 gene only has a flowering inhibiting function, and has no effect on vegetative growth such as stem elongation. Upon investigating the alteration of flowering-time of OsCOL4 modified mutants depending on photoperiod conditions, it is found that the OsCOL4 overexpressed mutant exhibits a late-flowering phenotype compared with a wild-type line under both long-day and short-day conditions, whereas the OsCOL4 suppressed mutant exhibits an early-flowering phenotype compared with wild-type under both long-day and short-day conditions. These results show that the OsCOL4 gene acts as a flowering inhibitor in rice, regardless of the photoperiod conditions.

In all embodiment of the present invention, the activation of the OsCOL4 gene may be induced by a 35S enhancer in T-DNA inserted into a promoter region of OsCOL4 gene (see FIGS. 15 and 16), or by a ubiquitin (ubi) promoter (Pubi) operably linked thereto (see FIG. 17). The suppression of the OsCOL4 gene may be induced by an insertion of T-DNA into the first exon or 3'UTR region of the OsCOL4 gene (see FIG. 18).

Many flowering regulators of plants have been known, most of which are flowering-time activators, but only few of them are flowering inhibitors. Therefore, it is very valuable to find flowering inhibitors such as OsMADS56 and OsCOL4. In activating flowering, the flowering inhibitor suppressed mutants can be more stably inherited than the flowering activator overexpressed mutants. Further, the OsCOL4 suppressed mutants can be obtained by ways other than transformation, such as mutation by an endogenous transposon of rice, Tos17, and thus, problems of genetically modified organisms (GMO) can be avoided.

As another flowering regulator, OsCOL8 (*Oryza sativa* CONSTANS Like 8) is investigated, which is a CONSTANS like gene present in rice, and similar to the VRN2 gene controlling flowering-time in wheat by vernalization treatment. The nucleotide sequence of the OsCOL8 gene has been known through the Rice Genome Project (SEQ ID NO: 13), but the function thereof has been unknown. The genomic DNA sequence of the gene has been registered under Accession No. AC079874. In the present invention, it is found that an OsCOL8 suppressed mutant shows no alteration in flowering-time under long-day conditions, whereas it shows late-flowering phenotype under short-day conditions. These results show that the OsCOL8 gene is a flowering activator in plants under short-day conditions.

The flowering regulators of the present invention may act independently from each other. Further, each of the regulators may more effectively control flowering-time by acting in association with another regulator with a similar or opposed regulation activity to create offset or synergy of the flowering regulating action.

In addition to the above genes, OsMADS14 is investigated as another flowering regulator. The genomic DNA sequence and cDNA sequence of the OsMADS14 gene are shown in SEQ ID NO: 15 and SEQ ID NO: 16, respectively. APETALA1 (AP1) gene of *Arabidopsis* has been known- to be involved in the formation of floral organs and regulation of flowering-time. At least four (4) genes have been known as AP1 like genes present in rice. The four genes have been named OsMADS14, OsMADS15, OsMADS18 and OsMADS20, respectively. Among them, the OsMADS14 gene has been first cloned as a coding gene of a reciprocally binding partner of an OsMADS6 protein, and it has been known that the overexpression of the gene induces early flowering, but the details of the mechanism and conditions for such a function have been unknown.

In the present invention, it is observed that the mutants wherein T-DNA or Tos17 is inserted into the OsMADS14 gene exhibit no particular change in flowering-time and floral development (see FIG. 21). This result shows that other genes besides the OsMADS14 gene act redundantly in regulating flowering-time. Overexpression of the modified OsMADS14 protein, wherein among M, I, K (KI, KII, KIII, KIV) and C domains present in the MADS-box of OsMADS14, the terminus containing the C domain is deleted, leads to early-flowering by approximately one-month under short-day conditions, whereas it leads to late-flowering by approximately 2 weeks under long-day conditions. The partial OsMADS14 protein wherein the C domain is deleted may be obtained by deletion of the 3'-terminal region containing the C-domain coding sequence of the OsMADS14 gene and expression thereof. In an embodiment of the present invention, such C domain deleted partial OsMADS14 protein may be obtained by inserting a stop codon between the K and C domains. The nucleotide sequence of the OsMADS14 gene with the C domain coding region deleted is shown in SEQ ID NO: 17, and the amino acid sequence of the C domain deleted partial OsMADS14 protein encoded thereby is shown in SEQ ID NO: 18. The above results show that the C domain deleted partial OsMADS14 protein activates flowering-time under short-day conditions, while it inhibits flowering by interaction with the flowering activators under long-day conditions.

In corn, wheat, etc., which are monocotyledons like rice, counterparts of OsMADS50, OsMADS51, OsMADS56, OsMADS14, OsTRX1, OsVIN2, OSCOL4 and OsCOL8 of rice are also expected to act as regulators in flowering and/or stem elongation.

Another aspect of the present invention provides a flowering regulating protein encoded by OsMADS50; OsMADS51; OsMADS56; truncated OsMADS14 wherein a C domain coding sequence containing the 3'-terminal region is deleted; OsTRX1; OsVIN2; OSCOL4; or OsCOL8 genes. The flowering regulating protein may have an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14 and SEQ ID NO: 18.

Another aspect of the present invention provides DNA constructs containing the overexpressed or suppressed flowering regulators.

The DNA construct may contain a suppressed OsMADS50, OsMADS51, OsMADS56, OsMADS14, OsTRX1 or OsVIN2 gene. More specifically, the DNA construct may contain a knockout variant of OsMADS50, OsMADS51, OsMADS56, OsMADS14, OsTRX1 or OsVIN2 gene induced by insertion of a foreign gene. For example, the DNA construct may contain a knockout variant wherein a DNA fragment which can be inserted in to a plant gene, such as T-DNA, is inserted in a specific site in OsMADS50, OsMADS51, OsMADS56, OsMADS14, OsTRX1 or OsVIN2 gene. Especially, in the case of OsMADS50, T-DNA may be inserted into the fourth ($4^{th}$) intron among six introns (see FIG. 2a). Alternatively, the DNA construct of the present invention can contain suppressed OsMADS50, OsMADS51, OsMADS56 or OsMADS14 gene by deletion or nt substitution of the whole or part of OsMADS50, OsMADS51 or OsMADS56 gene, preferably the part containing at least the MADS-box region.

The DNA construct of the present invention can also contain an overexpressed OsMADS50, OsMADS51, OsMADS56, OsTRX1 or OsVIN2 gene. In an embodiment of the present invention, the DNA construct may contain an overexpressed OsMADS50, OsMADS51, OsMADS56, OsTRX1 or OsVIN2 gene wherein a strong promoter operable in plants, such as actin promoter, cytochrome C promoter and maize ubiquitin (ubi) promoter, is operably inked.

The DNA construct of the present invention may contain a truncated OsMADS14 gene producing a C domain deleted partial OsMADS14 protein by deletion of 3'-terminal region containing the C domain coding sequence. The C domain coding sequence containing truncated OsMADS14 with the 3'-terminal region deleted may be linked with a strong promoter operable in plants to induce an overexpression thereof.

The DNA construct may contain an overexpressed OsCOL4 gene. In an embodiment of the present invention, the overexpression of the OsCOL4 may be induced by operable linkage of a strong promoter, such as actin promoter, cytochrome C promoter, maize ubiquitin (ubi) promoter, or insertion of a DNA fragment which can be inserted in to a plant gene, such as T-DNA, into the promoter of the OsCOL4 gene, wherein an enhancer (e.g., 35S enhancer of T-DNA) of the inserted gene induces an overexpression of the gene. The DNA construct of the present invention may contain a suppressed OsCOL4 gene. In an embodiment of the present invention, the OsCOL4 gene may be suppressed by insertion of a DNA fragment which can be inserted into a plant gene, such as T-DNA, into a specific site of the OsCOL4 gene, more specifically, by insertion of T-DNA into the first exon or 3' UTR region.

The DNA construct of the present invention may contain an overexpressed OsCOL8 gene. In an embodiment of the present invention, the OsCOL8 gene may be overexpressed by operable linkage with a strong promoter, such as maize ubiquitin (ubi) promoter. Further, The DNA construct of the present invention may contain a suppressed OsCOL8 gene. In an embodiment of the present invention, the OsCOL8 gene may be suppressed by insertion of a DNA fragment which can be inserted into a plant gene, such as T-DNA, into a specific site of the OsCOL8 gene, more specifically, by insertion of T-DNA into the first exon region.

Another aspect of the present invention provides a transgenic plant, a part thereof, or a plant cell, wherein an overexpression or suppression of the flowering-time regulator is directly induced as above, or wherein transformation with a DNA construct containing the overexpressed or suppressed flowering-time regulator is performed. There is no limitation of the vector used in the transformation of the plant, part thereof, or plant cell. Any conventional vector which can be used in transformation of plants may be used, and more specifically, a binary vector of pGA1611 family may be used.

More specifically, the transgenic plant, part thereof, or plant cell of the present invention may have overexpression of the OsMADS50, OsMADS51, OsTRX1, OsVIN2 or OsCOL8 gene directly induced as above, or be transformated with a DNA construct containing the OsMADS50, OsMADS51, OsTRX1, OsVIN2 or OsCOL8 gene where overexpression is induced, whereby flowering-time is accelerated. In the transgenic plant, part thereof, or plant cell of the present invention, the suppression of OsMADS50, OsMADS51, OsTRX1, OsVIN2 or OsCOL8 gene may be directly induced as above, or transformation with a DNA construct containing the suppressed OsMADS50, OsMADS51, OsTRX1, OsVIN2 or OsCOL8 gene may be performed, whereby flowering-time is delayed.

In the transgenic plant, part thereof, or plant cell of the present invention, the overexpression of OsMADS56 or OsCOL4 gene may be directly induced as above, or transformation with a DNA construct containing the overexpressed OsMADS56 or OsCOL4 gene may be performed, whereby flowering-time is delayed. In the transgenic plant, part thereof, or plant cell of the present invention, the suppression of OsMADS56 or OsCOL4 gene may be directly induced as above, or transformation with a DNA construct containing the suppressed OsMADS56 or OsCOL4 gene may be performed, whereby flowering-time is accelerated.

The transgenic plant, part thereof, or plant cell of the present invention may be transformed with a DNA construct containing the OsMADS14 gene having the C domain coding region deleted, to produce a C domain deleted partial OsMADS14 protein, whereby flowering-time is delayed under long-day conditions and accelerated under short-day conditions.

The transgenic plant, part thereof, or plant cell of the present invention may be one wherein the suppression of the OsMADS50 gene is directly induced, or which is transformed with a DNA construct containing the suppressed OsMADS50 gene, to exhibit considerable stem elongation compared with wild type.

Another aspect of the present invention provides a method to regulate flowering-time and/or stem elongation by inducing an overexpression or suppression of the regulators as above.

The flowering-time regulating method of the present invention may comprise the step of inducing a suppression of OsMADS50, OsMADS51, OsTRX1, OsVIN2 or OsCOL8 gene, to delay flowering-time. More specifically, the flowering-time regulating method of the present invention may comprise the step of directly inducing a suppression of OsMADS50, OsMADS51, OsTRX1, OsVIN2 or OsCOL8 gene by insertion of a foreign gene, or gene deletion, or transforming with a DNA construct containing a suppressed OsMADS50, OsMADS51, OsTRX7, OsVIN2 or OsCOL8 gene, to delay flowering-time. For example, the suppression of the OsMADS50, OsMADS51, OsTRX1, OsVIN2 or OsCOL8 gene may be induced by insertion of a DNA fragment which can be inserted into a plant gene, such as T-DNA, into a specific site of the above gene. For example, in the case of the OsMADS50 gene, T-DNA may be inserted into the fourth intron among the six introns, and in the case of the OsCOL8 gene, T-DNA may be inserted into the first exon, to suppress the genes.

Alternatively, the suppression of the OsMADS50, OsMADS51, OsTRX1, OsVIN2 or OsCOL8 gene may be induced by deletion of the whole or part of the gene. For example, in case of the OsMADS50, OsMADS50 or OsMADS51 gene, at least the MADS-box region may be deleted, to suppress the gene.

The flowering-time regulating method of the present invention may comprise the step of transforming a plant with a DNA construct containing the suppressed OsMADS50, OsMADS51, OsTRX1, OsVIN2 or OsCOL8 gene as above, to delay flowering-time in the plant.

Further, the present invention provides a method of stimulating stem elongation by inserting a foreign gene into the OsMADS50 gene or deleting the whole or part of the OsMADS50 gene to induce suppression thereof.

The flowering-time regulating method of the present invention may comprise the step of inducing overexpression of the OsMADS50, OsMADS51, OsTRX1, OsVIN2 or OsCOL8 gene to activate flowering. For example, the flowering-time regulating method of the present invention may comprise the step of inducing overexpression by operably linking a strong promoter operable in plants to the OsMADS50, OsMADS51, OsTRX1, OsVIN2 or OsCOL8 gene to accelerate flowering-time. The flowering-time regulating method of the present invention may comprise the step of transforming a plant with a DNA construct containing an overexpressed OsMADS50, OsMADS51, OsTRX1, OsVIN2 or OsCOL8 gene which is operably linked with the above strong promoter, to accelerate flowering-time. The strong promoter includes the actin promoter, cytochrome C promoter, maize ubiquitin (ubi) promoter, etc.

The flowering-time regulating method of the present invention may comprise the step of inducing overexpression of the OsMADS56 or OsCOL4 gene to inhibit flowering, or inducing suppression of the OsMADS56 or OsCOL4 gene to activate flowering.

More specifically, the flowering-time regulating method of the present invention may comprise the step of inducing overexpression of the OsMADS56 or OsCOL4 gene by operable linkage with a strong promoter, or insertion of an enhancer containing foreign gene which can be inserted in a plant genome into the promoter region of the gene, to inhibit flowering. For example, the flowering-time regulating method of the present invention may comprise the step of inducing overexpression of the OsMADS56 by operable linkage with maize ubiquitin (ubi) promoter, or overexpression of the OsCOL4 gene by insertion of T-DNA which contains 35 enhancers into the promoter region of the OsCOL4 gene, to inhibit flowering. The flowering-time regulating method of the present invention may comprise the step of transforming a plant with a DNA construct containing the overexpressed OsMADS56 or OsCOL4 gene as above, to inhibit flowering.

The flowering-time regulating method of the present invention may comprise the step of inducing overexpression of a C domain deleted partial OsMADS14 protein by deletion of the 3'-terminal region containing the C domain coding sequence of the OsMADS14 gene, to delay flowering-time under long-day conditions, and to accelerate the flowering-time under short-day conditions.

The flowering-time regulating method of the present invention may comprise the step of inducing suppression of the OsMADS56 or OsCOL4 gene by insertion of a foreign gene, which can be inserted into a plant gene, into a specific site of the OsMADS56 or OsCOL4 gene, to activate flowering. More specifically, the flowering-time regulating method of the present invention may comprise the step of inducing suppression of the OsCOL4 gene by inserting T-DNA into the first exon or 3' UTR region of the OsCOL4 gene, to activate flowering. The flowering-time regulating method of the present invention may comprise the step of transforming a plant with a DNA construct containing the suppressed OsMADS56 or OsCOL4 gene as above, to activate flowering.

The flowering-time regulating method of the present invention may comprise the step of inducing overexpression of the OsMADS14 gene, to accelerate flowering under short-day conditions, and to delay flowering under long-day conditions. Such overexpression of the OsMADS14 gene may be performed by overexpressing a partial OsMADS14 protein wherein a C terminal region is deleted.

Another aspect of the present invention provides a method of preparing a flowering-time regulated transgenic plant, a part thereof, or a plant cell, comprising the step of transforming with a DNA constrict containing the overexpressed or suppressed flowering-time regulator. The preparation method of the present invention comprises the steps of providing a plant cell; transforming the plant cell with the DNA construct above; and cultivating the transformed cell. The flowering-time regulator may be selected from the group consisting of OsMADS50, OsMADS51, OsMADS56, OsMADS14, OsTRX1, OsVIN2, OsCOL4 and OsCOL8, which is overexpressed or suppressed through the above method. The transformed plant cell may be cultivated as cells, differentiated to specific tissue by a conventional method of inducing tissue differentiation, or developed to a plant body.

The methods of the present invention to regulate flowering-time or to prepare a transgenic plant may be also applied to monocotyledons other than rice, such as corn and wheat, wherein counterparts of the OsMADS50, OsMADS51, OsMADS56, OsMADS14, OsTRX1, OsVIN2, OsCOL4 and OsCOL8 genes of rice may be used.

BRIEF DESCRIPTION OF FIGURES

FIG. 22 shows the nucleotide sequence of OsMADS50 cDNA (SEQ ID NO: 1).

FIG. 23 shows the nucleotide sequence of OsMADS51 cDNA (SEQ ID NO: 3).

FIG. 24 shows the nucleotide sequence of OsMADS56 cDNA (SEQ ID NO: 5).

FIG. 25 shows the nucleotide sequence of OsTRX1 cDNA (SEQ ID NO: 7).

FIG. 26 shows the nucleotide sequence of OsVIN2 cDNA (SEQ ID NO: 9).

FIG. 27 shows the nucleotide sequence of OsCOL4 cDNA (SEQ ID NO: 11).

FIG. 28 shows the nucleotide sequence of OsCOL8 cDNA (SEQ ID NO: 13).

FIGS. 29A to 29F show the nucleotide sequence of genomic DNA of OsMADS14 (SEQ ID NO: 15).

FIG. 30A shows the nucleotide sequence of OsMADS4 cDNA (SEQ ID NO: 16).

FIG. 30B shows the nucleotide sequence of truncated OsMADS14 (SEQ ID NO: 17) wherein the 3'-terminal region containing the C domain coding sequence is deleted from the OsMADS14 gene.

EXAMPLE 1

Selection 1 of Flowering-time Mutants in T-DNA-tagging Lines

Rice cells (*Oryza sativa* var. *japonica* cv. Dongjin induced calluses) were treated by using Ti plasmid binary vector pGA2144 (Jeon et al., *The Plant Journal* (2000) 22(6), 561-570), to construct a T-DNA inserted T1 (first generation) mutant lines. The treatment using Ti plasmid binary vector pGA2144 was performed according to "Jeon et al. 2000b". That is, the rice cells were co-cultivated with agrobacteria, to transport T-DNA into the rice cells, and the T-DNA transported cells were selected by using an antibiotic and re-differentiated. 2933 T1 mutant lines obtained were developed in the field, to produce T2 (second generation) transgenic plants, wherein mutant lines exhibiting alteration in flowering-time were selected. Twenty-five (25) lines exhibiting alteration in flowering-time by at least 2 weeks compared with the flowering-time of the wild-type line were observed, wherein 16 lines exhibited early-flowering phenotype, and 9 lines exhibited late-flowering phenotype.

Figure 1:
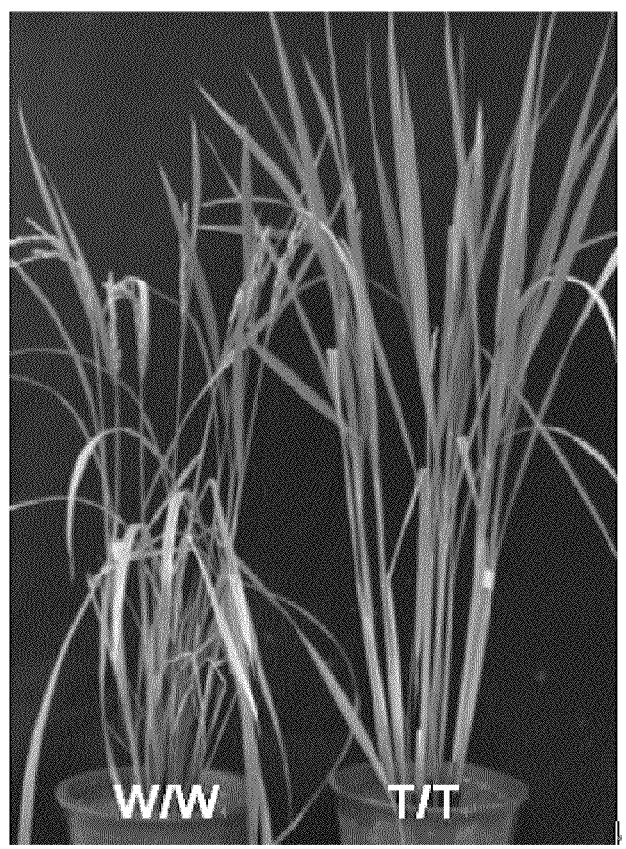
FIG. 1 shows the mutant (T/T) wherein T-DNA is inserted into the OsMADS50 gene, and the wild-type control (W/W).

FIG. 1 shows a phenotype comparison between OsMADS50 knockout (10) plants wherein T-DNA is inserted in the OsMADS50 gene, and wild-type (WT) plants. The photograph was taken when WT plants flowered. However, the OsMADS50 KO plants had not bolted yet.

To analyze of the genotype of flowering-time mutant, the nucleotide sequence of the adjacent region of the insertion region of T-DNA was analyzed by using an inverse PCR method as reported in "An et al. 2003," wherein the genomic DNA was cleaved by a restriction enzyme, both ends are linked together, and then PCR is performed twice, to identify the nucleotide sequence of the adjacent region of the T-DNA inserted region. Then, the insertion site of T-DNA was confirmed by using the National Center for Biotechnology Information (NCBI) database. As a result, in a line shown at the right side in FIG. 1 (line 0-153-43), the retrieved sequence was the MADS-box gene OsMADS50, and the insertion site of T-DNA was the fourth intron of OsMADS50 (see FIG. 2a). The OsMADS50 protein showed 50.6% amino acid sequence identity with SOC1/AGL20 which is a flowering activator of *Arabidopsis*. Among the 36 MIKC (MAPS, intervening, Keratin-like, and C-terminal domain)-type MADS-box proteins present in rice, the OsMADS50 protein is most homologous (60.8%) to OsMADS56, and also shares homology with maize ZmMADS1 (75.2%), Tobacco TobMADS1 (51.1%) and mustard SaMADSA (50.0%). Full-length protein sequences were aligned to calculate homologies.

As shown in FIG. 1, in the mutant line (T/T) wherein T-DNA is inserted into the OsMADS50 gene, flowering-time was delayed by approximately one month compared with the wild-type (W/W) control. Such delay in flowering caused by the mutation induced in OsMADS50 is considered to be a significant result, because the OsMADS50 gene is thought to be the counterpart corresponding to the flowering-time regulator AGL20 of *Arabidopsis*.

As shown in FIG. 2a, one of the MADS-box genes, OsMADS50, is located on Chromosome 3, and is composed of six introns and seven exons that encode a typical MIKC-type MADS-box protein. In T-DNA inserted lines in the present example, the T-DNA was inserted into the fourth intron, and the transcript direction of beta-glucuronidase (gus) gene in the T-DNA was opposite to that of OsMADS50.

From FIG. 2a, the genotype of T2 plants was determined via PCR using the primers located in OsMADS50 and T-DNA. The amplification of the normal OsMADS50 gene (W) was confirmed by PCR using primers F2 (forward primer in the I region: 5'-aaagctgacg ctgatggttt-3', SEQ ID NO: 23) and R1 (reverse primer at 3' UTR: 5'-ttgggtaccg agatccagct tattcctgg-3', SEQ ID NO: 22), and the amplification of the T-DNA inserted OsMADS50 gene (T) was confirmed by PCR using primers F2 and R2 (reverse primer in the hygromycin phosphotransferase (hph)).

As a result, among thirteen (13) plants, three (3) were homozygotic (T/T) for the T-DNA insertion (see FIG. 2b, Samples 4, 10 and 13). All of these plants flowered about 99 days after planting. Whereas the other T2 plants, being either heterozygotic (W/T) or wild-type (W/W) segregants, flowered about 73 days after planting.

Figure 2:
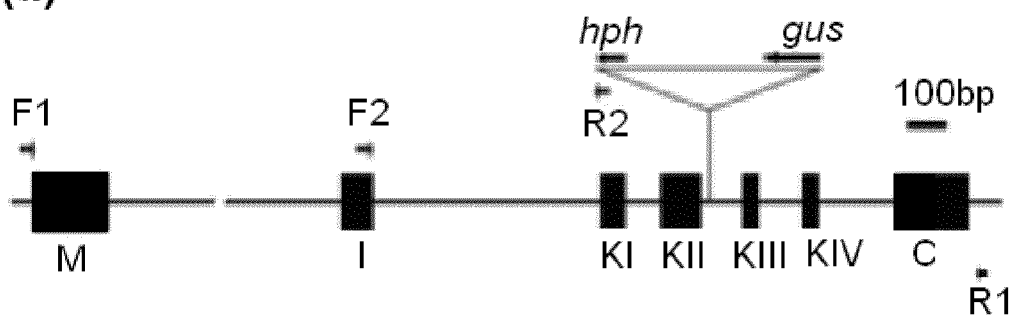
FIG. 2 shows the factors, phenotype and flowering time of OsMADS50 KO (knockout) plants, wherein (a) shows the structure of OsMADS50 and the T-DNA insertion position therein; and (b) shows the phenotype of T-DNA-inserted T2 (generation 2) plants which are suppressed.
Figure 2:
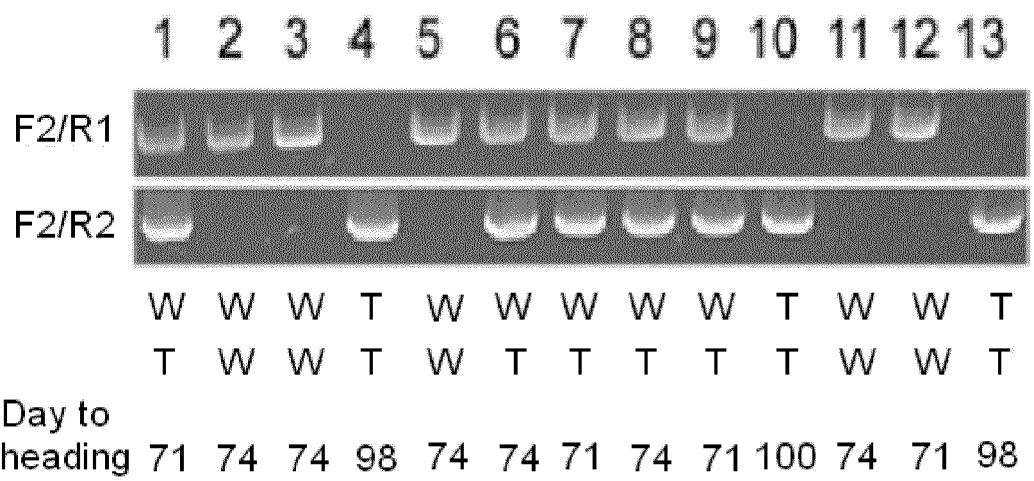

FIG. 2 is a schematic diagram of OsMADS50, showing the position of T-DNA insertion and the genotyping of the OsMADS50 KO progeny. FIG. 2a shows the structure of OsMADS50 and T-DNA insertion. Seven exons (filled boxes) and six introns (lines between the filled boxes) are shown. In FIG. 2a, the M, I, K and C region indicate exons. The K region consists of four exons, whereas the other regions comprise one exon each. T-DNA was inserted into the fourth intron. Arrows indicate primers. F1 is a forward primer at 5'UTR, F2 is a forward primer in the I region, R1 is a reverse primer at 3'UTR, and R2 is a reverse primer in the hygromycin phosphotransferase (hph) gene in T-DNA.

FIG. 2b shows the genotyping of the OsMADS50 KO progeny. If no T-DNA insertion occurred, the F2 and R1 primers should be amplified as 1.6 kb genomic DNA. If T-DNA was inserted, the length between the two primers would be too large to be amplified. Furthermore, when the T-DNA is inserted into the fourth intron, the F2 and R2 primers should be amplified as an approximately 2 kb band. Samples 2, 3, 5, 11 and 12 were amplified as only the genomic DNA and therefore, they were considered to be wild-type (W/W); Samples 4, 10 and 13, which were harvested from late-flowering mutants, were amplified only as 2 kb bands, and therefore, they were considered to be heterozygous (T/T); and the other samples showed amplification of both bands and therefore, they were considered to be heterozygous (W/T). Days to heading after planting are indicated for each plant.

As seen from the above, all the late flowering plants included only T-DNA inserted OsMADS50 (T/T), and the normal flowering plants contained at least one normal OsMADS50 gene (W). Therefore, it could be confirmed that a late-flowering mutation is induced by T-DNA insertion.

EXAMPLE 2

Isolation of the OsMADS50 Gene

The nucleotide sequence of the above OsMADS50 gene is shown in SEQ ID NO: 1. The nucleotide sequence of the OsMADS50 gene is also registered in NCBI database under Accession No. AB003328. However, only the expression profiles in various organs is known, whereas its function is yet unknown (Shinozuka et al., 1999). Herein, the present inventors designed two specific primer pairs, isolated this gene through PCR using the primer pairs, and named the gene OsMADS50. The first PCR was performed for the gene using the primer pair having the nucleotide sequences of SEQ ID NO: 19 (F1: forward at 5' UTR: 5'-atcaagcttt acggccaaac cctacagc-3') and SEQ ID NO: 20 (R1: reverse primer at 3' UTR: 5'-ttgggtaccg atgggtagtg gagtctgc-3'), and then, the second PCR was performed using the PCR amplified product as a template and using a primer pair correspondiing to the nucleotide sequences of SEQ ID NO: 21 (5'-atcaagcttg ttggt-tcatc ggcgatcg-3') and SEQ ID NO: 22 (5'-ttgggtaccg agatc-cagct tattcctgg-3') present inside the PCR product to amplify the desired gene. The PCR amplified product containing the entire coding region of S11905 and the adjacent region was cleaved by HindIII-BamHI (Roche), and cloned into a pBluescript SK (−) vector (Stratagene). The nucleotide sequence thereof was determined by a sequencing machine (AbI3100), and the obtained gene was named OsMADS50. This gene is present in the clone registered as AP004322 positioned at the short arm of Chromosome 3, and this locus is identical to that of the mutation known as Hd9 (Lin et al., 2000).

EXAMPLE 3

Analysis of OsMADS50 RNA Interference (RNAi) Plants

To confirm that the late-flowering phenotype is due to the suppression of OsMDS50 gene expression, transgenic plants were generated by expressing RNAi constructs of the gene as shown in FIG. 3a. MAD S-box deleted OsMADS50 genes were cloned into pBluescript SK (−) vector (Stratagene) in opposite directions at both sides of the GUS gene, and then inserted in the pGA1611 vector (AY373338) at the position between the maize ubiquitin promoter (Pubi) and the nos terminator (Tnos). Among 82 T1 plants, 76 showed the delayed flowering phenotype delayed by at least one month (FIG. 3b). Six plants flowered 74 to 78 days after planting, similarly to the wild type control and transgenic controls; eight did not flower until 140 days after planting. These results show that the OsMADS50 gene is an important flowering activator.

In addition to the late-flowering phenotype, the transgenic plants carried more elongated internodes (FIG. 3c). In contrast, most of the OsMADS50 RNAi plants carried six (23.5%) to seven (62.7%) elongated internodes, but with some (13.7%) bearing as many as eight. In contrast, the wild-type (WT) and transgenic control (CON) plants possessed five to six elongated internodes. These results show that the OsMADS50 RNAi plant exhibits an internode elongation phenotype as well as a late-flowering phenotype.

Figure 3:
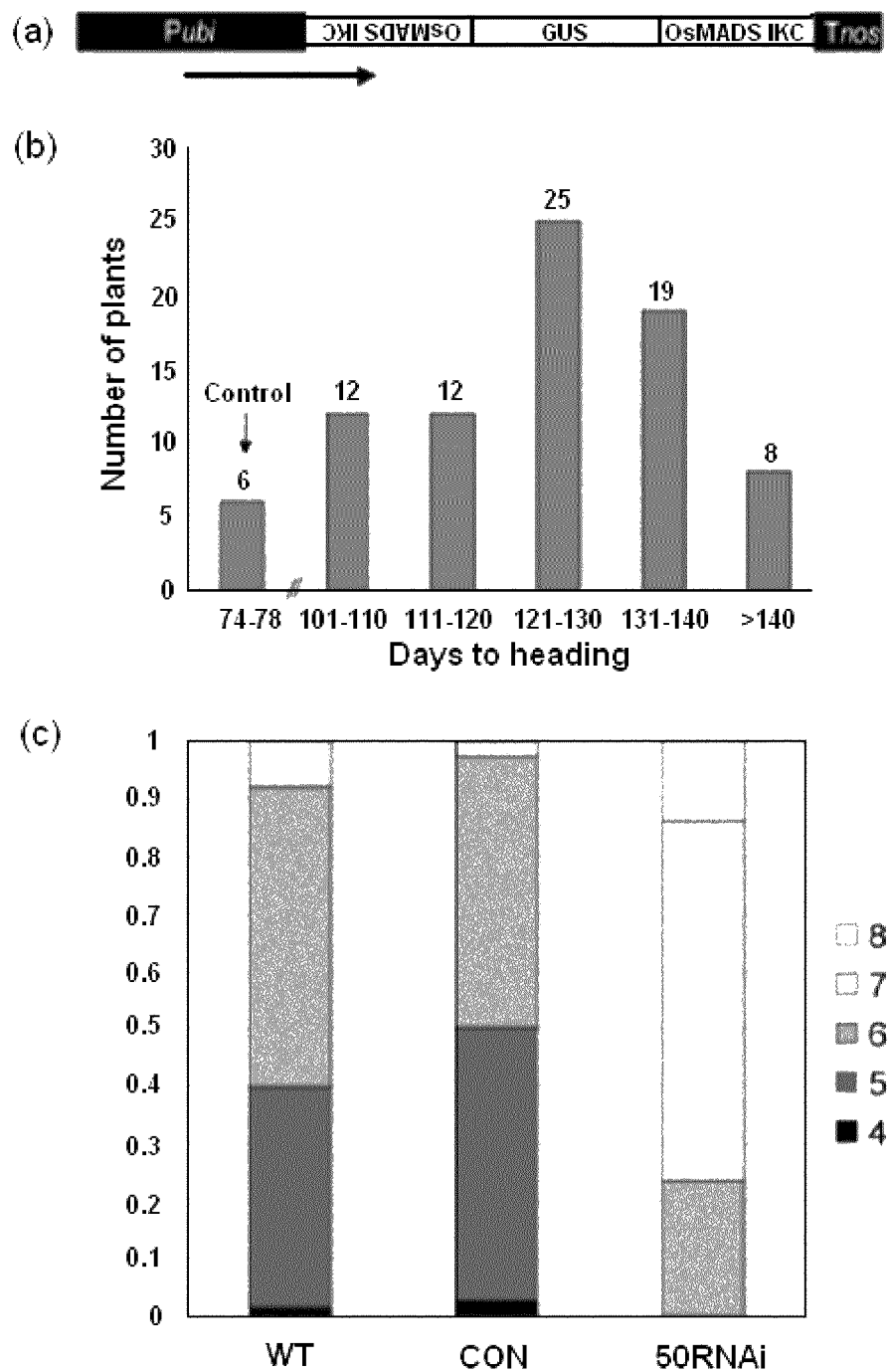
FIG. 3 shows the result of analysis of transgenic plants transformed with OsMADS50 RNAi (interference) vector, wherein (a) shows the structure of OsMADS50 RNAi vector; and (b) shows the distribution of flowering-time of rice T1 (generation 1) plants; and (c) shows the distribution of the number of elongated internodes of rice T1 plants.

FIG. 3 is a schematic diagram of the OsMADS50 RNAi construct and the phenotypes of the transgenic plants expressing the RNAi construct. FIG. 3a shows the OsMADS50 RNAi construct, with a GUS spacer inserted between two IKC regions of OsMADS50. The construct was inserted between the maize ubi promoter (Pubi) and the nos terminator (Tnos). FIG. 3b shows the frequency distribution of days to heading in the OsMADS50 RNAi T1 transgenic Plants, i.e., the number of days required for flowering from the time of transplanting. The wild-type (WT) and other transgenic control plants flowered 74 to 78 days after planting. Nine lines did not flower until 140 days after planting. The broken bar indicates a large gap between two X-axis values. FIG. 3c shows the proportion of elongated internode numbers in OsMADS50 RNAi plants and WT controls. The values are averages of 63 WT, 152 transgenic control plants, and 102 OsMADS50 RNAi plants. The Y-axis indicates the relative ratio of stems having elongated internodes, ranging from 4 to 8.

RNA gel blot analysis showed that high levels of the OsMADS50 RNAi transcript were present in the transgenic plants that displayed the late-flowering phenotype. Because expression was so high, it was difficult to visualize the endogenous OsMADS50 transcript levels in the blots. Therefore, RT-PCR analyses were employed to verify suppression of OsMADS50 expression (FIG. 4b). In the late-flowering transgenic plants, transcript levels (confirmed by F1/R1 primers) were significantly reduced. These results indicate that reducing the expression of OsMADS50 results in late flowering of rice plants. The degree of lateness in flowering was proportional to the RNAi levels since the RNAi plants 9 and 10 flowered later than plants 6 to 8.

Figure 4:
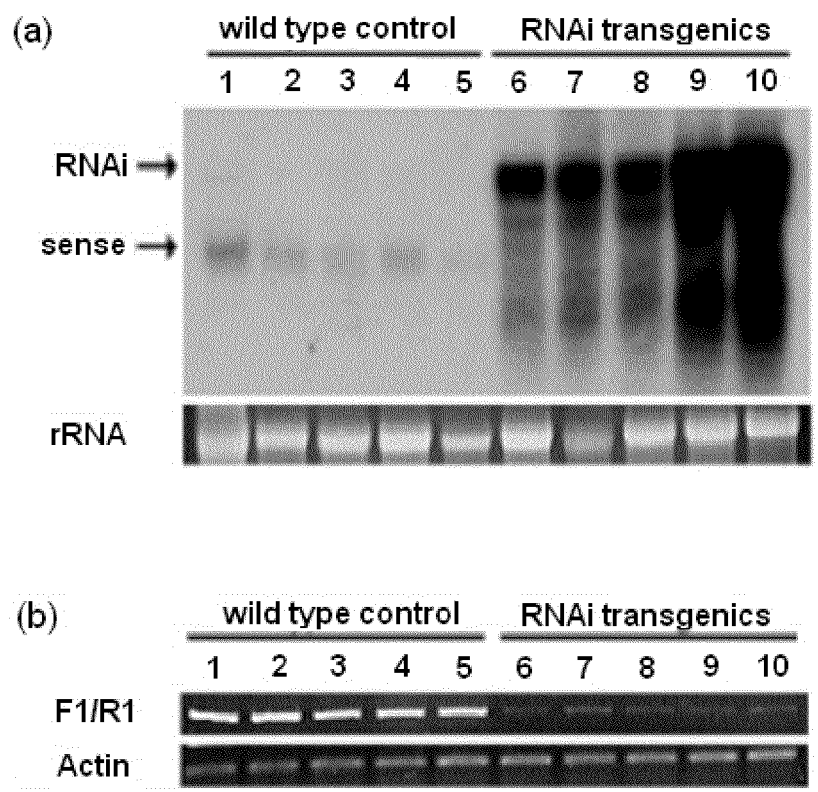
FIG. 4 shows the result of analysis of the OsMADS50 RNA interference effect, wherein (a) shows the result of RNA gel blot for the expression profile of endogenously expressed OsMADS50 and foreign RNAi gene; and (b) shows the result of RT-PCR of endogenously expressed OsMADS50.

FIG. 4 is an analysis of the OsMADS50 RNA interference effect, showing the endogenous level of OsMADS50 in OsMADS50 RNAi Plants. FIG. 4a is a result of RNA gel blot analysis for OsMADS50 and OsMADS50 RNAi transcripts in transgenic plants expressing OsMADS50 RNAi constructs, showing that the OsMADS50 RNAi gene is strongly expressed in the OsMADS50 RNAi transgenics. Five WT plants (1 to 5) and five independent transgenic plants (6 to 10) were examined. The transgenic plants 6, 7, 8, 9, and 10 flowered 111, 115, 115, 130, and 135 days after planting, respectively. The rRNA level was observed as a control (bottom). "RNAi" refers to an OsMADS50 RNAi transcript: and "sense" refers to an endogenous OsMADS50 transcript. FIG. 4b shows the results of RT-PCR analyses for OsMADS50 and OsMADS50 RNAi transcripts in WT plants (1 to 5) and transgenic plants (6 to 10). Identical RNA, isolated for RNA gel blot analysis, was reverse transcribed to synthesize cDNA. The primer pair used for detecting full-length OsMADS50 was F1 (SEQ ID NO: 2)/R1 (SEQ ID NO: 5), indicated in FIG. 2a. Actin was used as a control. PCR cycles for amplifying OsMADS50 and actin were 26 and 23, respectively. The results of RT-PCR analyses using the F1/R1 primer pair show that the OsMADS50 gene which is endogenously expressed is suppressed in the OsMADS50 RNAi transformant.

EXAMPLE 4

Analysis of OsMADS50 Overexpressed Plants

To further study the functional roles of OsMADS50 in flowering time, transgenic rice plants that overexpressed the sense constructs of the gene were generated as shown in FIG. 5a. The maize ubi promoter was used to drive constitutive expression. That is, the whole coding region of OsMADS50 gene was amplified by using a primer pair having the sequence of SEQ ID NO: 2 and SEQ ID NO: 3, respectively, cleaved by HindIII-Asp718 (Roche), cloned into pBluescript SK (−) vector (Stratagene), to confirm the nucleotide sequence, and inserted between the ubiquitin promoter and the nos terminator of the pGA1611 vector (AY373338).

When transformed calli were transferred onto shoot induction media (MRS media), about 20% of the calli developed into the structures that resembled floral organs, e.g., palea/lemma (FIG. 5b), stigmas (FIG. 5b), stamens (FIG. 5c), ovaries (FIG. 5c), and panicles (FIG. 5d). A spikelet containing all the floral organs was occasionally observed. Although approximately 80% of the calli developed into shoots, two thirds of those displayed the phenotype of extreme dwarfism and defective growth of the leaf blade (FIG. 5e). These plants eventually died. The remaining one third of the shoots differentiated into normal plants. Some then flowered earlier than the controls, while others flowered at the same time as the WT plants.

To examine whether the floral organ-like structures observed from the transgenic calli were indeed reproductive, the transcript levels of the flower-specific MADS-box genes, OsMADS3 and OsMADS4 were determined. The former is the C function gene (involved in development of stamen and pistil), and the latter is the B function gene (involved in development of calyx and stamen). These genes were expressed specifically in the floral organs that developed from the ubi:OsMADS50 transgenic calli, indicating that they were authentic.

Figure 5:
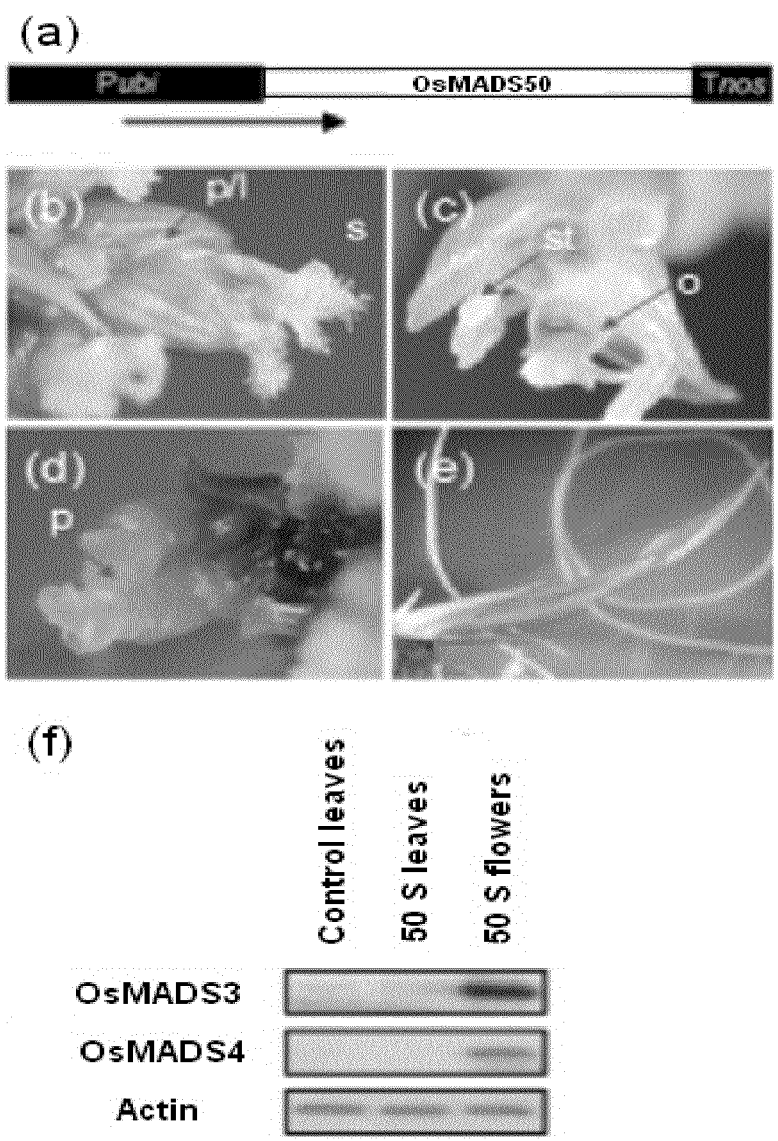
FIG. 5 shows the result of analysis of an OsMADS50 overexpressed mutant, wherein (a) shows the structure of the OsMADS50 overexpressing vector; (b)-(e) show phenotypes of rice T1 plants; and (f) shows the expression profile of OsMADS3 and OsMADS4 in floral-like organs.

FIG. 5 shows the result of analyses of ubi:OsMADS50 plants. FIG. 5a is a schematic diagram of the OsMADS50 sense construct (Pubi: maize ubi prompter, Tnos: nos terminator). FIG. 5b shows regenerated shoots with palea/lemma (p/l)- and stigma (s)-like structures. FIG. 5c shows regenerated shoots with Stamen (st)- and ovary (o)-like structures. FIG. 5d shows regenerated shoots with panicle (p)-like structures. FIG. 5e shows regenerated shoots displaying dwarfism and defective growth of the leaf blade. FIG. 5f shows expression portraits of OsMADS3 and OsMADS4 in the floral organ-like structures (Control leaves: leaves transformed with empty vector; 50S leaves: transgenic leaves overexpressing OsMADS50; and 50S flowers: floral organ-like structures overexpressing OsMADS50). Actin was used as a control. As shown by RT-PCR, the expressions of OsMADS3 and OsMADS4 genes which are expressed specifically in the floral organs were increased in the 50S flower which is a floral organ-like structure. In contrast, expressions of these genes were not detected in control leaves and transgenic leaves (50S leaves).

EXPERIMENTAL EXAMPLE 1

Expression Analysis for Flowering-time Regulators Including OsMADS50

RNA gel blot analysis revealed that OsMADS50 was variably expressed in most organs (FIG. 6a). To perform the analysis, seedling roots, seeding shoots, young leaf blades (LBs) at 9 to 10 leaf stage, leaf blades at 80 DAP (days after planting), leaf blades at 105 DAP, flag leaf blades 105 DAP, panicles <2 cm long, and panicles between 10 and 20 cm were selected. This gene was detected at a low level during the seedling stage, with transcripts increasing as the plant matured. In young particles, expression was initially low, and continued to decline as these organs matured. In the leaf organ, this gene was strongly expressed. Semi-quantitative RT-PCR analysis of leaves at four developmental stages confirmed the RNA gel blot analysis (FIG. 6b). The OsMADS50 transcript was detected at all four stages, with the expression level slightly increasing in 49-day-old plants compared with 20-day-old plants. The transcripts of Hd3a, OsMADS14, OsMADS15, and OsMADS18 increased gradually, reaching a maximum at 80 days.

Figure 6:
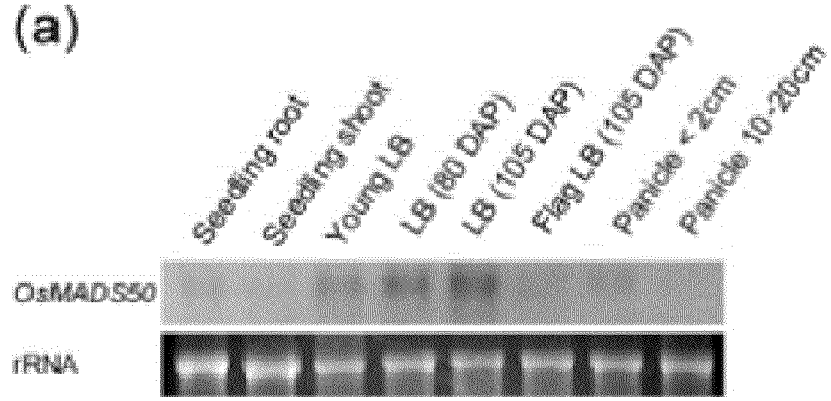
FIG. 6 shows the result of the expression profile of OsMADS50 and other flowering regulators, wherein (a) shows the expression profile of OsMADS50 in various organs; and (b) shows the expression profile of flowering-time regulators in various developmental stages of leaf.
Figure 6:
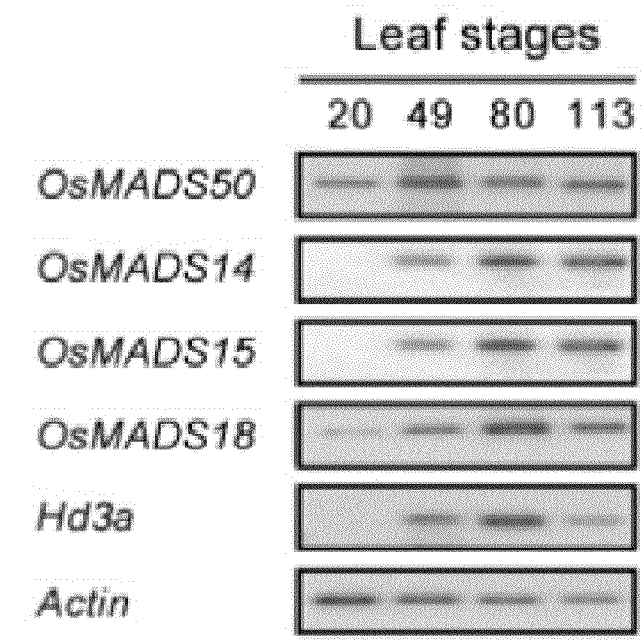

FIG. 6 shows the expression profiles of OsMADS50 and the other flowering-time regulators. FIG. 6a shows the result of RNA gel blot analysis, with 15 μg of total RNA used in each sample, and the KC region of OsMADS50 serving as a probe. At the bottom are the control ribosomal RNAs. From left, seedling roots and shoots 7 days after germination, young leaf blades (LBs) at the 9 to 10 leaf stage (35 days after planting; DAP), LBs 80 DAP, LBs 105 DAP, flag LBs 105 DAP, panicles <2 cm long, and panicles between 10 and 20 cm were shown. The plants flowered 90 DAP. FIG. 6b shows the result of RT-PCR analyses of the putative flowering-time regulators at various developmental stages. WT plants were grown under short-day conditions (10 h light/14 h dark, 30° C.) in the growth chamber, and LBs were sampled 20, 49, 80 and 113 DAP. All samples were harvested 6 h after the light was turned on. Days to flowering were 87.

The expression analyses have revealed that this gene acts early in plant development, being more abundantly expressed in the vegetative organs but decreasing to a very low level during the formation of floral organs.

EXPERIMENTAL EXAMPLE 2

Figure 7:
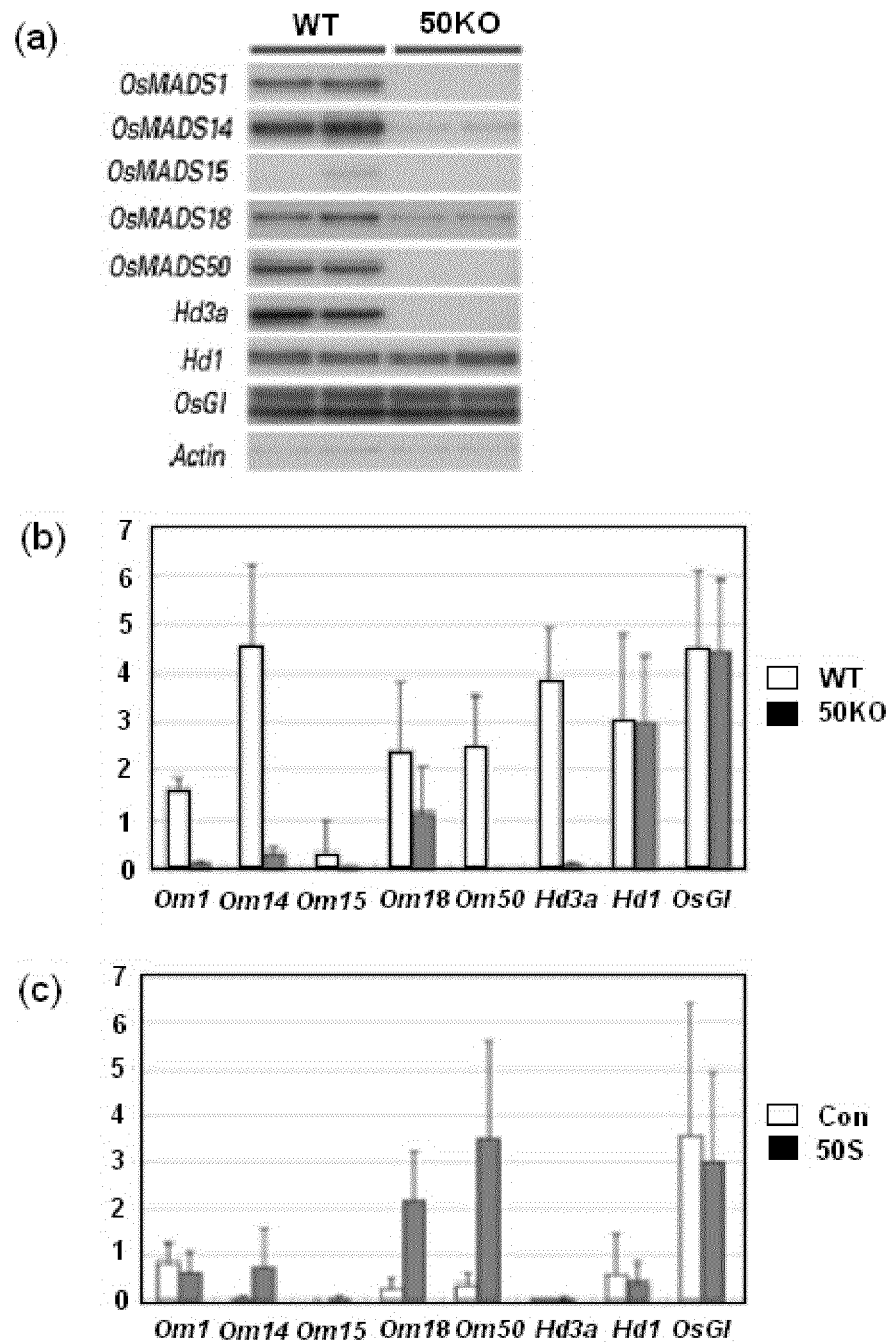
FIG. 7 shows the result of analysis of changes of expression of flowering regulators in an OsMADS50 KO mutant and an OsMADS50 overexpressed mutant, wherein (a) shows the result of RT-PCR in the OsMADS50 KO mutant; and (b) shows a schematic representation of the result of RT-PCR obtained above in (a); and (c) shows the result of RT-PCR in the OsMADS50 overexpressed mutant.

Expression Analysis for Flowering-time Regulators Including OsMADS50 in OsMADS50 Suppressed or Overexpressed Plants To further investigate the role of OsMADS50, the alterations of expression of OsMADS50 KO mutants and OsMADS50 overexpressed plants were analyzed, and the results are shown in FIG. 7. In the OsMADS50 KO plants prepared in Example 1, RT-PCR analyses were carried out for Hd1, Hd3a, and OsGI, all of which control flowering-time in the photoperiod pathway. Four MADS-box genes (OsMADS1, OsMADS14, OsMADS15, and OsMADS18) that appear to be involved as well were also examined. In these experiments, expression of Hd1 and OsGI was not changed in the OsMADS50 knockout plants (FIG. 7). Interestingly, the Hd3a transcript was not detectable in the OsMADS50 KO mutant, suggesting that Hd3a is downstream of OsMADS50. Expression levels of all the MADS-box genes were significantly decreased in the OsMADS50 KO mutant plants, although the degree of reduction for OsMADS18 transcript was not as significant as for the other genes.

The expression levels of regulatory genes in the leaves of regenerating ubi:OsMADS50 plants were tested (FIG. 7c). These plants flowered a few weeks after being transferred to the regeneration media. In contrast to the KO plants, the levels of OsMADS14 and OsMADS18 transcripts were increased in the ubi:OsMADS50 plants while those of OsMADS1, OsGI, and Hd1 were not significantly changed. Expression levels of OsMADS15 and Hd3a were too low to determine any changes in their transcripts.

FIG. 7 shows the expression profiles of MADS-box genes and photoperiod pathway genes in OsMADS50 KO and ubi:OsMADS50 leaves. FIG. 7a shows the results of RT-PCR analyses in OsMADS50 KO leaves. Seventy-three (73) days after planting, leaf blades were harvested 2 h before sunset from KO plants. After RT-PCR, DNA gel blot analyses were performed with specific probes. Two independent WT segregants and two independent OsMADS50 KO plants were examined. FIG. 7b shows a schematic representation of RT-PCR results in OsMADS50 KO plants. DNA band intensity was measured and normalized against the actin transcript level. Results are an average of three independent experiments for each plant. Average values of two WT and two KO plants are represented. Bars, SDs. FIG. 7c shows the expression profiles in ubi:OsMADS50 plants. Leaf blades were sampled from transgenic plants overexpressing OsMADS50, and control plants, and were assayed for transcript levels of genes by quantitative RT-PCR analyses. Data are average of two to three independent samples. Con: T1 control transformed with empty vector; 5OS: Ubi:OsMADS50 leaves. Bars, SDs. PCR primers and number of cycles for amplification of each gene are listed in Table 1 below.

ing-time regulators such as OsMADS14 or OsMADS15 to control the expression thereof, whereas it acts in parallel (independently) or downstream of Hd1 or OsGI.

EXPERIMENTAL EXAMPLE 3

Figure 8:
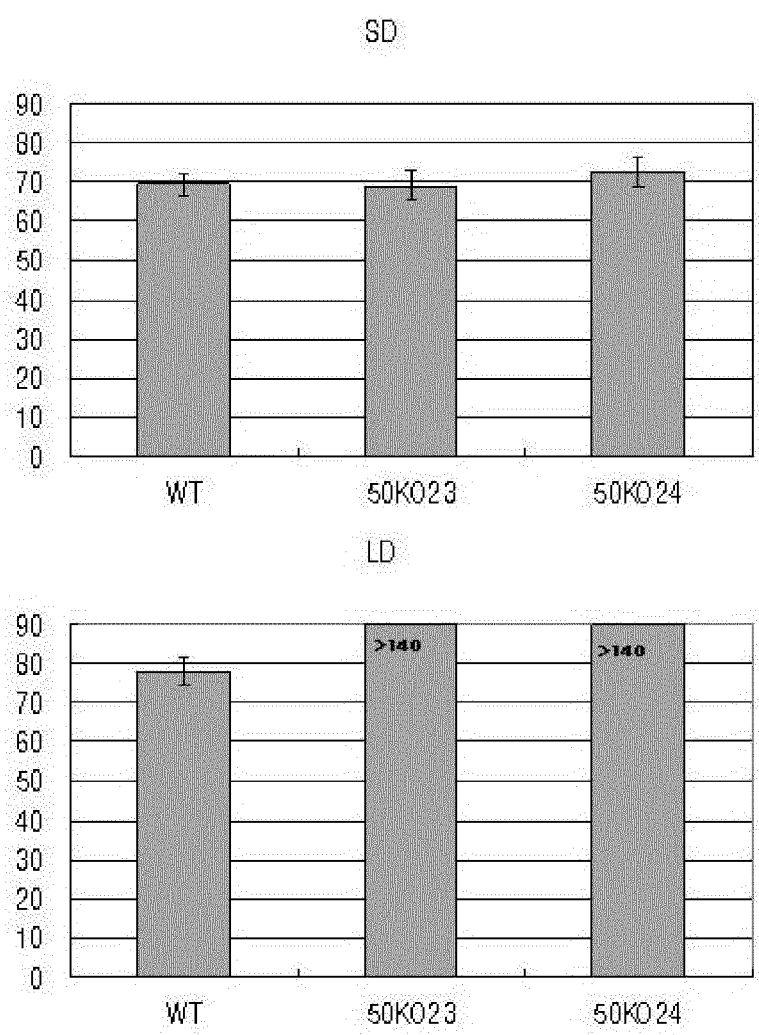
FIG. 8 is a graph showing the flowering-time of OsMADS50 KO plants under long-day and short-day conditions.

Analysis of Flowering-time of OsMADS50 KO Mutant Depending on Photoperiod Conditions The flowering-times in two independent T2 OsMADS50 KO lines (named 50KO23 and 50KO24, respectively) isolated from T-DNA inserted lines of Example 1, and in wild-type lines (control) were observed under various photoperiod conditions. The photoperiod conditions were short-day conditions (SD: 10 h L/14 h D) and long-day conditions (LD: 14 h L/10 h D). The result of the above observation was shown in FIG. 8. As shown in FIG. 8, under short-day conditions, no outstanding difference was observed between the control and the OsMADS50 KO lines. However, under long-day conditions, the control flowered about 78 days after planting, while the OsMADS50 KO lines did not flower until 140 days after planting. Accordingly, it confirms that the OsMADS50 is a flowering-time regulator which acts under long-day conditions.

EXPERIMENTAL EXAMPLE 4

Analysis of the Expression Pattern of Flowering-time Regulators in OsMADS50 KO Lines Sixty (60) days after planting, leaf blades were sampled from the OsMADS50 KO lines of Example 1 and wild-type

TABLE 1

Primers and PCR cycles used in RT-PCR analyses

| Gene | Forward primer | Reverse primer | PCR cycles 50 KO[a] | PCR cycles 50 S[b] |
|---|---|---|---|---|
| OsMADS1 | tccatatgtcctggcaagat | aagagagcacgcacgtactt | 28 | 32 |
| OsMADS14 | tcctatgcagaaaaggtcctt | ggacgaagccaaaatatacac | 36 | 36 |
| OsMADS15 | gctcttatttcagctgaa | tcatatgtagcctgtagg | 36 | 36 |
| OsMADS18 | ccaaactggatgcacttcag | atcaatatcgctggaagatg | 23 | 32 |
| OsGI | tggagaaaggttgtggatgc | gatagacggcacttcagcagat | 23 | 26 |
| Hd1 | ttctcctctccaaagattc | catacgcctttcttgtttca | 28 | 26 |
| Hd3a | atggccggaagtggcagggac | atcgatcgggatcatcgttag | 36 | 36 |
| Actin | gtatccatgagactacatacaact | tactcagccttggcaatccaca | 23 | 26 |

[a]PCR cycles used for OsMADS50 KO plants and WT segregants.
[b]PCR cycles used for ubi: OsMADS50 plants and WT controls.

Figure 9:
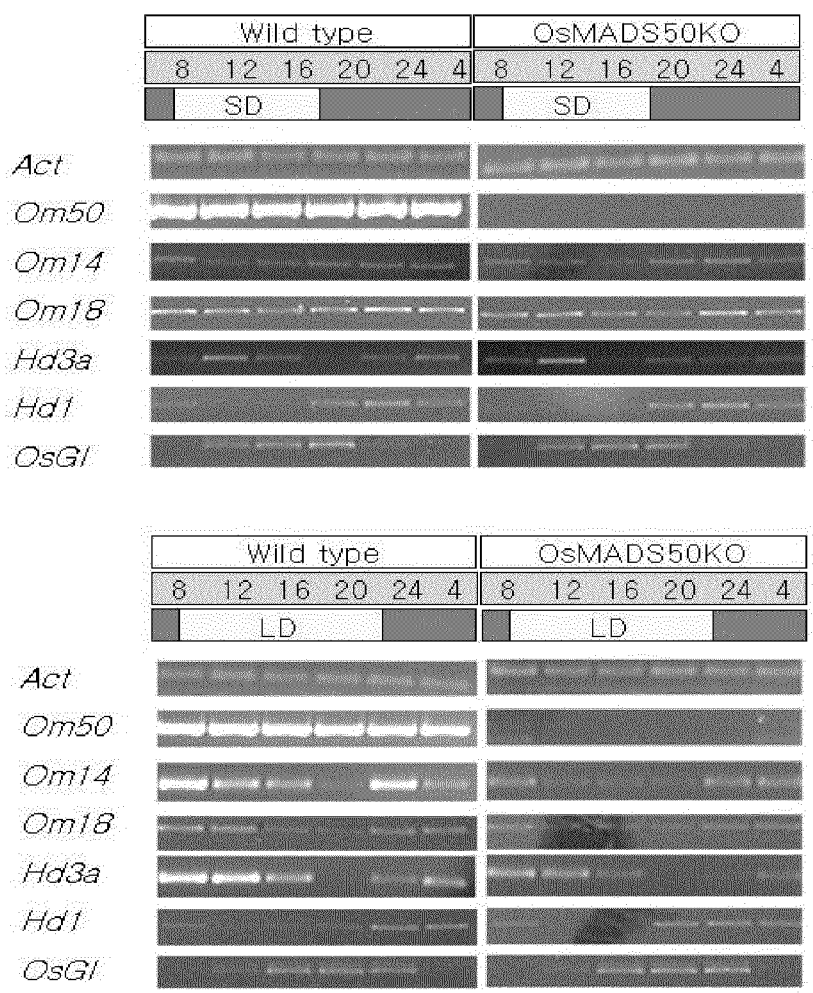
FIG. 9 shows the expression pattern of flowering-time regulators in the OsMADS50 KO plant.

In RT-PCT for OsMADS50 KO mutants, it was observed that the expressions of OsMADS1, OsMADS14, OsMADS15, OsMADS18 and Hd3a are significantly decreased compared with wild-type (WT), while no outstanding change was observed in the expression of Hd1 and OsGI. Further, in RT-PCT for an OsMADS50 overexpressed mutant, it was observed that the expressions of OsMADS14 and OsMADS18 increased, whereas no outstanding change was observed in the expressions of OsMADS1, OsMADS15, Hd3a, Hd1 and OsGI. From the above results, it is presumed that the OsMADS50 gene acts upstream of the other flower-lines (control). The expressions of the flowering-time regulators such as OsMADS14, OsMADS18, Hd3a, Hd1 and OsGI, in addition to OsMADS50 were analyzed in the obtained samples, and the result is shown in FIG. 9. As shown in FIG. 9, under long-day conditions, the expression of OsMADS14, OsMADS18 and Hd3a were downregulated in the OsMADS50 KO lines, while the expression of Hd1 and OsGI were not considerably changed. Therefore, it confirms that OsMADS50 is an upstream flowering-time regulator of other regulators such as OsMADS14, OsMADS18 and Hd3a.

EXAMPLE 5

Isolation of OsMADS51, OsMADS56, OsTRX1 and OsVIN2

Among the T-DNA tagging lines prepared as disclosed in Example 1, the lines wherein T-DNA is respectively inserted in OsMADS51, OsMADS56, OsTRX1 and OsVIN2, were isolated.

The nucleotide sequence of the OsMADS51 gene was isolated and identified, then shown in SEQ ID NO: 2. The OsMADS51 gene has been registered in the NCBI database as AB003327. However, only the expression profiles in various organs is known, while its function is yet unknown (Shinozuka et al., 1999). In the present invention, this gene was isolated through PCR and its function was determined.

Furthermore, the nucleotide sequence of the OsMADS56 gene was isolated and identified, then shown in SEQ ID NO: 3. This was isolated through PCR and its nucleotide sequence was registered in the NCBI database as AY345224 by the present inventors.

Additionally, the nucleotide sequences of OsTRX1 and OsVIN2 are shown in SEQ ID NO: 4 and SEQ ID NO: 5.

EXPERIMENTAL EXAMPLE 5

Analysis of Flowering-time in OverExpressed or Suppressed Mutants of OsMADS51, OsMADS56, OsTRX1 and OsVIN2

To further examine the functional role of the genes isolated in Example 5 in regulating the flowering-time, a transgenic nice was prepared which overexpresses the sense construct of OsMADS51 or OsMADS56 using the pGA1611 vector (AY373338) prepared in the laboratory, wherein constitutive expression was induced using the maize ubiquitin (ubi) promoter [see, FIG. 5(a)]. It was observed that in the OsMADS51 overexpressed mutants, the flowering-time was accelerated by 1 to 2 weeks under field conditions, while in the OsMADS56 overexpressed mutants, the flowering-time was delayed by 1 to 2 weeks under field conditions (see FIG. 12).

Figure 11:
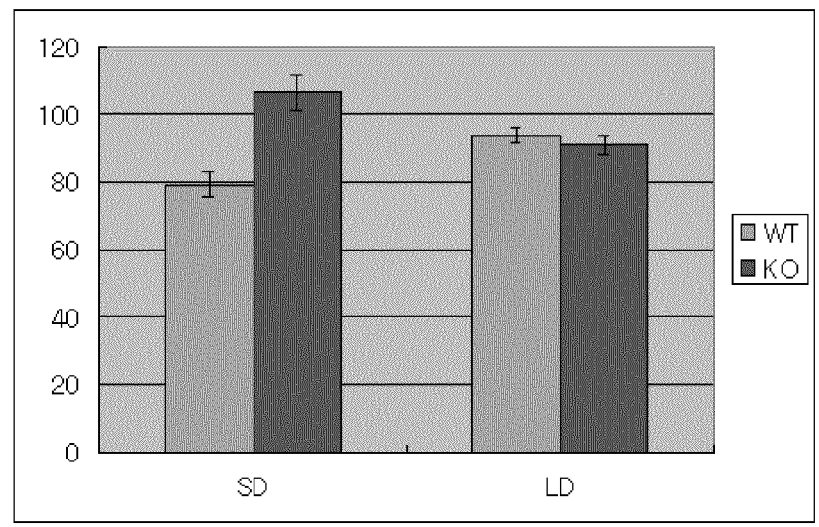
FIG. 11 is a graph showing delay of flowering-time in OsMADS51 KO plants.
Figure 12:
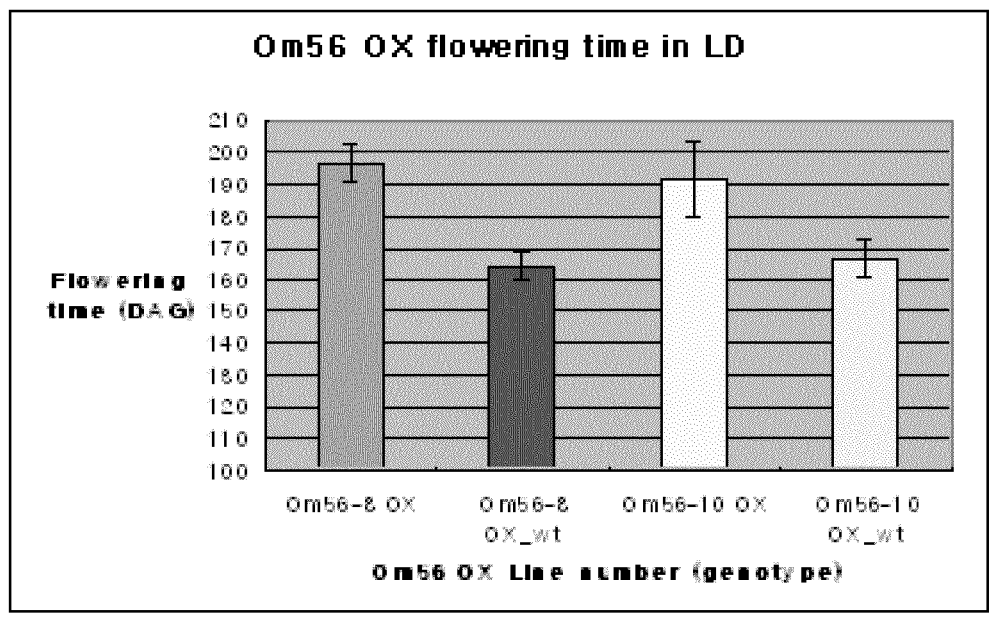
FIG. 12 is a graph showing delay of flowering-time in OsMADS56 overexpressed plants.

In the experiments under short-day conditions (SD: 10 h L/14 h D) and long-day conditions (LD: 14 h L/10 h D), interestingly, it was observed that in OsMADS51 KO mutants, the flowering-time was delayed by about one month only under short-day conditions (see FIG. 11), and in OsMADS56 overexpressed mutants, the flowering-time was delayed only under long-day conditions (see FIG. 12). In case of the OsMADS56 mutants, two independent lines (named Nos. 8 and 10, respectively) were tested. Furthermore, the OsMADS51 KO line showed a delayed-aging phenotype under field conditions.

Figure 10:
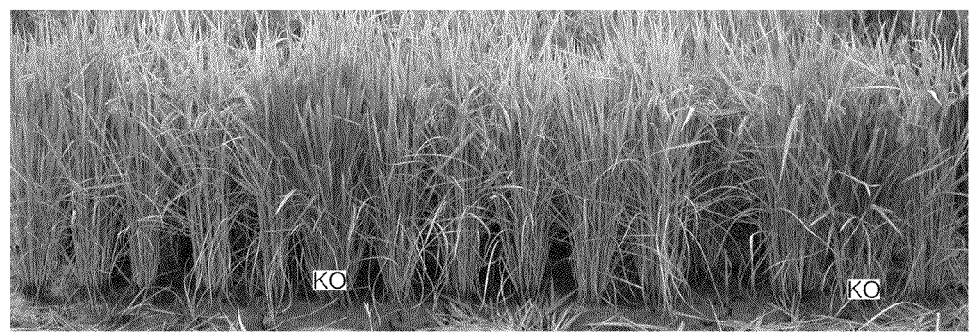
FIG. 10 shows the late-flowering phenotype of OsTRX1 KO plants.
Figure 13:
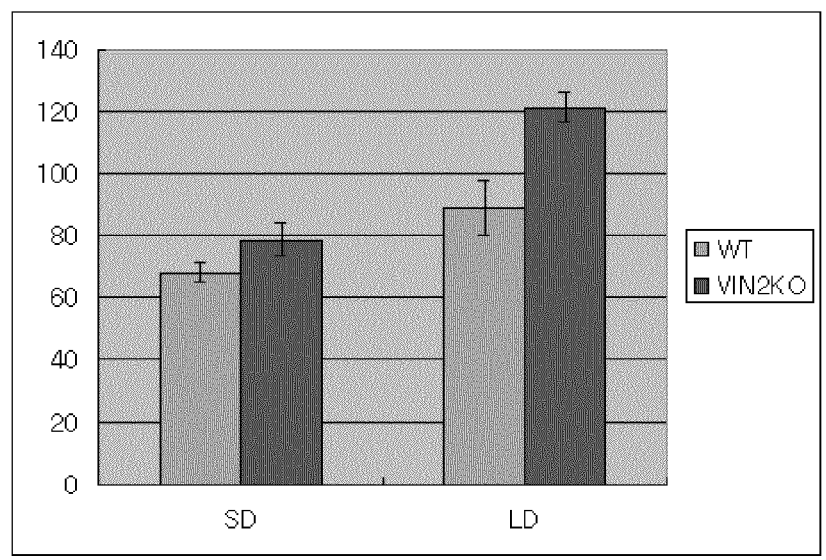
FIG. 13 is a graph showing delay of flowering-time in OsVIN2 KO plants.

Furthermore, OsTRX1 and OsVIN2 were respectively knocked-out to prepare OsTRX1 KO lines and OsVIN2 KO lines by the same method as that of the OsMADS50 KO line. The OsTRX7 KO lines showed a late-flowering phenotype late by at least one month under field conditions (see FIG. 10), and the OsVIN2 KO lines showed a late-flowering phenotype late by about 32 days under long-day conditions, and about 10 days under short-day conditions (see FIG. 13).

EXAMPLE 6

Isolation of OsCOL4

Figure 14:
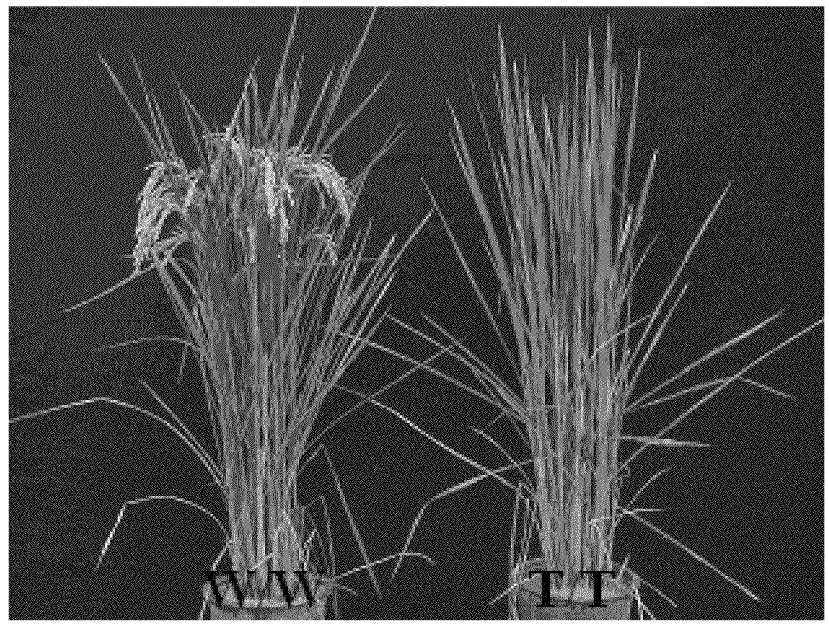
FIG. 14 shows the late-flowering phenotype of OsCOL4 overexpressed plaints.
Figure 15:
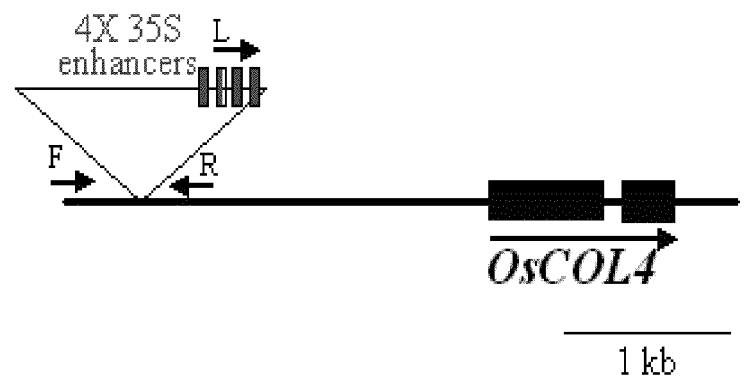
FIG. 15 is a schematic view showing that T-DNA containing the 35S enhancer is inserted in the promoter region of OsCOL4.
Figure 16:
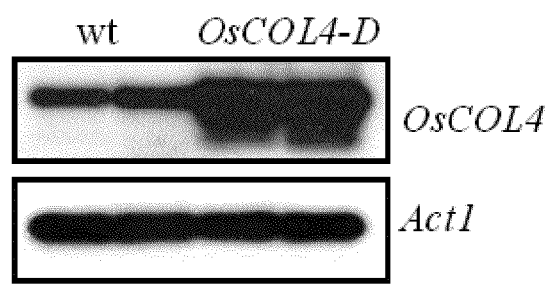
FIG. 16 is an electrophoresis result showing overexpression of OsCOL4.

To research further flowering-time regulators, lines exhibiting alteration in flowering-time were screened from the rice mutant population wherein an activation tagging vector (pGA2715; Joeng et al, *Plant Physiology*, December 2002, Vol. 130, pp. 1636-1644) is inserted. Among them, the line named 1B-00735 is a late-flowering phenotype late by at least 15 days compared with the wild-type line (see FIG. 14). The analysis of the genotype of the mutant line revealed that T-DNA is inserted in the promoter region of OsCOL4 gene, and the OsCOL4 gene is overexpressed due to 35S enhancers present in T-DNA (see FIGS. 15 and 16). The T-DNA insertion position in the OsCOL4 gene and the function of the 35S enhancers present in T-DNA are shown in FIG. 15. Based on such results, the OsCOL4 gene was isolated and its nucleotide sequence is shown in SEQ ID NO: 11.

EXPERIMENTAL EXAMPLE 6

Analysis of Flowering-time in OsCOL4 Overexpressed or Suppressed Mutants

Figure 17:
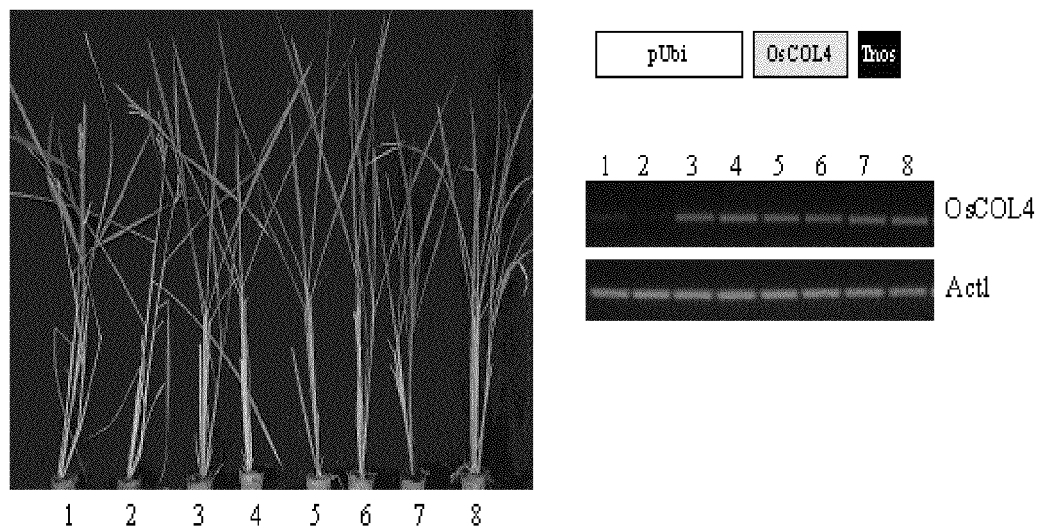
FIG. 17 is a photograph showing the late-flowering phenotype of OsCOL4 overexpressed plants.

As disclosed above, T-DNA was inserted in the promoter region of the OsCOL4 gene, and the obtained OsCOL4 overexpressed mutants exhibited a late-flowering phenotype caused by the 35S enhancers present in T-DNA. Furthermore, such late-flowering due to the overexpression (activation tagging) of the OsCOL4 gene was re-confirmed by observing that the mutant, wherein the OsCOL4 gene is operably linked to a strong promoter, pUbi, to be overexpressed, showed delayed-flowering phenotype delayed by about 2 week (see FIG. 17). In FIG. 17, Act1 indicates the actin gene of rice used as a control.

Figure 18:
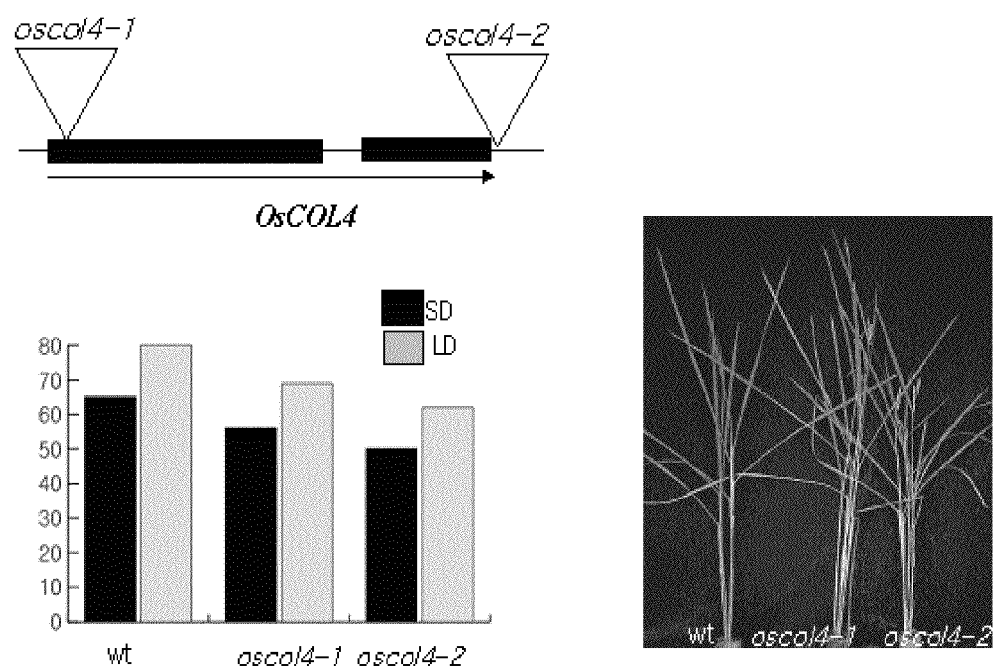
FIG. 18 is a photograph showing the early-flowering phenotype of OsCOL4 suppressed plants.

In contrast, the OsCOL4 suppressed mutant line exhibited an early-flowering phenotype early by about 2 weeks (see FIG. 18). Such an OsCOL4 suppression was confirmed in both the mutant wherein T-DNA is inserted in the first exon of the OsCOL4 gene (OsCOL4-1 shown in FIG. 18) and the mutant wherein T-DNA is inserted in the 3'UTR region (OsCOL4-2 shown in FIG. 18).

Figure 19:
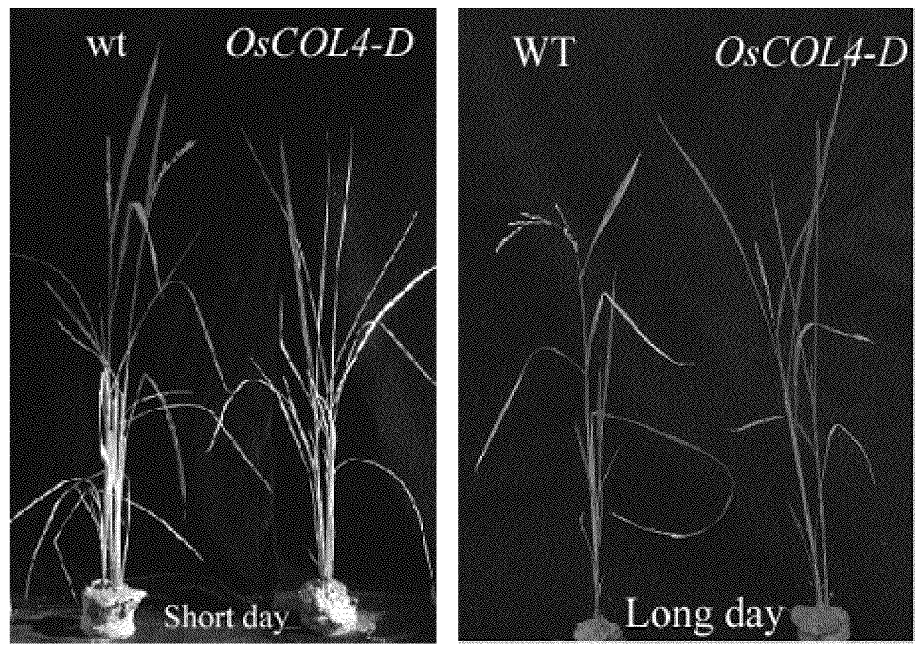
FIG. 19 shows the flowering-time alteration in OsCOL4 suppressed plants under long-day, short-day, and field conditions.
Figure 19:
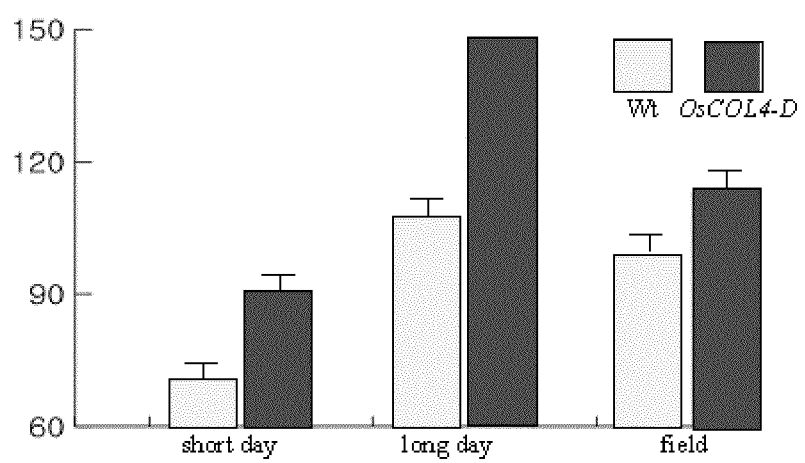

In experiments with changing photoperiod conditions, the OsCOL4 activation tagging lines displayed late flowering compared with wild-type lines regardless of the photoperiod conditions, while the OsCOL4 suppressed lines displayed early flowering regardless of the photoperiod conditions (see FIG. 19). In FIG. 19, 'OsCOL4-D' indicates the OsCOL4 activation tagging mutant.

EXAMPLE 7

Isolation of OsCOL8

The OsCOL8 gene is a CONSTANS-like gene present in rice, and is similar to VRN2 which regulates flowering-time in wheat by vernalization treatment. Through the analysis of T-DNA inserted mutant line according to the present invention, the OsCOL8 gene was isolated as a flowering-time regulator inducing alteration in flowering-time by T-DNA insertion therein, and its nucleotide sequence is shown in SEQ ID NO: 7.

EXPERIMENTAL EXAMPLE 7

Analysis of Flowering-time in OsCOL8 Suppressed Mutant

Figure 20:
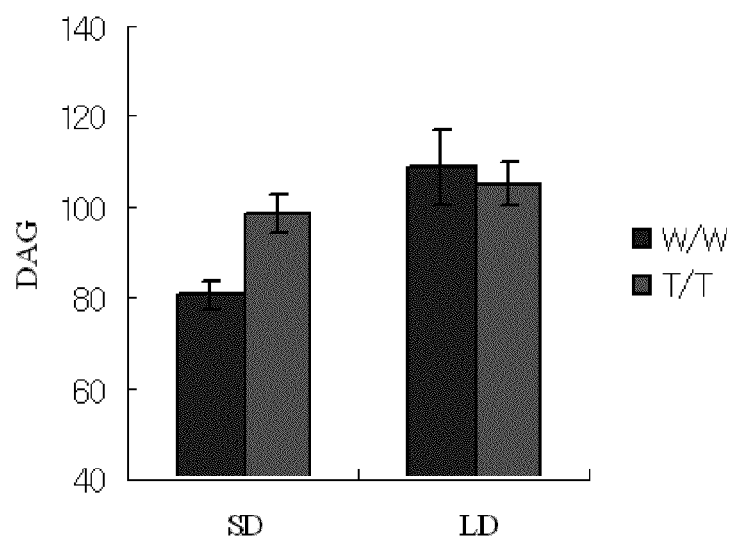
FIG. 20 shows the flowering-time alteration in OsCOL8 suppressed plants under long-day, and short-day conditions.

To examine the regulation in flowering-time by the OsCOL8 gene, the mutant wherein T-DNA is inserted in the first exon of the OsCOL8 gene was analyzed. The result of the analysis revealed that the flowering-time in the mutant is similar to the wild-type under long-day conditions, while it was delayed under short-day conditions (see FIG. 20). Accordingly, the OsCOL8 gene is expected to work as a flowering activator under short-day conditions.

EXAMPLE 8

Isolation of OsMADS14

Four (4) genes have been known as rice orthologs of APETALA1 (AP1) of *Arabidopsis* (APETALA1-like gene in rice) involved in formation of floral organs and regulation of flowering-time, each of which was named OsMADS14, OsMADS15, OsMADS18, and OsMADS20, respectively. Among them, the OsMADS14 gene was the first to be cloned as a binding partner of the OsMADS6 protein, however its specific function has been unknown. In the present example, based on the observation that the flowering-time is altered when a DNA fragment such as T-DNA is inserted in the OsMADS14 gene, the gene was isolated as a flowering-time regulator. The nucleotide sequence of the gene is shown in SEQ ID NO: 8.

EXPERIMENTAL EXAMPLE 3

Analysis of Flowering-time in OsMADS14 Suppressed or Overexpressed Mutants

Figure 21:
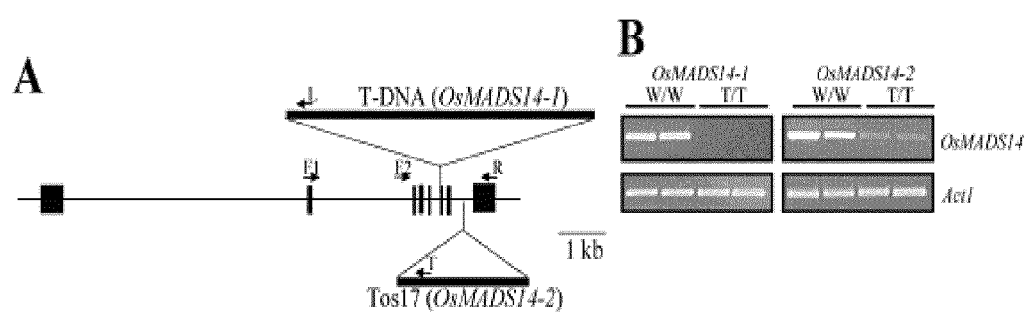
FIG. 21 shows the structure of T-DNA inserted OsMADS14 and the expression profile thereof.

The result of analysis for the mutants wherein T-DNA or Tos17 is inserted inside the OsMADS14 gene showed no outstanding change in flowering-time and floral development (see FIG. 21). The insertion positions of T-DNA and Tos17 in the OsMADS14 gene are shown in FIG. 21. The above result suggests that other genes besides the OsMADS14 gene work redundantly.

The gene wherein the stop codon was artificially inserted between the last K domain and C domain of the OsMADS14 gene was introduced into the pGA1611(AY373338) vector to induce overexpression of OsMADS14 partial protein wherein the terminal region containing the C domain is deleted. The observation of overexpression of OsMADS14 partial protein wherein the terminal region containing the C domain is deleted as above showed that the flowering-time is accelerated by about one month under short-day conditions, and the flowering-time is delayed by about two weeks under long-day conditions. Such a result reveals that the overexpression of the 3, region deleted OsMADS14 partial gene results in flowering activation under short-day conditions, and in flowering inhibition by interaction with other flowering activators under long-day conditions.

---

We claim

1. A method to delay flowering in a plant comprising the step of inducing overexpression of OsCOL4 gene having the nucleotide sequence of SEQ ID NO: 11, wherein the step of inducing overexpression of OsCOL4 gene comprises the step of introducing into a plant a construct comprising SEQ ID NO: 11 operably linked to a strong promoter or wherein an enhancer element is inserted into the promoter region of SEQ ID NO: 11.

2. The method according to claim 1, wherein the plant is rice.

* * * * *

SEQUENCE LISTING

```
<160> NUMBER OF SEQ ID NOS: 24

<210> SEQ ID NO 1
<211> LENGTH: 744
<212> TYPE: DNA
<213> ORGANISM: Artificial Sequence
<220> FEATURE:
<223> OTHER INFORMATION: cDNA sequence of OsMADS50

<400> SEQUENCE: 1
gttggttcat cggcgatcga agatggtgcg ggggaagacg cagatgaagc ggatagagaa        60
ccccacgagc cgccaggtca ccttctccaa gcgccgcaac ggcctgctca agaaggcctt       120
cgagctctcc gtcctctgcg acgccgaggt cgcgctcatc gtcttctccc cgcgcggcaa       180
gctctacgaa ttcgccagcg ccagtacgca gaaaacaatt gaacgctata ggacgtatac       240
aaaggaaaat atcggcaaca agacagtaca gcaagatata gagcaagtaa aagctgacgc       300
tgatggtttg gcaaagaaac ttgaagctct tgaaacttac aaaagaaaac tgctgggtga       360
aaagttggat gaatgttcta ttgaagaact gcatagcctg gaggtcaagc tggagagaag       420
cctcattagc atcaggggaa ggaagacaaa gctgcttgag gagcaggttg ccaaactgag       480
agagaaggag atgaagctgc gcaaggacaa tgaagagtta cgcgaaaagt gtaagaatca       540
gcctcccttg tctgctcctt tgactgtccg ggccgaagat gagaacccgg accgtaacat       600
caacaccacc aacgacaaca tggatgtcga aactgagcta ttcatagggc tgcctggcag       660
aagtcgctcc agcggcggtg ctgcagaaga tagccaagcg atgccccatt cttaagtaac       720
aggccaggaa taagctggat ctct                                              744

<210> SEQ ID NO 2
<211> LENGTH: 230
<212> TYPE: PRT
<213> ORGANISM: Artificial Sequence
<220> FEATURE:
<223> OTHER INFORMATION: OsMADS50 protein
```

<400> SEQUENCE: 2

```
Met Val Arg Gly Lys Thr Gln Met Lys Arg Ile Glu Asn Pro Thr Ser
1               5                   10                  15

Arg Gln Val Thr Phe Ser Lys Arg Arg Asn Gly Leu Leu Lys Lys Ala
            20                  25                  30

Phe Glu Leu Ser Val Leu Cys Asp Ala Glu Val Ala Leu Ile Val Phe
        35                  40                  45

Ser Pro Arg Gly Lys Leu Tyr Glu Phe Ala Ser Ala Thr Gln Lys
    50                  55                  60

Thr Ile Glu Arg Tyr Arg Thr Tyr Thr Lys Glu Asn Ile Gly Asn Lys
65                  70                  75                  80

Thr Val Gln Gln Asp Ile Glu Gln Val Lys Ala Asp Ala Asp Gly Leu
            85                  90                  95

Ala Lys Lys Leu Glu Ala Leu Glu Thr Tyr Lys Arg Lys Leu Leu Gly
            100                 105                 110

Glu Lys Leu Asp Glu Cys Ser Ile Glu Glu Leu His Ser Leu Glu Val
            115                 120                 125

Lys Leu Glu Arg Ser Leu Ile Ser Ile Arg Gly Arg Lys Thr Lys Leu
130                 135                 140

Leu Glu Glu Gln Val Ala Lys Leu Arg Glu Lys Glu Met Lys Leu Arg
145                 150                 155                 160

Lys Asp Asn Glu Glu Leu Arg Glu Lys Cys Lys Asn Gln Pro Pro Leu
                165                 170                 175

Ser Ala Pro Leu Thr Val Arg Ala Glu Asp Glu Asn Pro Asp Arg Asn
            180                 185                 190

Ile Asn Thr Thr Asn Asp Asn Met Asp Val Glu Thr Glu Leu Phe Ile
            195                 200                 205

Gly Leu Pro Gly Arg Ser Arg Ser Ser Gly Gly Ala Ala Glu Asp Ser
        210                 215                 220

Gln Ala Met Pro His Ser
225                 230
```

<210> SEQ ID NO 3
<211> LENGTH: 495
<212> TYPE: DNA
<213> ORGANISM: Artificial Sequence
<220> FEATURE:
<223> OTHER INFORMATION: cDNA sequence of OsMADS51

<400> SEQUENCE: 3

```
atggcgcgga gggggagagt gcagctgagg cggatcgagg acaaggcgag ccggcaggtg      60
cggttctcca agaggagggc ggggctgttc aagaaggcgt tcgagctcgc cctgctctgc     120
gacgtggagg tggcgctcct cgtcttctcc ccgtcggca agctctacga gtactcctcc     180
tccagcattg aaggtaccta tgatcgctat cagcaattcg ctggagccag agagacctg     240 aacgaaggaa gtacaagcat caacagtgat gaaaatgcaa gtatacactc caggcttagg     300
gacataacgg cctggtctct ccaaaacaat gctgacgagt cggatgctaa tcagctagag     360
aaactggaga aactgctgac aaatgctttg agggatacga atcaaagaa gatgttggca     420 aaacaaaatg gtgaagggag taggagcaga gcaaactcca gtggctctag ggggcaggag     480
gaaggaagtg catga                                                      495
```

<210> SEQ ID NO 4
<211> LENGTH: 164
<212> TYPE: PRT

<213> ORGANISM: Artificial Sequence
<220> FEATURE:
<223> OTHER INFORMATION: OsMADS51 protein

<400> SEQUENCE: 4

```
Met Ala Arg Arg Gly Arg Val Gln Leu Arg Arg Ile Glu Asp Lys Ala
1               5                  10                  15

Ser Arg Gln Val Arg Phe Ser Lys Arg Arg Ala Gly Leu Phe Lys Lys
            20                  25                  30

Ala Phe Glu Leu Ala Leu Leu Cys Asp Val Glu Val Ala Leu Leu Val
        35                  40                  45

Phe Ser Pro Val Gly Lys Leu Tyr Glu Tyr Ser Ser Ser Ile Glu
    50                  55                  60

Gly Thr Tyr Asp Arg Tyr Gln Gln Phe Ala Gly Ala Arg Arg Asp Leu
65                  70                  75                  80

Asn Glu Gly Ser Thr Ser Ile Asn Ser Asp Glu Asn Ala Ser Ile His
                85                  90                  95

Ser Arg Leu Arg Asp Ile Thr Ala Trp Ser Leu Gln Asn Asn Ala Asp
            100                 105                 110

Glu Ser Asp Ala Asn Gln Leu Glu Lys Leu Lys Leu Leu Thr Asn
        115                 120                 125

Ala Leu Arg Asp Thr Lys Ser Lys Lys Met Leu Ala Lys Gln Asn Gly
    130                 135                 140

Glu Gly Ser Arg Ser Arg Ala Asn Ser Ser Gly Ser Arg Gly Gln Glu
145                 150                 155                 160

Glu Gly Ser Ala
```

<210> SEQ ID NO 5
<211> LENGTH: 693
<212> TYPE: DNA
<213> ORGANISM: Artificial Sequence
<220> FEATURE:
<223> OTHER INFORMATION: cDNA sequence of OsMADS56

<400> SEQUENCE: 5

```
atggtgcggg ggaggacgga gctgaagcgg attgagaacc cgacgagccg gcaggtgacc      60
ttctccaagc gccggaatgg cctcctcaag aaggcgttcg agctctccgt cctctgcgac     120
gccgaggtcg ccctcatcgt cttctccccc cgcggccgcc tctacgagtt cgccagcgcc     180
cccagcctac agaaaaccat cgaccgctat aaagcataca caaggatca tgtcaacaat     240 aagacaattc aacaagatat ccagcaagtc aaagatgata ctttaggctt ggccaagaaa     300
cttgaagctc ttgatgagtc cagacggaaa atattgggag aaaatttaga aggatgctct     360
attgaagaac tgcgtggtct agaaatgaaa cttgagaaga gcctccacaa cataagacta     420
aagaagaccg agcttctgga gcggcagata gccaagctga agagaagga gcggactttg     480 cttaaagaca cgaaaatttt acgcggaaag catcgcaacc ttgaggctgc ggcgctggtg     540
gctaaccaca tgacgacgac gacggcgccg gcggcgtggc cgcgggacgt gcctatgacg     600
agcagcacag ccggcgccat ggacgtggag actgatctgt acattggatt gcccggcact     660
gagcgctcct ccaaccggtc ggagacaggt tga                                  693
```

<210> SEQ ID NO 6
<211> LENGTH: 230
<212> TYPE: PRT
<213> ORGANISM: Artificial Sequence
<220> FEATURE:
<223> OTHER INFORMATION: OsMADS56 protein

<400> SEQUENCE: 6

```
Met Val Arg Gly Arg Thr Glu Leu Lys Arg Ile Glu Asn Pro Thr Ser
1               5                   10                  15

Arg Gln Val Thr Phe Ser Lys Arg Arg Asn Gly Leu Leu Lys Lys Ala
            20                  25                  30

Phe Glu Leu Ser Val Leu Cys Asp Ala Glu Val Ala Leu Ile Val Phe
        35                  40                  45

Ser Pro Arg Gly Arg Leu Tyr Glu Phe Ala Ser Ala Pro Ser Leu Gln
    50                  55                  60

Lys Thr Ile Asp Arg Tyr Lys Ala Tyr Thr Lys Asp His Val Asn Asn
65                  70                  75                  80

Lys Thr Ile Gln Gln Asp Ile Gln Gln Val Lys Asp Asp Thr Leu Gly
                85                  90                  95

Leu Ala Lys Lys Leu Glu Ala Leu Asp Glu Ser Arg Arg Lys Ile Leu
            100                 105                 110

Gly Glu Asn Leu Glu Gly Cys Ser Ile Glu Glu Leu Arg Gly Leu Glu
        115                 120                 125

Met Lys Leu Glu Lys Ser Leu His Asn Ile Arg Leu Lys Lys Thr Glu
    130                 135                 140

Leu Leu Glu Arg Gln Ile Ala Lys Leu Lys Glu Lys Glu Arg Thr Leu
145                 150                 155                 160

Leu Lys Asp Asn Glu Asn Leu Arg Gly Lys His Arg Asn Leu Glu Ala
                165                 170                 175

Ala Ala Leu Val Ala Asn His Met Thr Thr Thr Ala Pro Ala Ala
            180                 185                 190

Trp Pro Arg Asp Val Pro Met Thr Ser Ser Thr Ala Gly Ala Met Asp
    195                 200                 205

Val Glu Thr Asp Leu Tyr Ile Gly Leu Pro Gly Thr Glu Arg Ser Ser
210                 215                 220

Asn Arg Ser Glu Thr Gly
225                 230
```

<210> SEQ ID NO 7
<211> LENGTH: 3069
<212> TYPE: DNA
<213> ORGANISM: Artificial Sequence
<220> FEATURE:
<223> OTHER INFORMATION: cDNA sequence of OSTRX1

<400> SEQUENCE: 7

```
atggtgatcg cggtggaggg gggcttcgtg cacgaggagg aggaggtgga ccacccaatt     60
cgctacctcc cacttggccg cgtctactcc tcctctgctc cgtgccctct ccccaagaag    120
ccccgctccg ccgaggacgg caagcccccc gtgatcgtct actaccgccg ccgccgtaag    180
aagccgcggg tcgagggggcc acctcccctcg cctgccacag caccaccgat gctgcacccc    240
cgggaggacg acgaggatga ggaggttaca cggcggaagg gttctctcaa gtacgagctg    300
ctgagcctgg ggcaagcccc gcccgcatta ggcggggatg ggaggagcc cgcgcggcgg    360 cgctgcctga ggcgtagcgg aggggctgag aggaggggtt acttctctga acccaagagg    420
cggcagcggc agggcgtgca aaggaagct gcctcctcgg ctgggaggag atggttggag    480
ttggaaattg aggctgcgga tccactggcc tttgtgggat taggatgcaa ggttttctgg    540
cccctcgatg aggattggta caggggttct atcacagggt acaatgaagc gactaagaaa    600
cattccgtaa agtatgatga tggcgaatca gaggacctta acctagctga tgaaaggata    660
```

```
aaatttttcta tttcatctga agaaatgaag tgcaggaact tgaaatttgg aatttccaat      720
ctgaacaaga ggggctatga tgagttgctt gcccttgctg ttagccttca tgattaccaa      780
ggtcttgatc caggtgatct tgtgtgggct aaacttacag gtcatgccat gtggccagct      840
gttgtggtgg atgaatcaaa tgttcctgct aacagggctt tgaagccagg ccgactagat      900
cagtcgatac ttgttcaatt ctttggtact catgattttg ccaggattaa gttgaagcaa      960
gcggtgccct ttctgaatgg ccttctttct tctttgcatc ttaaatgcaa gcaagcacgc     1020
ttctatcgga gtttagaaga agccaaggag tttctctgca cacagcttct cccagaaaat     1080
atgttgcaac tacagaaatc catggaaaag ggcagttctg atgctaattc aataaagat      1140 gtacattctt gtgacaattt atctgaagat aaaacagctg aaagcggagg ggattatgat     1200
gagatgactc caatagaact aggaaatctt cgtgtgagca aattaggtag gatagtaact     1260
gactcagact atttccataa caaaaagcat atatggcctg aagggtatac tgctttcagg     1320
aagttcagat cagtgaaaga tccacatgta gtaatacttt acaaaatgga ggtactgagg     1380
aattcagata taaaagctcg gccattgttt agggtcacat cagaagatgg aacacagatt     1440
gatggctcta ccccaaatac atgttggaag gagatatatt gtagattaaa ggaaaaacag     1500
cgcaatgtgg cctctggatt ggacagagat gttttgtcagg gatctggttc ctatatgttt     1560
ggcttttcaa atccacaaat acggcaactt attcaggagt tacccaatgc aaggtcatgc     1620
ttaaagtatt ttgaaaatgc tggagacacc tttcgtgggt atagagctgt tcatgtaaat     1680
tggaaagatc tagactattg tagtgtttgt gatatggatg aggaatacga agacaatttg     1740
ttcttgcaat gtgataagtg ccgtatgatg gtacatgcta gatgctatgg tgaactcgaa     1800
ccattgaatg gagtcctttg gctttgcaac ctgtgtcgac ctgaggcgcc tcgtgtttct     1860
ccacgatgct gtctttgtcc agtaacaggg ggcgcaatga aaccaacaac agatggtcgt     1920
tgggctcatc ttgcatgtgc tatatggatt cctgaaactt gcttaaaaga tgtgaagaga     1980
atggaaccga ttgatggatt gagcagaatc aacaaggacc gctggaaact tctatgcagc     2040
atttgcggag ttgcttatgg agcttgcata cagtgttctc atcctacctg tcgtgttgca     2100
tatcaccctc tttgtgcacg tgctgctgat ctttgtgttg agcttgaaga tgatgacaaa     2160
atccacctca tgttacttga tgaggatgag gacccatgta ttcgtctact ttcatactgc     2220
aagaagcaca gacaaccatc gactgaacgt ccatctcttg aaagtaaccct tgctaagcct     2280 gctgtggtag ttcagacaga tgcagttcca ccatccggtt gtgcaaggac tgaaccttat     2340
aatatccatg ggagaagggg ccaaaagcaa cctcaagtta tggctaccgc ttctgtaaaa     2400
cgtttatatg tagagaatat gccttatatt gttagtggtt tctgccaaaa tagagtaggc     2460
catgatgcta tcagtgaacc aattcaatca gttggcttt tggatgttgc acatcaagaa     2520
gctgttggca acgtgtcttc tatgattgaa aagtataaaa gcatgaaggc tacattcagg     2580
aggagactag cttttggaaa gtcaagaatt catggatttg gtgtctttgc aaaggtttcg     2640
cacaaggcag gcgacatgat gattgagtac atcggagagc tcgtcaggcc accaatatca     2700
gacattagag agcggcgcat atacaactct ttagtgggtg ctgggacgta catgttcagg     2760
atagatgatg agcgtgttat agatgctacg cgggcaggaa gcattgccca tttaattaat     2820
cattcttgtg agccgaattg ttattcacgc gtcataagtg ttctcgggga tgagcatatc     2880 atcattttg caaagcggga tataaatcca tgggaagagt tgacttatga ttataggttt     2940
gtttcgagtg atcagcgact tccttgttat tgtggattcc caaaatgccg tggagttgtt     3000
```

```
aacgatgttg aagcagaggg gcaatcagcc aaaataaggg tcaatagaag tgaattattt    3060
caacaatga                                                            3069
```

<210> SEQ ID NO 8
<211> LENGTH: 1022
<212> TYPE: PRT
<213> ORGANISM: Artificial Sequence
<220> FEATURE:
<223> OTHER INFORMATION: OSTRX1 protein

<400> SEQUENCE: 8

```
Met Val Ile Ala Val Glu Gly Gly Phe Val His Glu Glu Glu Val
1               5                   10                  15

Asp His Pro Ile Arg Tyr Leu Pro Leu Gly Arg Val Tyr Ser Ser
                20                  25                  30

Ala Pro Cys Pro Leu Pro Lys Lys Pro Arg Ser Ala Glu Asp Gly Lys
            35                  40                  45

Pro Pro Val Ile Val Tyr Tyr Arg Arg Arg Lys Lys Pro Arg Val
        50                  55                  60

Glu Gly Pro Pro Pro Ser Pro Ala Thr Ala Pro Pro Met Leu His Pro
65                  70                  75                  80

Arg Glu Asp Asp Glu Asp Glu Glu Val Thr Arg Arg Lys Gly Ser Leu
                85                  90                  95

Lys Tyr Glu Leu Leu Ser Leu Gly Gln Ala Pro Pro Ala Leu Gly Gly
            100                 105                 110

Asp Gly Glu Glu Pro Ala Arg Arg Cys Leu Arg Arg Ser Gly Gly
        115                 120                 125

Ala Glu Arg Arg Gly Tyr Phe Ser Glu Pro Lys Arg Arg Gln Arg Gln
    130                 135                 140

Gly Val His Lys Glu Ala Ala Ser Ser Ala Gly Arg Arg Trp Leu Glu
145                 150                 155                 160

Leu Glu Ile Glu Ala Ala Asp Pro Leu Ala Phe Val Gly Leu Gly Cys
                165                 170                 175

Lys Val Phe Trp Pro Leu Asp Glu Asp Trp Tyr Lys Gly Ser Ile Thr
            180                 185                 190

Gly Tyr Asn Glu Ala Thr Lys Lys His Ser Val Lys Tyr Asp Asp Gly
        195                 200                 205

Glu Ser Glu Asp Leu Asn Leu Ala Asp Glu Arg Ile Lys Phe Ser Ile
    210                 215                 220

Ser Ser Glu Glu Met Lys Cys Arg Asn Leu Lys Phe Gly Ile Ser Asn
225                 230                 235                 240

Leu Asn Lys Arg Gly Tyr Asp Glu Leu Leu Ala Leu Ala Val Ser Leu
                245                 250                 255

His Asp Tyr Gln Gly Leu Asp Pro Gly Asp Leu Val Trp Ala Lys Leu
            260                 265                 270

Thr Gly His Ala Met Trp Pro Ala Val Val Asp Glu Ser Asn Val
        275                 280                 285

Pro Ala Asn Arg Ala Leu Lys Pro Gly Arg Leu Asp Gln Ser Ile Leu
    290                 295                 300

Val Gln Phe Phe Gly Thr His Asp Phe Ala Arg Ile Lys Leu Lys Gln
305                 310                 315                 320

Ala Val Pro Phe Leu Asn Gly Leu Leu Ser Ser Leu His Leu Lys Cys
                325                 330                 335

Lys Gln Ala Arg Phe Tyr Arg Ser Leu Glu Glu Ala Lys Glu Phe Leu
            340                 345                 350
```

```
Cys Thr Gln Leu Leu Pro Glu Asn Met Leu Gln Leu Gln Lys Ser Met
        355                 360                 365

Glu Lys Gly Ser Ser Asp Ala Asn Ser Asn Lys Asp Val His Ser Cys
        370                 375                 380

Asp Asn Leu Ser Glu Asp Lys Thr Ala Glu Ser Gly Gly Asp Tyr Asp
385                 390                 395                 400

Glu Met Thr Pro Ile Glu Leu Gly Asn Leu Arg Val Ser Lys Leu Gly
                405                 410                 415

Arg Ile Val Thr Asp Ser Asp Tyr Phe His Asn Lys Lys His Ile Trp
            420                 425                 430

Pro Glu Gly Tyr Thr Ala Phe Arg Lys Phe Arg Ser Val Lys Asp Pro
        435                 440                 445

His Val Val Ile Leu Tyr Lys Met Glu Val Leu Arg Asn Ser Asp Ile
        450                 455                 460

Lys Ala Arg Pro Leu Phe Arg Val Thr Ser Glu Asp Gly Thr Gln Ile
465                 470                 475                 480

Asp Gly Ser Thr Pro Asn Thr Cys Trp Lys Glu Ile Tyr Cys Arg Leu
                485                 490                 495

Lys Glu Lys Gln Arg Asn Val Ala Ser Gly Leu Asp Arg Asp Val Cys
            500                 505                 510

Gln Gly Ser Gly Ser Tyr Met Phe Gly Phe Ser Asn Pro Gln Ile Arg
        515                 520                 525

Gln Leu Ile Gln Glu Leu Pro Asn Ala Arg Ser Cys Leu Lys Tyr Phe
        530                 535                 540

Glu Asn Ala Gly Asp Thr Phe Arg Gly Tyr Arg Ala Val His Val Asn
545                 550                 555                 560

Trp Lys Asp Leu Asp Tyr Cys Ser Val Cys Asp Met Asp Glu Glu Tyr
                565                 570                 575

Glu Asp Asn Leu Phe Leu Gln Cys Asp Lys Cys Arg Met Met Val His
            580                 585                 590

Ala Arg Cys Tyr Gly Glu Leu Glu Pro Leu Asn Gly Val Leu Trp Leu
        595                 600                 605

Cys Asn Leu Cys Arg Pro Glu Ala Pro Arg Val Ser Pro Arg Cys Cys
        610                 615                 620

Leu Cys Pro Val Thr Gly Gly Ala Met Lys Pro Thr Thr Asp Gly Arg
625                 630                 635                 640

Trp Ala His Leu Ala Cys Ala Ile Trp Ile Pro Glu Thr Cys Leu Lys
                645                 650                 655

Asp Val Lys Arg Met Glu Pro Ile Asp Gly Leu Ser Arg Ile Asn Lys
            660                 665                 670

Asp Arg Trp Lys Leu Leu Cys Ser Ile Cys Gly Val Ala Tyr Gly Ala
        675                 680                 685

Cys Ile Gln Cys Ser His Pro Thr Cys Arg Val Ala Tyr His Pro Leu
        690                 695                 700

Cys Ala Arg Ala Ala Asp Leu Cys Val Glu Leu Asp Asp Asp Lys
705                 710                 715                 720

Ile His Leu Met Leu Leu Asp Glu Asp Glu Pro Cys Ile Arg Leu
                725                 730                 735

Leu Ser Tyr Cys Lys Lys His Arg Gln Pro Ser Thr Glu Arg Pro Ser
            740                 745                 750

Leu Glu Ser Asn Leu Ala Lys Pro Ala Val Val Gln Thr Asp Ala
        755                 760                 765
```

```
Val Pro Pro Ser Gly Cys Ala Arg Thr Glu Pro Tyr Asn Ile His Gly
    770                 775                 780

Arg Arg Gly Gln Lys Gln Pro Gln Val Met Ala Thr Ala Ser Val Lys
785                 790                 795                 800

Arg Leu Tyr Val Glu Asn Met Pro Tyr Ile Val Ser Gly Phe Cys Gln
            805                 810                 815

Asn Arg Val Gly His Asp Ala Ile Ser Glu Pro Ile Gln Ser Val Gly
            820                 825                 830

Phe Leu Asp Val Ala His Gln Glu Ala Val Gly Asn Val Ser Ser Met
        835                 840                 845

Ile Glu Lys Tyr Lys Ser Met Lys Ala Thr Phe Arg Arg Arg Leu Ala
850                 855                 860

Phe Gly Lys Ser Arg Ile His Gly Phe Gly Val Phe Ala Lys Val Ser
865                 870                 875                 880

His Lys Ala Gly Asp Met Met Ile Glu Tyr Ile Gly Glu Leu Val Arg
            885                 890                 895

Pro Pro Ile Ser Asp Ile Arg Glu Arg Ile Tyr Asn Ser Leu Val
            900                 905                 910

Gly Ala Gly Thr Tyr Met Phe Arg Ile Asp Asp Glu Arg Val Ile Asp
        915                 920                 925

Ala Thr Arg Ala Gly Ser Ile Ala His Leu Ile Asn His Ser Cys Glu
930                 935                 940

Pro Asn Cys Tyr Ser Arg Val Ile Ser Val Leu Gly Asp Glu His Ile
945                 950                 955                 960

Ile Ile Phe Ala Lys Arg Asp Ile Asn Pro Trp Glu Glu Leu Thr Tyr
            965                 970                 975

Asp Tyr Arg Phe Val Ser Ser Asp Gln Arg Leu Pro Cys Tyr Cys Gly
            980                 985                 990

Phe Pro Lys Cys Arg Gly Val Val  Asn Asp Val Glu Ala  Glu Gly Gln
        995                 1000                1005

Ser Ala  Lys Ile Arg Val Asn  Arg Ser Glu Leu Phe  Gln Gln
    1010                1015                1020
```

<210> SEQ ID NO 9
<211> LENGTH: 2253
<212> TYPE: DNA
<213> ORGANISM: Artificial Sequence
<220> FEATURE:
<223> OTHER INFORMATION: cDNA sequence of OsVIN2

<400> SEQUENCE: 9

| | | |
|---|---|---|
| atggatccac cctacgcagg agtacctatt gatcctgcta atgccgatt gatgagtgtg | 60 |
| gatgaaaagc gggaacttgt ccgtgaatta tcgaagcggc cagaaagtgc tcctgacaaa | 120 |
| ctgcagtctt ggagtcgccg tgaaattgta gagattcttt gtgctgattt aggaagggaa | 180 |
| aggaagtaca ctggattatc gaagcagaga atgttggaat atctcttcag agttgtgact | 240 |
| ggcaaatcat ctggtggtgg cgttgtggag catgtgcaag agaaggagcc taccctgaa | 300 |
| cccaacacag ccaaccatca gtcccctgcg aaacggcagc gaaagagtga caacccatca | 360 |
| cgactaccaa ttgttgcaag cagtccaact acagaaatac ccaggccagc aagtaatgct | 420 |
| cgcttctgcc acaatttagc ttgcagagcg actcttaatc agaagataa attttgcaga | 480 |
| cgctgttcat gctgtatttg tttcaagtac gatgacaata aggatcctag cctctggtta | 540 |
| ttctgtagtt cagatcaacc cttgcagaaa gattcttgtg tattttcgtg ccatcttgaa | 600 |
| tgtgctctta aggatggaag aactggcatc atgcagagtg ggcagtgcaa gaaacttgat | 660 |

```
ggtggttatt actgcactcg ctgtcggaaa cagaatgatc tgcttgggtc ctggaagaaa        720
caactggtga tagctaaaga tgctcgccgg ttgatgtat  tgtgtcatcg gatttttttg        780
agtcataaga ttcttgtctc cacggagaag tacttggttt tgcatgaaat tgttgacaca        840
gcgatgaaga aactggaggc tgaggttggt cctatatctg gagttgcaaa tatgggtcgt        900
ggaattgtga gccggcttgc tgttggtgct gaagttcaga actttgtgc  tcgagcaata        960 gaaaccatgg agtctctgtt ttgtggatct ccttctaact tgcaatttca acgttcacgg       1020
atgataccat caaacttcgt aaagtttgaa gctataaccc aaacatctgt cactgtagtt       1080
ttggatttgg gtcctatact tgctcaagat gtaacatgct ttaatgtatg cacagagtg        1140 gcagccacag gctcgttctc atcaagtcca actggcatca tacttgcacc attaaaaacg       1200
ttagtggtca ctcaacttgt gccagctaca agctatatat tcaaggtagt tgccttcagt       1260
aactacaagg agtttggatc gtgggaagcc aaaatgaaga caagctgtca gaggaagtt        1320 gatctgaagg gtttgatgcc agtgggtct  gggctagacc aaaacaatgg agcccaaag        1380 gcaaacagtg gtggtcagtc tgatccttct tcagaaggtg tggactcaaa taataacact       1440
gcggtgtatg ctgatctcaa taaatcacca gaaagtgatt ttgaatattg tgaaaatcct       1500
gagatacttg attcagacaa agcaagtcat caccccaatg aacctacaaa caactcacag       1560
agtatgccga tggtcgtagc tagggttacg gaggtatctg gattggagga agctcctgga       1620
ctctcagcat cagctttgga cgaggagccc aattcagcag ttcaaacaca attacttaga       1680
gaatcctcaa attcaatgga gcagaaccag agaagcgaag ttcctggatc acaggatgca       1740
tcaaatgctc ctgctggaaa tgaggtggtg attgttccac ctcgatattc tggctctatt       1800
ccaccaactg cacctagata tatggaaaat ggtaaggata tcagtgggag gagcttgaaa       1860
gcaaaacctg gtgataacat ccttcaaaat ggctcttcca agcctgaaag ggaaccaggg       1920
aattcttcaa ataaaagaac atcaggtaaa tgtgaggaaa tcggccacaa ggatggatgc       1980
ccagaagcat cttatgagta ctgtgttaag gtggtcaggt ggctggaatg tgagggttac       2040
attgagacca acttcagagt gaagtttctg acttggtata gccttcgtgc taccctcat        2100 gacaggaaga tagtcagcgt ctacgtaaac actcttattg atgatcctgt tagcctttct       2160
ggccagcttg ctgacacttt ctctgaggcc atctacagca aaaggccacc ttctgttcgc       2220
tccggtttct gcatggaact ttggcattaa taa                                    2253
```

<210> SEQ ID NO 10
<211> LENGTH: 749
<212> TYPE: PRT
<213> ORGANISM: Artificial Sequence
<220> FEATURE:
<223> OTHER INFORMATION: OsVIN2 protein

<400> SEQUENCE: 10

```
Met Asp Pro Pro Tyr Ala Gly Val Pro Ile Asp Pro Ala Lys Cys Arg
1               5                   10                  15

Leu Met Ser Val Asp Glu Lys Arg Glu Leu Val Arg Glu Leu Ser Lys
                20                  25                  30

Arg Pro Glu Ser Ala Pro Asp Lys Leu Gln Ser Trp Ser Arg Arg Glu
            35                  40                  45

Ile Val Glu Ile Leu Cys Ala Asp Leu Gly Arg Glu Arg Lys Tyr Thr
        50                  55                  60

Gly Leu Ser Lys Gln Arg Met Leu Glu Tyr Leu Phe Arg Val Val Thr
65                  70                  75                  80
```

```
Gly Lys Ser Ser Gly Gly Val Val Glu His Val Gln Glu Lys Glu
            85                  90                  95

Pro Thr Pro Glu Pro Asn Thr Ala Asn His Gln Ser Pro Ala Lys Arg
            100                 105                 110

Gln Arg Lys Ser Asp Asn Pro Ser Arg Leu Pro Ile Val Ala Ser Ser
            115                 120                 125

Pro Thr Thr Glu Ile Pro Arg Pro Ala Ser Asn Ala Arg Phe Cys His
            130                 135                 140

Asn Leu Ala Cys Arg Ala Thr Leu Asn Pro Glu Asp Lys Phe Cys Arg
145                 150                 155                 160

Arg Cys Ser Cys Ile Cys Phe Lys Tyr Asp Asp Asn Lys Asp Pro
                165                 170                 175

Ser Leu Trp Leu Phe Cys Ser Ser Asp Gln Pro Leu Gln Lys Asp Ser
            180                 185                 190

Cys Val Phe Ser Cys His Leu Glu Cys Ala Leu Lys Asp Gly Arg Thr
            195                 200                 205

Gly Ile Met Gln Ser Gly Gln Cys Lys Lys Leu Asp Gly Gly Tyr Tyr
            210                 215                 220

Cys Thr Arg Cys Arg Lys Gln Asn Asp Leu Leu Gly Ser Trp Lys Lys
225                 230                 235                 240

Gln Leu Val Ile Ala Lys Asp Ala Arg Arg Leu Asp Val Leu Cys His
                245                 250                 255

Arg Ile Phe Leu Ser His Lys Ile Leu Val Ser Thr Glu Lys Tyr Leu
                260                 265                 270

Val Leu His Glu Ile Val Asp Thr Ala Met Lys Lys Leu Glu Ala Glu
            275                 280                 285

Val Gly Pro Ile Ser Gly Val Ala Asn Met Gly Arg Gly Ile Val Ser
            290                 295                 300

Arg Leu Ala Val Gly Ala Glu Val Gln Lys Leu Cys Ala Arg Ala Ile
305                 310                 315                 320

Glu Thr Met Glu Ser Leu Phe Cys Gly Ser Pro Ser Asn Leu Gln Phe
                325                 330                 335

Gln Arg Ser Arg Met Ile Pro Ser Asn Phe Val Lys Phe Glu Ala Ile
            340                 345                 350

Thr Gln Thr Ser Val Thr Val Val Leu Asp Leu Gly Pro Ile Leu Ala
            355                 360                 365

Gln Asp Val Thr Cys Phe Asn Val Trp His Arg Val Ala Ala Thr Gly
            370                 375                 380

Ser Phe Ser Ser Ser Pro Thr Gly Ile Ile Leu Ala Pro Leu Lys Thr
385                 390                 395                 400

Leu Val Val Thr Gln Leu Val Pro Ala Thr Ser Tyr Ile Phe Lys Val
                405                 410                 415

Val Ala Phe Ser Asn Tyr Lys Glu Phe Gly Ser Trp Glu Ala Lys Met
                420                 425                 430

Lys Thr Ser Cys Gln Lys Glu Val Asp Leu Lys Gly Leu Met Pro Gly
            435                 440                 445

Gly Ser Gly Leu Asp Gln Asn Asn Gly Ser Pro Lys Ala Asn Ser Gly
            450                 455                 460

Gly Gln Ser Asp Pro Ser Ser Glu Gly Val Asp Ser Asn Asn Thr
465                 470                 475                 480

Ala Val Tyr Ala Asp Leu Asn Lys Ser Pro Glu Ser Asp Phe Glu Tyr
                485                 490                 495
```

Cys Glu Asn Pro Glu Ile Leu Asp Ser Asp Lys Ala Ser His His Pro
            500                 505                 510

Asn Glu Pro Thr Asn Asn Ser Gln Ser Met Pro Met Val Val Ala Arg
        515                 520                 525

Val Thr Glu Val Ser Gly Leu Glu Glu Ala Pro Gly Leu Ser Ala Ser
    530                 535                 540

Ala Leu Asp Glu Glu Pro Asn Ser Ala Val Gln Thr Gln Leu Leu Arg
545                 550                 555                 560

Glu Ser Ser Asn Ser Met Glu Gln Asn Gln Arg Ser Glu Val Pro Gly
                565                 570                 575

Ser Gln Asp Ala Ser Asn Ala Pro Ala Gly Asn Glu Val Val Ile Val
            580                 585                 590

Pro Pro Arg Tyr Ser Gly Ser Ile Pro Pro Thr Ala Pro Arg Tyr Met
        595                 600                 605

Glu Asn Gly Lys Asp Ile Ser Gly Arg Ser Leu Lys Ala Lys Pro Gly
    610                 615                 620

Asp Asn Ile Leu Gln Asn Gly Ser Ser Lys Pro Glu Arg Glu Pro Gly
625                 630                 635                 640

Asn Ser Ser Asn Lys Arg Thr Ser Gly Lys Cys Glu Glu Ile Gly His
                645                 650                 655

Lys Asp Gly Cys Pro Glu Ala Ser Tyr Glu Tyr Cys Val Lys Val Val
            660                 665                 670

Arg Trp Leu Glu Cys Glu Gly Tyr Ile Glu Thr Asn Phe Arg Val Lys
        675                 680                 685

Phe Leu Thr Trp Tyr Ser Leu Arg Ala Thr Pro His Asp Arg Lys Ile
    690                 695                 700

Val Ser Val Tyr Val Asn Thr Leu Ile Asp Asp Pro Val Ser Leu Ser
705                 710                 715                 720

Gly Gln Leu Ala Asp Thr Phe Ser Glu Ala Ile Tyr Ser Lys Arg Pro
                725                 730                 735

Pro Ser Val Arg Ser Gly Phe Cys Met Glu Leu Trp His
            740                 745

<210> SEQ ID NO 11
<211> LENGTH: 999
<212> TYPE: DNA
<213> ORGANISM: Artificial Sequence
<220> FEATURE:
<223> OTHER INFORMATION: cDNA sequence of OsCOL4

<400> SEQUENCE: 11
atggaggcgg tggaggacaa ggcgatggtg ggagtgggag gagcggtggc ggcggggtac      60
tcctcgtcgt cgtgggggtt ggggacgcgg gcgtgcgact cgtgcggcgg ggaggcggcg     120
cggctctact gccgcgcaga cggggcgttc ctgtgcgccc ggtgcgacgc gcgggcgcac     180
ggcgccgggt cgcgccacgc gcgggtgtgg ctgtgcgagg tgtgcgagca cgcgcccgcc     240
gccgtcacgt gccgggcgga cgccgcggcg ctgtgcgccg cctgcgacgc cgacatccac     300
tcggcgaacc cgctcgcgcg caggcacgag cgcctccccg tcgcgccctt cttcggcccg     360
ctcgccgacg cgccgcagcc cttcaccttc tcccaggccg ccgcggatgc cgccggggcg     420
cgggaggagg atgcggacga tgaccggagc aacgaggccg aggcggcgtc gtggcttctc     480
cccgagcccg acgacaatag ccacgaggat agcgccgcag ccgccgacgc gttcttcgcc     540
gacaccggcg cgtacctcgg cgtcgacctg gacttcgccc ggtccatgga cggaatcaag     600
gccatcgggg taccggtcgc gccgcccgag ctggacctca ccgccggcag ccttttctac     660

-continued

```
cccgaacact ccatgggcca cagcttgtcg tcgtcggagg tcgcgatcgt accggacgcg    720
ctgtcggcgg gcgcggcggc gccgcccatg gtggtggtgg tggcgagcaa ggggaaggag    780
agggaggcgc ggctgatgcg gtacagggag aagcgcaaga accggcggtt cgacaagacc    840
atccggtacg cgtcccgcaa ggcgtacgcc gagacgcggc cgcgcatcaa gggccggttc    900
gccaagcgca ccgccgacgc cgacgacgac gacgaggcgc catgctcgcc ggcgttctcc    960
gccctcgccg cgtcggacgg cgtcgtgccg tcgttctga                           999
```

<210> SEQ ID NO 12
<211> LENGTH: 332
<212> TYPE: PRT
<213> ORGANISM: Artificial Sequence
<220> FEATURE:
<223> OTHER INFORMATION: OsCOL4 protein
<400> SEQUENCE: 12

```
Met Glu Ala Val Glu Asp Lys Ala Met Val Gly Val Gly Ala Val
 1               5                  10                  15

Ala Ala Gly Tyr Ser Ser Ser Trp Gly Leu Gly Thr Arg Ala Cys
                20                  25                  30

Asp Ser Cys Gly Gly Glu Ala Ala Arg Leu Tyr Cys Arg Ala Asp Gly
            35                  40                  45

Ala Phe Leu Cys Ala Arg Cys Asp Ala Arg Ala His Gly Ala Gly Ser
    50                  55                  60

Arg His Ala Arg Val Trp Leu Cys Glu Val Cys Glu His Ala Pro Ala
65                  70                  75                  80

Ala Val Thr Cys Arg Ala Asp Ala Ala Leu Cys Ala Ala Cys Asp
                85                  90                  95

Ala Asp Ile His Ser Ala Asn Pro Leu Ala Arg His Glu Arg Leu
            100                 105                 110

Pro Val Ala Pro Phe Gly Pro Leu Ala Asp Ala Pro Gln Pro Phe
        115                 120                 125

Thr Phe Ser Gln Ala Ala Asp Ala Ala Gly Ala Arg Glu Glu Asp
    130                 135                 140

Ala Asp Asp Asp Arg Ser Asn Glu Ala Glu Ala Ala Ser Trp Leu Leu
145                 150                 155                 160

Pro Glu Pro Asp Asp Asn Ser His Glu Asp Ser Ala Ala Ala Ala Asp
                165                 170                 175

Ala Phe Phe Ala Asp Thr Gly Ala Tyr Leu Gly Val Asp Leu Asp Phe
            180                 185                 190

Ala Arg Ser Met Asp Gly Ile Lys Ala Ile Gly Val Pro Val Ala Pro
        195                 200                 205

Pro Glu Leu Asp Leu Thr Ala Gly Ser Leu Phe Tyr Pro Glu His Ser
    210                 215                 220

Met Ala His Ser Leu Ser Ser Ser Glu Val Ala Ile Val Pro Asp Ala
225                 230                 235                 240

Leu Ser Ala Gly Ala Ala Ala Pro Pro Met Val Val Val Ala Ser
                245                 250                 255

Lys Gly Lys Glu Arg Glu Ala Arg Leu Met Arg Tyr Arg Glu Lys Arg
            260                 265                 270

Lys Asn Arg Arg Phe Asp Lys Thr Ile Arg Tyr Ala Ser Arg Lys Ala
        275                 280                 285

Tyr Ala Glu Thr Arg Pro Arg Ile Lys Gly Arg Phe Ala Lys Arg Thr
    290                 295                 300
```

Ala Asp Ala Asp Asp Asp Glu Ala Pro Cys Ser Pro Ala Phe Ser
305                 310                 315                 320

Ala Leu Ala Ala Ser Asp Gly Val Val Pro Ser Phe
                325                 330

<210> SEQ ID NO 13
<211> LENGTH: 894
<212> TYPE: DNA
<213> ORGANISM: Artificial Sequence
<220> FEATURE:
<223> OTHER INFORMATION: cDNA sequence of OsCOL8

<400> SEQUENCE: 13

```
atgtcggcgg cgtcgggcgc cgcgtgcggg gtgtgtgggg gaggggtggg ggagtgcggg      60
tgcctgctgc atcagcggcg tgggggaggc ggtggtggtg gaggtggagg ggtgaggtgc     120
gggatcgcgg cggacctgaa ccggggggttt ccggcgatct ttcagggggt ggggggtggag    180
gagacggcgg tggaagggga tggaggagcc cagccggcgg ccgggctgca ggagttccag     240
ttcttcggcc acgacgacca cgacagcgtc gcgtggctct tcaacgaccc ggcgccgccc     300
ggcgggacgg accaccagct tcaccgccaa accgcgccca tggcggtcgg caacggcgcg     360
gcggcggcgc agcagcggca ggcgttcgac gcgtacgcgc agtaccagcc ggggcacggg     420
ctcacgttcg acgtgccgct cacccgagge gaggccgccg ccgcggtgct cgaggccagc     480
ctcggcctcg gcggcgccgg cgccggcggc aggaacccgg cgacgtcgag cagcacaatc     540
atgtccttct gtgggagcac gttcactgac gccgtgagct ccatcccgaa agatcacgcg     600
gcggcggcg cggtcgttgc caacggcggc ctgagcggcg gcggcggcga cccggcgatg     660
gaccgggagg cgaaggtgat gcggtacaag gagaagagga agcggaggcg atacgagaag     720
cagatccggt acgcctcgcg caaggcctac gccgagatgc ggccgcgcgt gaagggccgc     780
ttcgccaagg tgcccgacgg cgagctggac ggcgcgacac cgccgccgcc gtcctccgcc     840
gccggcggcg gctacgagcc cggccggctc gacctcggat ggttccgttc gtag           894
```

<210> SEQ ID NO 14
<211> LENGTH: 297
<212> TYPE: PRT
<213> ORGANISM: Artificial Sequence
<220> FEATURE:
<223> OTHER INFORMATION: OsCOL8 protein

<400> SEQUENCE: 14

Met Ser Ala Ala Ser Gly Ala Cys Gly Val Cys Gly Gly Gly Val
1               5                   10                  15

Gly Glu Cys Gly Cys Leu Leu His Gln Arg Arg Gly Gly Gly Gly
                20                  25                  30

Gly Gly Gly Gly Gly Val Arg Cys Gly Ile Ala Ala Asp Leu Asn Arg
            35                  40                  45

Gly Phe Pro Ala Ile Phe Gln Gly Val Gly Val Glu Glu Thr Ala Val
        50                  55                  60

Glu Gly Asp Gly Gly Ala Gln Pro Ala Ala Gly Leu Gln Glu Phe Gln
65                  70                  75                  80

Phe Phe Gly His Asp Asp His Asp Ser Val Ala Trp Leu Phe Asn Asp
                85                  90                  95

Pro Ala Pro Pro Gly Gly Thr Asp His Gln Leu His Arg Gln Thr Ala
            100                 105                 110

Pro Met Ala Val Gly Asn Gly Ala Ala Ala Ala Gln Gln Arg Gln Ala

|  | 115 |  | 120 |  | 125 |  |  |  |
| --- | --- | --- | --- | --- | --- | --- | --- | --- |

Phe Asp Ala Tyr Ala Gln Tyr Gln Pro Gly His Gly Leu Thr Phe Asp
    130                    135                  140

Val Pro Leu Thr Arg Gly Glu Ala Ala Ala Val Leu Glu Ala Ser
145                    150                  155                  160

Leu Gly Leu Gly Gly Ala Gly Ala Gly Arg Asn Pro Ala Thr Ser
                165                  170                  175

Ser Ser Thr Ile Met Ser Phe Cys Gly Ser Thr Phe Thr Asp Ala Val
            180                  185                  190

Ser Ser Ile Pro Lys Asp His Ala Ala Ala Ala Val Val Ala Asn
        195                  200                  205

Gly Gly Leu Ser Gly Gly Gly Asp Pro Ala Met Asp Arg Glu Ala
        210                  215                  220

Lys Val Met Arg Tyr Lys Glu Lys Arg Lys Arg Arg Tyr Glu Lys
225                    230                  235                  240

Gln Ile Arg Tyr Ala Ser Arg Lys Ala Tyr Ala Glu Met Arg Pro Arg
            245                  250                  255

Val Lys Gly Arg Phe Ala Lys Val Pro Asp Gly Glu Leu Asp Gly Ala
            260                  265                  270

Thr Pro Pro Pro Ser Ser Ala Ala Gly Gly Gly Tyr Glu Pro Gly
        275                  280                  285

Arg Leu Asp Leu Gly Trp Phe Arg Ser
        290                  295

<210> SEQ ID NO 15
<211> LENGTH: 13000
<212> TYPE: DNA
<213> ORGANISM: Artificial Sequence
<220> FEATURE:
<223> OTHER INFORMATION: genomic DNA sequence of OsMADS14

<400> SEQUENCE: 15

```
gcttcagtta ataagatata tacttggtat tttgcttaca ttttcatttt ttttccccct     60
gtcacagcaa attccccaag cataacatgt gagtgtgaca acacagttcc tgttctctta    120
gcttatcttg gattcaatcc cctcatccaa aattaaattc catttgttcc ctatttcaga    180
ggggaatttc tcggggtatc tctagtattt agcaacactt taatgtgtcc tatatattcc    240
cttggttcat cccctatagt catttcccat gattctctgt tcccttgggt ccactatgta    300
caggtattgc acatataaat catgaaacta ccaaatgcat tggcaattgc aagttgatgt    360
acaactatag aagtgtgttt atttggggat gaagtgggat atgttaggtc catccttatt    420
ttctgagatg ggatagcccc atctatgtct ttggcataag ggatataatg ctcttatttt    480
ttttataagg aatgtgaggg tgtggcccgc atctcaattc gagtccgtta atttttttca    540
tataaagttg acctggatct agaaaaatat tccatttcaa ggattattct gtcccacctg    600
ttatcgaacc gaacaccctg aaaatagatt tgtccccaca tgactatctc atccctttca    660
accaaataca ttataactta ttgacggttc tgcagctctg gctcgtttcg gaaaagagct    720
atgatggagg ctcgggctca gctaatttgg cttacaagct gagctgagct ttttgtcctc    780
acctagttct gcccatgggg aatctaacat tatcaatcat acaccatatc ttaaagagat    840
gctgctatga tacgtcaaga agtcaagttt taaggtagaa tatatggtag ttgggaaaat    900
agaatcatta cataaatgtt agaaatatagg gatgccaacg cgacatgctt gcaggctttg    960
aggcccagta aacctaattg tacttttttt tcatccattt ttattatata cttgttgatg   1020
```

```
aaaattaact tagaatatgg gctcttatgt aagatagcat cgcctgcatc cttacaaaga    1080
gacagataga tccaatcgta caattaaatc agtaatttta taagagaatg aaataacatt    1140
ctagctagtg tatccaagaa tgcacagtga agtccgtatt taagtcccat ccaaaacgat    1200
gtgatgttag atctgatcca aaatatttaa taatgtagct caagttttgc atagcccctg    1260
agaaccagac aagccaatgt taaaattcct actgtgcata gggagggcaa tcaatcatcc    1320
tactgcatga gtaggtccct gcttcctgtt caaaatactt tctccgttct acgaagacta    1380
cattttagga acaaagctaa caaactaatg gtgagagaag aaaaatcaaa tgaacactca    1440
ttaatacgaa aataaattat cgtcaaatga taacctagga ataattttga gttacagatt    1500
aattataggt aagaaagaac aaagttaaag cgatcgaaaa tgaagtctat ttaaggacca    1560
gtttagtatg gctctagcta tagctccact cattctatag ctggagtcca accaaatagt    1620
ttctacacct aaaatagaaa tatagttggc tagagcgtta tcacaaaata aactagagag    1680
gtggagttga gttcagaccg ctacacaact tcactttaaa ctttaactcc taaagttaaa    1740
ttttaagaga tgaagatcta ctaaacaggc tttaatacgg aggaaatgca ttcatccaca    1800
aaggtcaaaa gcagcagaaa gagaacgaat gcctttgctg cattcaaccc caagcagagc    1860
tgcaggggtg ccaactgcca atcaggcaat catccactct gggagcgaca ggcgacgcca    1920
ttgatgggca cacccctcg ccggggccga cgggagacga gacgacgcag gcactgtttt     1980
gcggccgacc aagccaagc caagccagga gccatcccgt cccatcacga cgcattgctg     2040
ccgcggccta attgggcagg aaaagccatg gcccaccccc accgcctggc cagacgagac    2100
ggcccaaaaa aggatcggcc cagaaaagcc cacgagagta cgacgcacgc acgcgtcgcc    2160
gggaggcggg gcccgggccg gcgccgcctc gcccaatggc cgttcgacag cggaggcgat    2220
cgaaaccacc ccgtatcgc caaaccgcct cctcctcctc cgacgatccg gcgcgcgctc     2280
cctttaaaat cccccatttt cctcctcctc ctcctcctcg tcgtcgtcgt ctcccccact    2340
cgatcgatcc atccatcgat cgatcggtcc ccccatcgc gcgcgacgca ttccgccgcc     2400
gtctcgccgt gtccacgtga tgggggccgg ggctagggga taggcggata gccagcagcc    2460
accaccacca gtagttgccg tgtggggata ggtgtggcta tagggctagt ggtcgtcgct    2520
gatagcgagg tgggtagggt taattttggt tggaggtaga gagagagaga gagggaggga    2580
gggaggagga ggaggaggag gaggaggagg aagaacagga ggaagatggg gcggggcaag    2640
gtgcagctga agcggatcga gaacaagatc aaccggcagg tgaccttctc caagcgcagg    2700
tcggggctgc tcaagaaggc gaatgagatc tccgtgctct gcgacgccga ggtcgcgctc    2760
atcatcttct ccaccaaggg caagctctac gagtacgcca ccgactcatg gtacgtacgt    2820
acgtacgtgt gcttgattaa atttcatcct catcgcttgt ctctaagctt tcagttcttt    2880
tcgcttaatc gagcaatcct tgcgctacat gatgtgttcc cgtttccgtt ctgttcgtat    2940
cgatcgattg cctttgaatt ctgtgtgtga ttaattcgat ctgtcctgat tgctcgaatt    3000
aattttgttg cgtgtgtttc ggggttatcc ccaataatct gtttgaattt ctgctgcgat    3060
tgttgattgc ttgccggcga tggaggaggc agcgtgtttt gctatttcag gctttgagct    3120
gacggcgtga ggtgagatgc gttgcatctg tgcactgtag ctacagtgcc cgtacgaggg    3180
taattttatg ctccgctttc gctggagagg gcgttgctgc tgcgctattt ggggaatttt    3240
tttttggccc tgccgatggg tgctgcttgc ttggcgacaa gctagctttg cacccaaagg    3300 ggagagggggt gattagctag gaactctagt acgtagattt gatggacctg ggattatttg    3360
gggattaaaa tggtcttggc ttgtgttcat ctaaaattct actgaacttg ctgcttgtgt    3420
```

```
tgtgtgtgcc tcttctttct tcactattcc ccatattaat tctgggctcg tttagatctt    3480
ctttctctct ccctggccat ctctttctct tgaggcaact aagcatatta agggagaaga    3540
tgaaacggga tgcatcggga gatggaggag ttcatatctt aagctgctgg tgacttgttg    3600
gaacccttt cgctggttcg tctgcctcta gctttcttgg actctttgct gatgcatgcc     3660
atgcttttca gaacgaaaag attttactag aacaaactta aagctaggg ctggcctta     3720
atctttactt cttaattccc ggctgtcatt agttcaatct aatggttcat tagttgctgg    3780
gttctacctt tcctataagg ttcttttga gatgtacatg gtttctgaag aaacatccat    3840
gcttctagct agcctgatta cagactggtt tcatgctgct tcttttttat cgaaaagtca    3900
ccttggggga gagtttccca cttaactcat tcgattttct tagttcagag gggaggtaca    3960
aaggttacaa cattacatcg gaggtctgtt aagatgttaa gacttagtaa gaggtagaga    4020
ggagttaaca ggaaaaaaaa gaacttataa gctaaaggtt catcctagtt agcgctttag    4080
ttgctgggtt ctacctttc tgtcaggttc ttcttgggat gtgcatatgg ttcctgaaga     4140
aacagacatt agaaatttag aactaagaag caaaacgttg gatgcttcca gtataccata    4200
tcatctgaag gatatttatc cttcttgatg ttttcgacaa tgatttacta ttaatgcatt    4260
gttatgcaag ctttgttaag tcaacatgca aatcttagag tttgatggtt aattccagtt    4320
cttatatatt ttttaagtta aaaattttct tatctctcct ttttcctcac tacatacgaa    4380
tagagtttga tctggctgtt ataaattttc ttcagttttg tgggcatcct tatatctact    4440
aatcagactc cccatatgat cagtgattat cagcttatac tctattctaa ttctatgaat    4500
gaacgactaa ttaacttaat taactcctcg ctgatttaat ccaataaggg tagtgtgttg    4560
ggcatcccca taatgctagc aaccacatct ctagataaga gtcattagta tcacatattt    4620
tgaaatcctt ctcactctaa ccattgatca gtgagttaag acataggagt agagcttcac    4680
gtgaggtaac agtgtttgga tttcaaggta tcaagtttgg ggtgggagta cacgagccga    4740
tggattaatc tgatttttt ttcgtttctc gtacgtcatt aaacgtctta tttggaaatc     4800
aactccatta ggttcctgca gggtactgta gttatgctaa ttaatccttc ttaagacttt    4860
tccaagattt agctttaaac agatgctttc atgaacctag ttgggaaaca tgacaaatcc    4920
tcttcgaact ttaattaaga tgttacttta attagcatgc cttaagctgg catacgtagc    4980
ggcaaatgca accacttaca attcatcaca aggcaataga tcgactggct ttcttgttaa    5040
agctaagcaa gtagttacct actgcgccaa taagaatatt gagcctactc cattggtacg    5100
atgggtaata tttataaatg cttgtcgttt aggagtagca agacactagt tctttcatat    5160
ttgtttgggt gccaatttag aaaactctcc gtacttcaaa tgtagtaaaa tactctccta    5220
ctgctctttg gacgatgaac gtctacacag acaaacagta gtcatatttg aagtgactcg    5280
ggagatattt taattctttt taactataag cagtagaatt gtaaagttgg tttcctccat    5340
cttaatccaa tgcacgaagt tcagaactct gctttgatta atagagctcg cagcgacttg    5400
catgctgttt tcacaacaag actcttgtag tattgcatct agccgtatat agatgagtcg    5460
gcaatgagtt aactctggct ctcactgtct cacacgctat tagggttcca gacttccagt    5520
ctacttgatt cagaaaaata caaatattct cttataagtt agcccaaaat aataaaatgg    5580
atatatattt gcgggcatta attggtctaa ctatgctcgg aggcctactg gtccaactcg    5640
cgtaggacat acaaactcat aaccgcataa tatacctgtt cagctatttg gttatacagt    5700
attgagttga ttcctgctgt tgactgaact gtagcaacgt ctgtatatat ccgggactaa    5760
```

```
tgataaattt tcagtttgga ttgcattatt cacaatatct tttaagcatt aatactgtat     5820
taattctctt gacacttcat ttttgtaata attttgttaa ttttccatag gttgattaat     5880
ttcaagttat cctatatact tatatagttc atctccacta agtgtagtta atgatatttc     5940
tctcctctta ttagactaca ttaccccaat tatttctagc cattggataa tagatatatg     6000
gttcaaattt tctcttcttt cttctctcat tacaccaagt aatctcaatc attttttaggc    6060 cttaaactca taagtatcaa tttgttttag ttttaatatt catatttcat cttatttgta     6120
catattatgc aacttaattt cccgcagcaa cgcggcagag tattcattta gttaatgtag     6180
acaacccaat atcacatgtg atcttacttg attatcattg attagaccct gtctaggaat     6240
aagaagcaaa tatgttctct ttcaacaaag ttatgtttgc ttaagagtct agggtgttgt     6300 atttccccttt aattctttct atagatagtt atacttgcta tcctgtttca tttctttttc    6360
ttaacgaaaa tgagatacag ttcagttgct taagcttttc ttgacatgta tgcttgtatt     6420
acatgtttac cttgactttg ccccagaagt ataccttcta tatatgca tattatcttt      6480 ccccaaaagg ttatacagac ccttttgaaa ggttgacatt ttagtatgcc gtagaaagta     6540
tatatccttt ggttataaag tgaacttgtt caaagtgcct caagaacatg gaaatacttt     6600
agcaaacaat gaagctactc cctccattta taattcattt catattataa gttactttga     6660
atttatttcc tagtcaaact attttaagtt cgactaaatt tatagaaaaa aataaaaata     6720
tttctaacac aaaataaaca ttttatcaaa tatgttcaat attaaattta acgaaactaa     6780
tttggtattg ttgatgttgc tattttttt ctataaattg gtcaaatgta aagatgcttg      6840
acttgggaaa aagtcaaaac gacttgtaat atgaaacgga tggagtaaga cttaataatg     6900
tttcagaact tgaaccatat cagtgctacc accaaaagct gatcattctg atatatgaaa     6960
atgtttattg ttagctttgc ccaaaaaacc gttttcatga actgcataaa tacaacaatt     7020
tattgttttt ttagggttct gtgtgtgggg gggtggtgtg ttaatccaac tcttgtgtta     7080
gaagtagatt ggcaaatcta ttctgtatta tatcttacat aagttcttat aagaataaac     7140
tgcaaaatgt aggtgttgtt atttacacca ctacgaagta cccccattta aattttgaat     7200
gtataacacc gttgactttt atacatatgt ttgaccgttc gtcttattaa aaaatacgta     7260
attgtcattt attttgttgt gatgtgtttt aagcatcaaa ggtagtttaa gcatgacttt     7320 ttttttacata attgcaaaaa agaatttgaa taaaacaaat ggcattttat tatgggttac    7380
gcatttacat gtcataatat ccactgtgac atttgagaaa cctattcatg ttttgaacta     7440
gagattatta gtagttgagg gcctttgtta gatgctgcta gtcctatgat tttggttagt     7500
acatgtatgg caagtgaaat cgtattgata ttatattccc acacaatatg taagttactt     7560
caacacataa atatataaca atatctagtt ttgtattact tatatatata tattctcatc     7620
atagtgatag tcactaactt acctattaag acattcaaag aaatgggcat ccttcagtta     7680
ggatgttaca gtgatacacc ttttcgtttt gacaatactg catacgcagt ttctaaaaca     7740
actccatgtt aaaacataag gggttgcact caagtagatt ttgaagtgtg tgtgcgcgcc     7800
tgtgcaactt tcttgttctt ccttcgtttt attttaaacc tggaaactaa agtaggtttc     7860
ctgttaaatt cctatccttt cttaaaaaaa tggacttcaa gaaaaaacag accagaatca     7920
taaatacagt gtatgtatct gacctgtata tgaaaaggta cagccatatg tgcatttgtt     7980
gttgagatgg aagaatatat atactgctta gttattatta caattatttc aaatgatgaa     8040
acgtatattc ctcattttc acagtatgga caaaatcctt gaacgttatg agcgctactc      8100
ctatgcagaa aaggtcctta tttcagctga atctgacact caggtaaaaa taaagagctc     8160
```

```
taattctgtt gtttctcata tctcaatatc ttgtttattt tttgaactttt tcactacacc    8220
tgtttcggtt gactcattca agacgggtac atccaacatt ttagctctcc tcaagttgga    8280
taaatcaatt aggcatcatt ttttatggca attttccatt gttatgtaga tcaactttta    8340
ataaatattg ctttacatct cttttgaacag taatctctta cttcaatgta cttatcaaat   8400
atgtagattt attctaaatt agattatatc cattttttat tacatagcgt cctgaccttt    8460
tggcatccca gcccaattga acctatttgc tgtctgaaat cttgaaaact caaactgaac   8520
tgttctttat attggtgcaa ttaattaggc tctctctctc aggtcagatc attaaaaatt    8580
gtggtattgt tacatttcat aagtgaaatt ttgttcacaa attagatcaa atttatcttc    8640
catgtttgtt tacacgtata cagctttgcc agttccctct tattcaaaca ttttttacac    8700
tatgattcaa ataccttttt gtggatttta ctggaacaaa atcatagtta ttgcctaatg    8760
aaaaactata aaaaaaaatt ttggatgcat gactacatca acactcatta tggaattttg   8820
tgtgccagag aatatcacaa aacatatttt tcatcaaata aaacaaaata aacatttttcc  8880
agaactttttg gcgtggctca tcagaagttt ggaaccttaa ataatccttg ttttcatttta  8940
gctgggactt actatagtca attatgctat taaaaagatc cattcgtcta tttgttacga    9000
ataatctttta ctctttagtt ggggttgatg gactaatggt gtactccaaa atcagaagtt  9060
cttttatggc tagatacatg tagaccggat ttgaaaactt tcaagtttag atttgacaaa   9120
aactttcaac tcgcgattga aaattttcaa gtccacattt gaaaactttc aagtttagat    9180
ttgaaaactt tcgacccaga tttgaaaact ttcaactcga gatttgaaaa ctttcaagcc   9240
tagatttaaa aacttttcaag ttcagattga aaaactttca agttaagatt tgaaaatttt  9300
cagctcaaat atttttgaaa acacgtatcc taacaattaa aaaaatcaga aaaaacacga  9360
aagaatagcg aaaaaagaa aaaaacgaaa aagatggaaa aaaaggaaac acaaaaaaaa   9420
aggaaaaaaa tcgcgtggga ccgccagctg gcgcgcgcgc cagttccgta actgacttgc   9480
gctcgccaat tagcatcccc catgtagaca tgcatattct tcgtttgcaa tattttttgt    9540
aagaagttgc tgtgtatgaa cattgttgac tgaactaatg tagttattat gcagacagtg   9600
gtaagtcata tttccatacc ataaagagtg agactgagaa ttttctaatc aagatattac    9660
aaaaagctga actagctagg cagactgtaa ccctgttatc attcctagaa atgtttgcta    9720
cttttggagat agtagataat atagttatca cgctgatgaa ttgtcaagga acatacatt   9780
atagttccct ttcctaacat gcactatctg cttagagctt ttctctatat agattttgga    9840
tggcactatt gtatactctt cagcacattc aatttctaaa cttgtaatat tagtgattct    9900
gtgcttagaa ttgtggaggt cactgtacat ccaccagtaa atttagtttg atgagtgtcg  9960
agaagaaaag gtaagtgtgg agtggggggac aaagttaatc atattttact gcaagcacac  10020
tgaagtaaat ccatttattc aatatacact gtacctaagc aattctccac ggaggtatct  10080
tgcagttcta ggtgtccaca gttttagcta tatgcagtgc caaaatcgat taaagttaca  10140
cttgttaata tagaaattca aggtactcca aagggcacaa tcatttgcac aatcagttct  10200
tcctggcaat ttttcaaata tcagctaatg tatgaatagt attgtgatac ttcctatta   10260
ctcaaattta ttaatgtaaa tcttctatgc ttgcttgtat agggcaactg gtgccacgaa  10320
tataggaaac tgaaggctaa ggttgagaca atacagaaat gtcaaaagta attggaaact  10380
actcacaact ggtgccatta tgacattatg tactatacac tgttgacata aaattgttcg  10440
ccttaaatcc tgcaggcacc tcatgggaga ggatcttgaa tctttgaatc tcaaagagct  10500
```

```
gcagcagctg gagcagcagc tggaaaattc gttgaaacat atcagatcca gaaaggtggt   10560 tttgtgatg agaattattc aaggctgata tcaacaatat gtgcaaaatt tatatggttt    10620
ttatacagct aaatatagat gtcctgtatg ttttacgagc tgacaattac aaatctcctt   10680
tatgtgcaga gccaactaat gctcgagtcc attaacgagc ttcaacggaa ggtaatgatg   10740
tcaaccatgt tagaccttta attgagtact gggacttgct agaaataacc ttgtcaaaac   10800
tcgagaaatc tttggccggc caccagttga taccatcgcg tgttatgttt catactctta   10860
ttttaagttc ccgccatgct tgcaactgca agtgctgcca cactttcatt ttctaacatg   10920
cacgccggat tcttgctgca ggaaaagtca ctgcaggagg agaataaggt cctacagaaa   10980
gaagtaggct gctagccttg atgcccccta gtttccatgc ttcagctgat cttggtttgt   11040
ttaacatcaa tcaagttaaa ttgacagaac ccttgctcct tcctacagct ggtggagaag   11100
cagaaagtcc agaagcaaca agtgcaatgg gaccagacac aacctcaaac aagttcctca   11160
tcatcctcct tcatgatgag ggaagccctt ccaacaacta atatcaggta agtaactagc   11220
agcctgaagt tagtttcgtc cttatgtagc acagacgaat aaccttttgg actaaagatc   11280
attagatcca gctttattag aaaacaaaat taaatggctc gtttagttca ctaccatatc   11340
aaaatattga cgatactaaa acctagacaa atattggaag tgctacattt ttttgtcaac   11400
ttatatatgt tatcactata ttttaatagc aaatcaaaca ttagctaaaa tactattaaa   11460
aataccaaca acttaatagg ggcatatttt ggcaccaacc accaaacaac tgaaagttct   11520
aacaaggttg tataaaccaa taactatcaa acctttttta ggcacctcag aatttacgc    11580 tttttttgt ctgaaaacac gccaaatctg ccccttttcc cccaaaacgc cagcgggctt    11640
tttcttgtca ttttggttgg tgatgtagct aagaggtgtg cttattcgtt ccacagtaac   11700
taccctgcag cagctggcga aaggatagag gatgtagcag cagggcagcc acagcatgtt   11760
cgcattgggc tgccaccatg gatgctgagc cacatcaacg gctaaggagg cttcagatcc   11820
ataccagtaa tcacaagttg caacctgacc cggtccggtc gcctgctgct ctggtttact   11880
actagtacta ttgtcatctt gcggttgcga gacgaggaaa gcattttagc cctaaattca   11940
gcattagtag caagctgcaa tgtgtatatt ttggcttcgt ccagcaccgt cttcctccca   12000
ccagtaattt acccatgtaa tatatgcgag tagcatgaac aaattttccc gtttccaacc   12060
atctccattg gtgtcatgtg tgacttaaat agcgaaattt cagcattgtg catagtgtga   12120
ttactgtaag ataaataaac tttgtagaca ataagtctcc gttatcttgc tgattggagc   12180
tgaatctgtc cgatcaccgg cagagctgat tgagcgcata ctgcataacg aataaattgt   12240
atgcgaacaa gttgataggc ataaatcgtt cgactgttta caaagaaaat aaggcgtgac   12300
attctcagtt aaataatggg agatcatctt gtatataatg atcttctgcc gtcactccta   12360
tacaaacatt ttacccatta caaaaaccaa gaaatatacc aaggcgccca agctcactgt   12420
cactgctgac tcccctacca ctaaaaattc tcaagagagg ataacgaatg ctaagcatta   12480
gtcttctaag aatggcattc agaactgtgg aactatgtgc cggctgatga gaactcagcc   12540
tatgaataaa ttaatctagc cacaacttta acataaagat attggtcaga ggttgtattt   12600
aactgaacag ggatatgcta gtattaaact cgaagcatct tctctttcag gcgtgaaatg   12660
aacttgaatg tctcctctgc tttgacctgt tgatacatat cacttcttga tactctgtcc   12720
ggatggaatt tcaaaagagc ttgcttgtaa gcagctttaa cctgaaaaaa gtttcatatt   12780
aaacaattgt cagcgggaag agatcaataa ttccttattt acatttatgg gtatcatttt   12840
atgaacttat atcagaacat ggcataaggt ggtaattgat ctcgcctaga ttgccagagg   12900
```

```
caataattgg caaatcttcc aaaatttgtc atgagaagct atctcttcta taaataaaca    12960
aacgaatttg ggatttctcc atagaaaatt gaaatacaat                         13000

<210> SEQ ID NO 16
<211> LENGTH: 947
<212> TYPE: DNA
<213> ORGANISM: Artificial Sequence
<220> FEATURE:
<223> OTHER INFORMATION: cDNA sequence of OsMADS14

<400> SEQUENCE: 16
atgggggccg gggctagggg ataggcggat agccagcagc caccaccacc agtagttgcc      60
gtgtggggat aggtgtggct atagggctag tggtcgtcgc tgatagcgag gtgggtaggg     120
ttaattttgg ttggaggtag agagagagag agagggaggg agggaggagg aggaggagga     180
ggaggaggag gaagaacagg aggaagatgg ggcggggcaa ggtgcagctg aagcggatcg     240
agaacaagat caaccggcag gtgaccttct ccaagcgcag gtcaaaactg ctcaagaagg     300
cgaatgagat ctccgtgctc tgcgacgccg aggtcgcgct catcatcttc tccaccaagg     360
gcaagctcta cgagtacgcc accgactcat gtatggacaa atccttgaa cgttatgagc      420 gctactccta tgcagaaaag gtccttattt cagctgaatc tgacactcag gcaactggt      480 gccacgaata taggaaactg aaggctaagg ttgagacaat acagaaatgt caaaagcacc     540
tcatgggaga ggatcttgaa tctttgaatc tcaaagagct gcagcagctg agcagcagc     600 tggaaaattc gttgaaacat atcagatcca gaaagagcca actaatgctc gagtccatta     660
acgagcttca acgaaggaa aagtcactgc aggaggagaa taaggtccta cagaaagaac      720
tggtggagaa gcagaaagtc cagaagcaac aagtgcaatg ggaccagaca caacctcaaa     780
caagttcctc atcatcctcc ttcatgatga gggaagccct tccaacaact aatatcagta     840
actaccctgc agcagctggc gaaaggatag aggatgtagc agcagggcag ccacagcatg     900
aacgcattgg gctgccacca tggatgctga gccacatcaa cggctaa                   947

<210> SEQ ID NO 17
<211> LENGTH: 540
<212> TYPE: DNA
<213> ORGANISM: Artificial Sequence
<220> FEATURE:
<223> OTHER INFORMATION: cDNA sequence of truncated OsMADS14

<400> SEQUENCE: 17
atggggcggg gcaaggtgca gctgaagcgg atcgagaaca gatcaaccg gcaggtgacc       60 ttctccaagc gcaggtcaaa actgctcaag aaggcgaatg agatctccgt gctctgcgac     120
gccgaggtcg cgctcatcat cttctccacc aagggcaagc tctacgagta cgccaccgac     180
tcatgtatgg acaaaatcct tgaacgttat gagcgctact cctatgcaga aaaggtcctt     240
atttcagctg aatctgacac tcagggcaac tggtgccacg aatataggaa actgaaggct     300
aaggttgaga caatacagaa atgtcaaaag cacctcatgg gagaggatct tgaatctttg     360
aatctcaaag agctgcagca gctggagcag cagctggaaa attcgttgaa acatatcaga     420
tccagaaaga gccaactaat gctcgagtcc attaacgagc ttcaacggaa ggaaaagtca     480
ctgcaggagg agaataaggt cctacagaaa gaactggtgg agaagcagaa agtccagtaa     540

<210> SEQ ID NO 18
<211> LENGTH: 179
<212> TYPE: PRT
```

```
<213> ORGANISM: Artificial Sequence
<220> FEATURE:
<223> OTHER INFORMATION: OsMADS14 protein

<400> SEQUENCE: 18

Met Gly Arg Gly Lys Val Gln Leu Lys Arg Ile Glu Asn Lys Ile Asn
1               5                   10                  15

Arg Gln Val Thr Phe Ser Lys Arg Arg Ser Lys Leu Leu Lys Lys Ala
                20                  25                  30

Asn Glu Ile Ser Val Leu Cys Asp Ala Glu Val Ala Leu Ile Ile Phe
            35                  40                  45

Ser Thr Lys Gly Lys Leu Tyr Glu Tyr Ala Thr Asp Ser Cys Met Asp
    50                  55                  60

Lys Ile Leu Glu Arg Tyr Glu Arg Tyr Ser Tyr Ala Glu Lys Val Leu
65                  70                  75                  80

Ile Ser Ala Glu Ser Asp Thr Gln Gly Asn Trp Cys His Glu Tyr Arg
                85                  90                  95

Lys Leu Lys Ala Lys Val Glu Thr Ile Gln Lys Cys Lys Lys His Leu
                100                 105                 110

Met Gly Glu Asp Leu Glu Ser Leu Asn Leu Lys Glu Leu Gln Gln Leu
            115                 120                 125

Glu Gln Gln Leu Glu Asn Ser Leu Lys His Ile Arg Ser Arg Lys Ser
    130                 135                 140

Gln Leu Met Leu Glu Ser Ile Asn Glu Leu Gln Arg Lys Glu Lys Ser
145                 150                 155                 160

Leu Gln Glu Glu Asn Lys Val Leu Gln Lys Glu Leu Val Glu Lys Gln
                165                 170                 175

Lys Val Gln

<210> SEQ ID NO 19
<211> LENGTH: 28
<212> TYPE: DNA
<213> ORGANISM: Artificial Sequence
<220> FEATURE:
<223> OTHER INFORMATION: sequence of forward primer at 5' UTR (F1)

<400> SEQUENCE: 19
atcaagcttt acggccaaac cctacagc                                          28

<210> SEQ ID NO 20
<211> LENGTH: 28
<212> TYPE: DNA
<213> ORGANISM: Artificial Sequence
<220> FEATURE:
<223> OTHER INFORMATION: sequence of reverse primer at 3' UTR (R1)

<400> SEQUENCE: 20
ttgggtaccg atgggtagtg gagtctgc                                          28

<210> SEQ ID NO 21
<211> LENGTH: 28
<212> TYPE: DNA
<213> ORGANISM: Artificial Sequence
<220> FEATURE:
<223> OTHER INFORMATION: sequence of forward primer

<400> SEQUENCE: 21
atcaagcttg ttggttcatc ggcgatcg                                          28

<210> SEQ ID NO 22
```

```
<211> LENGTH: 29
<212> TYPE: DNA
<213> ORGANISM: Artificial Sequence
<220> FEATURE:
<223> OTHER INFORMATION: sequence of reverse primer

<400> SEQUENCE: 22
ttgggtaccg agatccagct tattcctgg                                29

<210> SEQ ID NO 23
<211> LENGTH: 20
<212> TYPE: DNA
<213> ORGANISM: Artificial Sequence
<220> FEATURE:
<223> OTHER INFORMATION: sequence of forward primer in the I region (F2)

<400> SEQUENCE: 23
aaagctgacg ctgatggttt                                          20

<210> SEQ ID NO 24
<211> LENGTH: 21
<212> TYPE: DNA
<213> ORGANISM: Artificial Sequence
<220> FEATURE:
<223> OTHER INFORMATION: sequence of reverse primer in hph gene in T-DNA
      (R2)

<400> SEQUENCE: 24
atccagactg aatgcccaca g                                        21
```